US009322034B2

(12) United States Patent
Carlock et al.

(10) Patent No.: US 9,322,034 B2
(45) Date of Patent: Apr. 26, 2016

(54) COMPOSITIONS AND METHODS FOR DETECTING AND MODULATING CELL DEATH BY A TRANSLATION REGULATED GENE EXPRESSION SYSTEM

(75) Inventors: Leon Carlock, Bloomfield, MI (US); Maria Cypher, Magnolia, TX (US)

(73) Assignee: Wayne State University, Detroit, MI (US)

( * ) Notice: Subject to any disclaimer, the term of this patent is extended or adjusted under 35 U.S.C. 154(b) by 1180 days.

(21) Appl. No.: 12/672,989

(22) PCT Filed: Aug. 7, 2008

(86) PCT No.: PCT/US2008/072465
§ 371 (c)(1),
(2), (4) Date: Apr. 19, 2011

(87) PCT Pub. No.: WO2009/023517
PCT Pub. Date: Feb. 19, 2009

(65) Prior Publication Data
US 2011/0191874 A1    Aug. 4, 2011

Related U.S. Application Data

(60) Provisional application No. 60/955,265, filed on Aug. 10, 2007, provisional application No. 60/981,044, filed on Oct. 18, 2007.

(51) Int. Cl.
| | |
|---|---|
| *C07H 21/04* | (2006.01) |
| *C12Q 1/00* | (2006.01) |
| *C12N 15/00* | (2006.01) |
| *C12N 15/63* | (2006.01) |
| *A61K 31/70* | (2006.01) |
| *A01K 67/00* | (2006.01) |
| *C12N 15/85* | (2006.01) |
| *C07K 14/47* | (2006.01) |
| *G01N 33/50* | (2006.01) |
| *A61K 38/00* | (2006.01) |
| *A61K 48/00* | (2006.01) |

(52) U.S. Cl.
CPC ............ *C12N 15/85* (2013.01); *A61K 48/0066* (2013.01); *C07K 14/4713* (2013.01); *G01N 33/5014* (2013.01); *A01K 2217/052* (2013.01); *A01K 2227/105* (2013.01); *A01K 2267/0393* (2013.01); *A61K 48/00* (2013.01); *C12N 2799/025* (2013.01); *C12N 2799/026* (2013.01); *C12N 2840/10* (2013.01); *C12N 2840/203* (2013.01); *C12N 2840/44* (2013.01); *C12N 2840/85* (2013.01); *G01N 2510/00* (2013.01)

(58) Field of Classification Search
CPC ............... C12N 15/85; C12N 2840/10; A01K 2217/052; A01K 2267/0393; A01K 48/066; G01N 33/5017; G01N 2510/00
USPC ............. 536/24.1; 435/4, 320.1, 455; 514/44; 800/13
See application file for complete search history.

(56) References Cited

U.S. PATENT DOCUMENTS

| | | | |
|---|---|---|---|
| 6,159,709 A | 12/2000 | Korneluk et al. | |
| 6,171,821 B1 | 1/2001 | Korneluk et al. | |
| 6,274,341 B1 | 8/2001 | Bailey et al. | |
| 6,653,132 B1 | 11/2003 | Keshet et al. | |
| 6,764,852 B2 * | 7/2004 | Cornelis et al. | 435/325 |
| 7,794,976 B2 * | 9/2010 | Handa et al. | 435/69.1 |
| 8,021,875 B2 * | 9/2011 | Wooddell et al. | 435/320.1 |
| 2006/0173168 A1 | 8/2006 | Carlock et al. | |

FOREIGN PATENT DOCUMENTS

WO    01/55371 A1    8/2001

OTHER PUBLICATIONS

Addgene Vector Database. Plasmid: pGFP-C3, 2013, pp. 1-3.*
Holcik, Martin et al., The Internal Ribosome Entry Site-Mediated Translation of Antiapoptotic Protein XIAP is Modulated by the Heterogeneous Nuclear Ribonucleoproteins C1 and C2, Molecular and Cellular Biology, Jan. 2003, vol. 23, No. 1, pp. 280-288.
Nevins, Tara A. et al., Distinct Regulation of Internal Ribosome Entry Site-mediated Translation following Cellular Stress is Mediated by Apoptotic Fragments of eIF4G Translation Initiation Factor Family Members eIF4GI and p97/DAP5/NAT1, The Journal of Biological Chemistry, Feb. 2003, vol. 278, No. 6, pp. 3572-3579.
Anderson, W. F., "Prospects forHluman Gene Therapy," Science, Oct. 26, 1984, pp. 401-409, vol. 226.
Baird, S. D., et al., "Searching for IRES," RNA, 2006, pp. 1755-1785, vol. 12, No. 10.
Bonnal, S., et al., "IRESdb: The Internal Ribosome Entry Site Database," Nucleic Acids Research, 2003, pp. 427-428, vol. 31, No. 1.
Cornetta, K., et al., "Gene Transfer into Primates and Prospects for Gene Therapy in Humans," Progress in Nucleic Acid Research and Molecular Biology, 1987, pp. 311-322, vol. 36.
Eglitis, M. A., et al., "Retroviral Vectors for Introduction of Genes into Mammalian Cells," BioTechniques, 1988, pp. 608-614, vol. 6 No. 7.
Friedmann, T., "Progress Toward Human Gene Therapy," Science, Jun. 16, 1989, pp. 1275-1281, vol. 244, No. 4910.
Gossen, M., et al., "Tight Control of Gene Expression in Mammalian Cells by Tetracycline-Responsive Promoters," Proc. Natl. Acad. Sci. USA, Jun. 1992, pp. 5547-5551, vol. 89.
Guhaniyogi, J., et al., "Regulation of mRNA Stability in Mammalian Cells," Gene an International Journal of Genes and Genomes, 2001, pp. 11-23, vol. 265.
Jang, S. K., et al., "A Segment of the 5' Nontranslated Region of Encephalomyocarditis Virus RNA Directs Internal Entry of Ribosomes During in Vitro Translation," Journal of Virology, Aug. 1988, pp. 2636-2643, vol. 62, No. 8.
Johnson, L. G., "Gene Therapy for Cystic Fibrosis," Chest, Feb. 1995, pp. 77S-83S, vol. 107, No. 2.
Le Gal La Salle, G., et al., "An Adenovirus Vector for Gene Transfer into Neurons and Glia in the Brain," Science, Feb. 12, 1993, pp. 988-990, vol. 259.
Miller, A. D., et al., "Improved Retroviral Vectors for Gene Transfer and Expression," Biotechniques, Oct. 1989, pp. 980-990, vol. 7, No. 9.
Miller, A. D. "Retrovirus Packaging Cells," Human Gene Therapy, 1990, pp. 5-14, vol. 1.

(Continued)

*Primary Examiner* — Quang Nguyen
(74) *Attorney, Agent, or Firm* — Senniger Powers LLP

(57) ABSTRACT

The technology relates to a nucleic acid expression cassette comprising a TR element encoding an mRNA molecule that is translated in stressed and/or dying cells, and a nucleotide sequence operably linked to the TR element, that is a first open reading frame (ORF) sequence and encodes a polypeptide or a fragment thereof and is co-translated with the TR element. The technology further relates to mammalian cells and a transgenic animal comprising such expression cassette. Further included are kits comprising the expression cassette, and methods for determining toxicity, and killing a target cell.

56 Claims, 32 Drawing Sheets

(56) References Cited

OTHER PUBLICATIONS

Figure 1A:
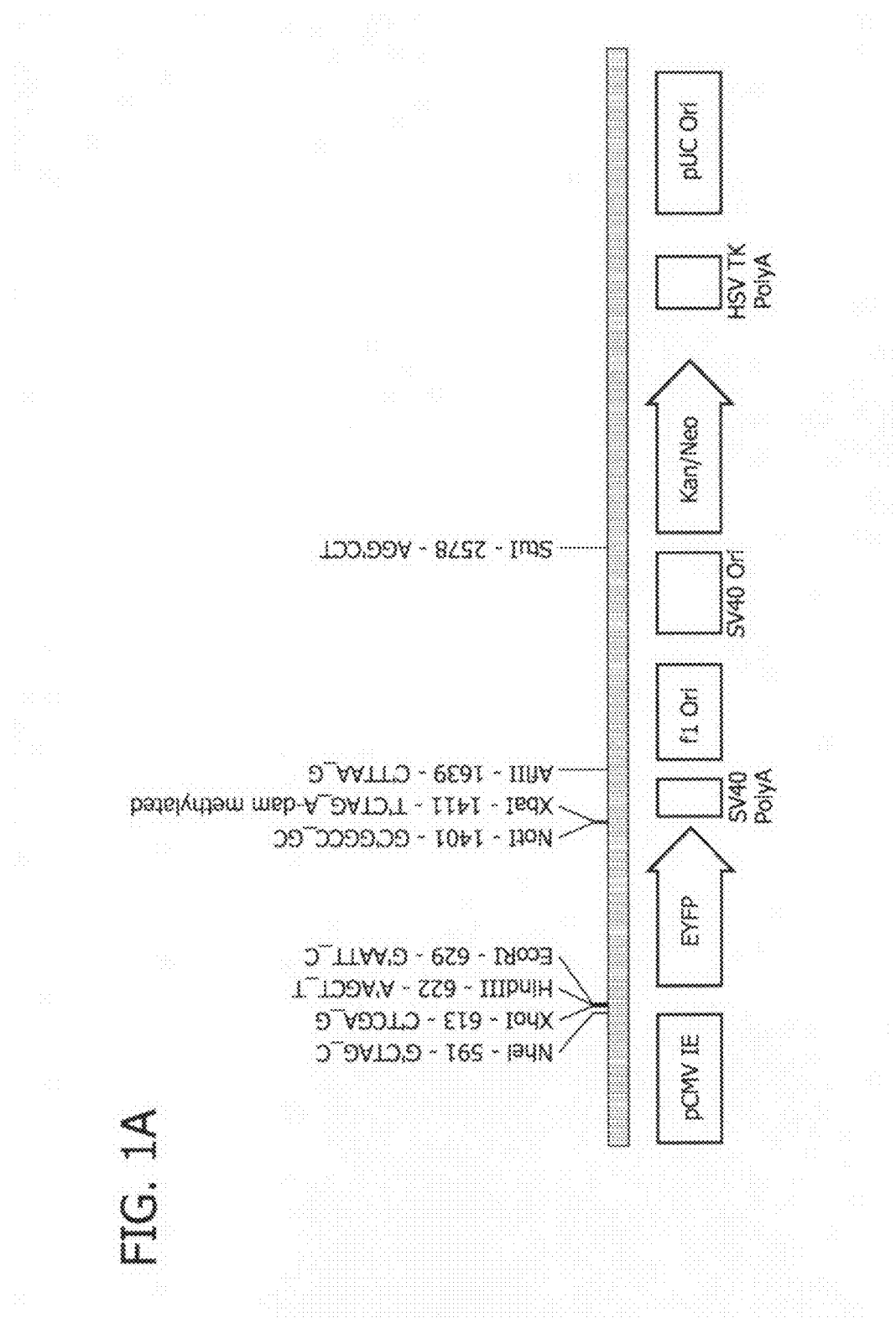

Moen, R. C., "Drections in Gene Therapy," Blood Cells, 1991, pp. 407-416, vol. 17.

Mountford, P. S., et al., "Internal Ribosome Entry Sites and Dicistronic RNAs in Mammalian Transgenesis," TIG, May 1995, pp. 179-184, vol. 11, No. 5.

Sharp, D., "Gene Therapy," The Lancet, May 25, 1991, pp. 1277-1278, vol. 337.

Tolstoshev, P., et al., "Gene Expression Using Retroviral Vectors," Current Opinion in Biotechnology, 1990, pp. 55-61, vol. 1.

Badura, M., et al., "DNA Damage and eIF4G1 in Breast Cancer Cells Reprogram Translation for Survival and DNA Repair mRNAs," PNAS, Nov. 13, 2012, pp. 18767-18772, vol. 109, No. 46.

* cited by examiner

|   | Clone Name | Treatment |
|---|---|---|
| 1 | fLuc-TR$_{plp}$-EYFP | Calcium Ionophore A23187 |
| 2 | fLuc-TR$_{plp}$-EYFP | MG132 |
| 3 | fLuc-TR$_{dm}$-EYFP | Calcium Ionophore A23187 |
| 4 | fLuc-TR$_{dm}$-EYFP | MG132 |
| 5 | cuLf-TR$_{plp}$-EYFP | Calcium Ionophore A23187 |
| 6 | cuLf-TR$_{plp}$-EYFP | MG132 |
| 7 | cuLf-TR$_{dm}$-EYFP | Calcium Ionophore A23187 |
| 8 | cuLf-TR$_{dm}$-EYFP | MG132 |

FIG. 6A

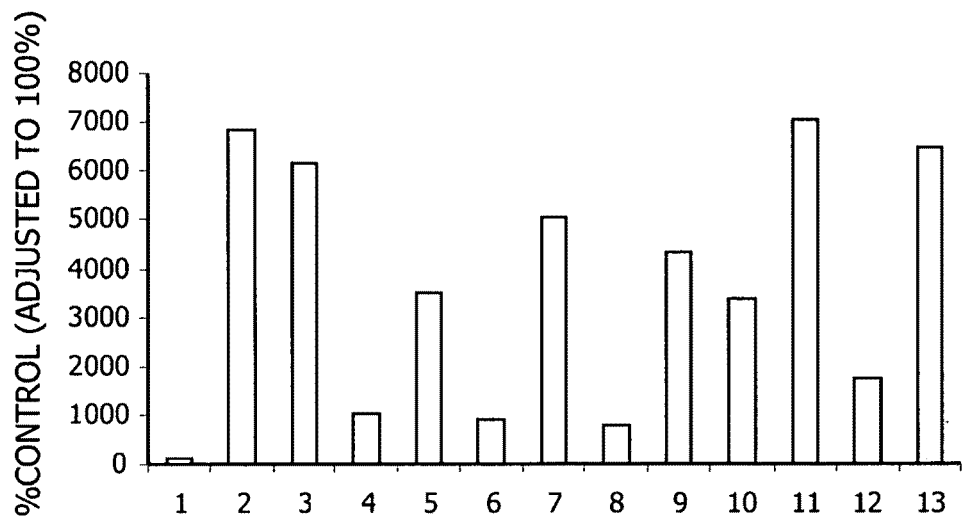

| Number | Name | Treatment |
|---|---|---|
| 1 | HEK293 Control | Calcium Ionophore A23187 |
| 2 | HEK293 CMV-fLuc | Untreated |
| 3 | HEK293 CMV-fLuc | Calcium Ionophore A23187 |
| 4 | HEK293 TR$_{pip}$-fLuc pool | Untreated |
| 5 | HEK293 TR$_{pip}$-fLuc pool | Calcium Ionophore A23187 |
| 6 | HEK293 TR$_{pip}$-fLuc subclone #3 | Untreated |
| 7 | HEK293 TR$_{pip}$-fLuc subclone #3 | Calcium Ionophore A23187 |
| 8 | HEK293 TR$_{pip}$-fLuc subclone #17 | Untreated |
| 9 | HEK293 TR$_{pip}$-fLuc subclone #17 | Calcium Ionophore A23187 |
| 10 | HEK293 TR$_{pip}$-fLuc subclone #13 | Untreated |
| 11 | HEK293 TR$_{pip}$-fLuc subclone #13 | Calcium Ionophore A23187 |
| 12 | HEK293 TR$_{pip}$-fLuc subclone #16 | Untreated |
| 13 | HEK293 TR$_{pip}$-fLuc subclone #16 | Calcium Ionophore A23187 |

FIG. 6B

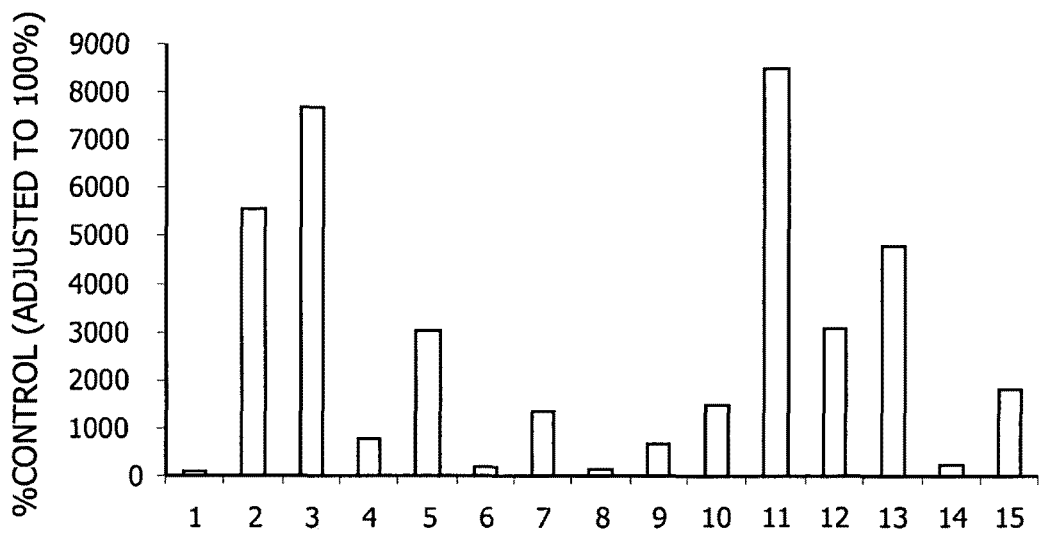

| Number | Name | Treatment |
|---|---|---|
| 1 | HEK293 Control | Calcium Ionophore A23187 |
| 2 | HEK293 CMV-fLuc | Untreated |
| 3 | HEK293 CMV-fLuc | Calcium Ionophore A23187 |
| 4 | HEK293 TR$_{dm}$-fLuc pool | Untreated |
| 5 | HEK293 TR$_{dm}$-fLuc pool | Calcium Ionophore A23187 |
| 6 | HEK293 TR$_{dm}$-fLuc subclone #12 | Untreated |
| 7 | HEK293 TR$_{dm}$-fLuc subclone #12 | Calcium Ionophore A23187 |
| 8 | HEK293 TR$_{dm}$-fLuc subclone #43 | Untreated |
| 9 | HEK293 TR$_{dm}$-fLuc subclone #43 | Calcium Ionophore A23187 |
| 10 | HEK293 TR$_{dm}$-fLuc subclone #45 | Untreated |
| 11 | HEK293 TR$_{dm}$-fLuc subclone #45 | Calcium Ionophore A23187 |
| 12 | HEK293 TR$_{dm}$-fLuc subclone #2 | Untreated |
| 13 | HEK293 TR$_{dm}$-fLuc subclone #2 | Calcium Ionophore A23187 |
| 14 | HEK293 TR$_{dm}$-fLuc subclone #8 | Untreated |
| 15 | HEK293 TR$_{dm}$-fLuc subclone #8 | Calcium Ionophore A23187 |

| | Clone Name | Treatment | Timepoint |
|---|---|---|---|
| 1 | TR$_{pip}$-fLuc subclone #3 | Calcium Ionophore A23187 | 12hr |
| 2 | TR$_{pip}$-fLuc subclone #17 | Calcium Ionophore A23187 | 12hr |
| 3 | TR$_{pip}$-fLuc subclone #12 | Calcium Ionophore A23187 | 12hr |
| 4 | TR$_{dm}$-fLuc subclone #45 | Calcium Ionophore A23187 | 12hr |

FIG. 14

```
       1         10        20        30        40        50        60        70
       |         |         |         |         |         |         |         |
 1) mygvlpwnafpgkvcgsnllsicktaefqmtfhlfiaafvgaaatlvslltfmiaatynfavlklmgrgtkf
 2) mygvlpwnafpgkvcgsnllsicktaefqmtfhlfiaafvgaaatlvslltfmiaatynfavlklmgrgtkf
 3) mygvlpwnafpgkvcgsnllsicktaefqmtfhlfiaafvgaaatlvslltfmiaatynfavlklmgrgtkf
 4) mygvlpwnafpgkvcgsnllsicktaefqmtfhlfiaafvgaaatlislltfmiaatynfavlklmgrgtkf
 5) mygvlpwnafpgkvcgsnllsicktaefqmtfhlfiaafvgaaatlislltfmiaatynfavlklmgrgtkf
 6) mygvlpwnafpgkvcgsnllsicktaefqmtfhlfiaafvgaaatlvslltfmiaatynfavlklmgrgtkf
 7) mygvlpwnafpgkvcgsnllsicktaefqmtfhlfiaafvgaaatlvslltfmiaatynfavlklmgrgtkf
 8) mygvlpwnafpgkvcgsnllsicktaefqmtfhlfiaafvgaaatlvslltfmiaatynfavlklmgrgtkf
 9) mygvlpwnafpgkvcgsnllsicktaefqmtfhlfiaafigaaatlvslltfmiaatynfavlklmgrgtkf
10) mygvlpwnafpgkvcgsnllsicktaefqmtfhlfiaafvgaaatlvslltfmiaatynfavlklmgrgtkf
11) mygvlpwnafpgkvcgsnllsicktaefqmtfhlfiaafvgaaatlvslltfmiaatynfavlklmgrgtkf
12) mygvlpwnafpgkvcgsnllsicktaefqmtfhlfiaafvgaaatlvslltfmiaatynfavlklmgrgtkf
13) mygvlpwnafpgkvcgsnllsicktsefqmtfhlfiaafvgaaatlvslltfmiaatynfavlklmgrgtkf
14) mygilpwnafpgkvcgsnllsicktsefqmtfhlfiaafvgaaatlvslvtfiiattynfavlrlmgrgtkf
15) mygvlpwnaspgrvcgqsllsicktaefqmtfhlfiaafvgaaitlvalltfiiaatynfavlklmgrgtkf
16) mygvlpwnafpgkvcgtsllaicktsefqmtfhlfiaafvgaaatlvalltymvgasfnyavlrvtgrsdrskf
17) mdprqygvlpwtatpgkvcgmalvsicnkpefnmtyhlfitaftgaaatlvslltymmsttynfavlrflgred
    fctkf
```

FIG. 15A

```
          10         20         30         40         50         60         70         80         90        100
           |          |          |          |          |          |          |          |          |          |
mDM  atgggcttgttagagtgttgtgctagatgtctggtaggggcccccttgcttccctggtggcactggattgtgttcttcttggagtggcactgttctgtg
mP   atgggcttgttagagtgttgtgctagatgtctggtaggggcccccttgcttccctggtggcactggattgtgttcttcttggagtggcactgttctgtg
TRd  ttgagtgagttagagtgttgtgctagtgagctagtgttgtctggtagtgtctggtaggggcccccttgcttccctggtggcactggattgtgttcttcttggagtggcactgttctgtg
TRp  ttcagtgagttagagtgttgtgctagtgagctagtgttgtctggtagtgtctggtaggggcccccttgcttccctggtggcactggattgtgttcttcttggagtggcactgttctgtg
hDM  atgggcttgttagagtgctgtgcaagatgtctggtaggggcccccttgcttccctggtggcactggattgtgttcttcttggggtggcactgttctgtg
hP   atgggcttgttagagtgctgtgcaagatgtctggtaggggcccccttgcttccctggtggcactggattgtgttcttcttggggtggcactgttctgtg 110        120        130        140        150        160        170        180        190        200
           |          |          |          |          |          |          |          |          |          |
mDM  gatgtggacatgaagctctcactggtacagagaaaagctaattgagacctattctccaaaaactaccaggactatgagtatctcattaatgtgattcatgc
mP   gatgtggacatgaagctctcactggtacagagaaaagctaattgagacctattctccaaaaactaccaggactatgagtatctcattaatgtgattcatgc
TRd  gatgtggacatgaagctctcactggtacagagaaaagctaattgagacctattctccaaaaactaccaggactatgagtatctcattaatgtgattcatgc
TRp  gatgtggacatgaagctctcactggtacagagaaaagctaattgagacctattctccaaaaactaccaggactatgagtatctcattaatgtgattcatgc
hDM  gctgtggacatgaagctctcactggcacccctgcctcttcttcttcttcttcttctctcaagactagagaagcttctacaccgcgctgtcaggcaggcagatc
hP   gctgtggacatgaagctctcactggcacccctgcctcttcttcttcttcttcttctctcaagactagagaagcttctacaccgcgctgtcaggcaggcagatc 210        220        230        240        250        260        270        280        290        300
           |          |          |          |          |          |          |          |          |          |
mDM  tttccagtatgtcatctatgaactgcctcttttcttcttcttcttcttcttcttcttcttcttcttcttcctttatggggccctcctgctggcctcctgctgtcaggcaggcagatc
mP   tttccagtatgtcatctatgaactgcctcttttcttcttcttcttcttcttcttcttcttcttcttcttcctttatggggccctcctgctggcctcctgctgtcaggcaggcagatc
TRd  tttccagtatgtcatctatgaactgcctcttttcttcttcttcttcttcttcttcttcttcttcttcttcctttatggggccctcctgctggcctcctgctgtcaggcaggcagatc
TRp  tttccagtatgtcatctatgaactgcctcttttcttcttcttcttcttcttcttcttcttcttcttcttcctttatggggccctcctgctggcctcctgctgtcaggcaggcagatc
hDM  cttgtggactacaagaccaccatctgcggccaagggcctgagcgcaacgtaacaggggccagaacggggttccagaggccaacatcaagcttcatt
hP   cttgtggactacaagaccaccatctgcggccaagggcctgagcgcaacgtaacaggggccagaacggggttccagaggccaacatcaagcttcatt 310        320        330        340        350        360        370        380        390        400
           |          |          |          |          |          |          |          |          |          |
hDM  tttggcgactacaagaccaccatctgcggccaagggcctgagcgcaacg----------------------------------------------
hP   tttggcgactacaagaccaccatctgcggccaagggcctgagcgcaacg----------------------------------------------
TRd  tttggcgactacaagaccaccatctgcggccaagggcctgagcgcaacg----------------------------------------------
TRp  tttggcgactacaagaccaccatctgcggccaagggcctgagcgcaacg----------------------------------------------
hDM  tttggcgactacaagaccaccatctgcggccaagggcctgagcgcaacgtaacaggggccagaacggggaggggttccagaggccaacatcaagcttcatt
hP   tttggcgactacaagaccaccatctgcggccaagggcctgagcgcaacgtaacaggggccagaacggggaggggttccagaggccaacatcaagcttcatt
```

FIG. 15B

FIG. 15C

```
         710        720        730        740        750        760        770        780        790        800
          |          |          |          |          |          |          |          |          |          |
mDM  aaatgaccttccacctgttattgctgcgttttgtggtgctgcggccacactagtttccctgctcaccttcatgattgctgccacttacaacttcgccgt
mP   aaatgaccttccacctgttattgctgcgttttgtggtgctgcgtgcggccacactagtttccctgctcaccttcatgattgctgccacttacaacttcgccgt
TRd  aattgaccttccacctgttattgctgcgtttgtgcgtgctgcggccacactagtttccctgctcaccttcatgattgctgccacttacaacttcgccgt
TRp  aattgaccttccacctgttattgctgcgtttgtgcgtgctgcggccacactagtttccctgctcaccttcatgattgctgccacttacaacttcgccgt
hDM  aaatgaccttccacctgttattgctgcgtttgtgcgtgctgcggggctgcagctgcagctacactgttccctgctcaccttcatgattgctgccacttacaacttgccgt
hP   aaatgaccttccacctgttattgctgcgtttgtgcgtgctgcgggggctgcagctgcagctacactgttccctgctcaccttcatgattgctgccacttacaacttgccgt
          |          |          |          |          |          |          |          |          |
         600        610        620        630        640        650        660        670        680        690

810        820        830        840        850
          |          |          |          |          |
mDM  ccttaaactcatgggccgaggccaccaagttctga
mP   ccttaaactcatgggccgaggccaccaagttctga
TRd  ccttaaactcatgggccgaggccaccaagttc
TRp  ccttaaactcatgggccgaggccaccaagttc
hDM  ccttaaactcatgggccgaggccaccaagttctga
hP   ccttaaactcatgggccgaggccgatacactggtttccctg
          |          |          |          |          |
         700        710        720        730        740
```

COMPOSITIONS AND METHODS FOR DETECTING AND MODULATING CELL DEATH BY A TRANSLATION REGULATED GENE EXPRESSION SYSTEM

CROSS-REFERENCE TO RELATED APPLICATIONS

This application is a 35 U.S.C. §371 application of PCT/US2008/072465, filed on Aug. 7, 2008, which claims the benefit of U.S. Provisional Patent Application Ser. No. 60/981,044, filed Oct. 18, 2007, and U.S. Provisional Patent Application Ser. No. 60/955,265, filed Aug. 10, 2007. The entire contents of these related applications are hereby incorporated by reference herein.

SEQUENCE LISTING

The instant application contains a Sequence Listing as a text file, which is entitled "WSUM.06796.US_ST25," was created on Dec. 12, 2013, and is 53,809 bytes in size. This sequence listing was submitted via EFS-Web in ASCII format on Dec. 16, 2013, and is hereby incorporated by reference in its entirety. This sequence listing contain 63 sequences, which were submitted on Mar. 8, 2010 in a Sequence Listing in PCT/US2008/072465, filed on Aug. 7, 2008, of which the instant application is a 35 U.S.C. §371 national stage application.

BACKGROUND

The present technology relates to Translational Regulatory (e.g. TR) nucleic acid molecules encoding mRNA molecules that are selectively translated and detected early in stressed and/or dying cells. In various embodiments, the technology relates to expression cassettes comprising such TR elements, mammalian cells and transgenic animals comprising such expression cassettes, and methods of use and treatment.

Normal biological activity in a living organism combines endogenous expression of genes that constitute an individual's genome with responses to the outside world. In higher eukaryotes, gene expression begins in the nucleus with transcription of genomic DNA into a pre-mRNA or "primary" RNA transcript. While still in the nucleus, the pre-mRNA is modified to include a 5' cap structure, forms heteronuclear ribonucleoprotein (hnRNP) complexes, acquires a 3' polyadenylate tail and undergoes splicing to remove intervening DNA sequences (e.g. introns). The mature mRNA is then exported to the cytoplasm where protein complexes direct (1) association with ribosomes via the 5' cap structure, termed Cap-dependent translation, or (2) interaction with cytosolic RNA binding proteins that facilitate mRNA storage, processing or degradation. Following ribosome-driven translation, sequential shortening of the 3'-polyadenylate tail results in transport of the mRNA body to a complex of ribonucleases (RNAses), termed the exosome, which degrades the aged mRNA and effectively terminates protein synthesis.

As expected, gene expression is a highly regulated process that must produce a desired gene product (typically a polypeptide) at a particular time, rate and quantity. In addition to transcriptional regulation, post-transcriptional processes such as mRNA decay and translation are key checkpoints in gene expression. It is not surprising that changes in a cellular expression profile, produced by genetic mutations or aberrant responses to external stimuli can cause severe abnormalities that often result in cell death and the manifestation of a disease phenotype.

Extensive or prolonged cellular stimulation by environmental factors, such as altered nutrient levels, cytokines, hormones and temperature shifts, as well as environmental stresses like hypoxia, hypocalcemia, viral infection and tissue injury, results in the rapid attenuation of cap-dependent translation. This process is adaptive as it curtails the global synthesis of proteins which is not needed for an immediate stress response and recovery. However, this translational abatement does not completely eliminate ribosome activity, since many products of stress response and recovery genes continue to be synthesized by an alternative process, termed cap-independent translation (reviewed in Guhaniyogi & Brewer, 2001, Gene 265(1-2):11-23).

Cap-independent translation occurs by direct recruitment of ribosomes to specific RNA structures termed Internal Ribosome Entry Sites (IRESs). Bypassing the requirement for a 5' mRNA cap structure was initially described as a mechanism for translating viral RNAs irrespective of a near complete inhibition of cellular cap-dependent translation in infected cells (Jang et al., 1988, J. Virol., 62:2636-43). Generally, IRES sequences cannot be identified by sequence homology and well characterized IRES elements have been verified using functional assays (Mountford and Smith, 1995, TIG, 11(5): 179-184; Baird et al., 2006, NAR, 12(10):1755-85). Current evidence shows that the conformation of the IRES RNA and the binding of accessory proteins to specific mRNA sequences enable ribosome binding. In eukaryotic cells, IRES-directed translation has often been associated with 5' untranslated regions (5'UTRs) of mRNAs that contain unusually long and thermodynamically stable RNA secondary structures with multiple short open reading frames (ORFs) that dramatically inhibit the initiation of ribosome-dependent translation. However, functional verification of IRES activity for many of these 5' UTR IRES elements has been complicated by the presence of transcriptional effector sequences cloned from the overlapping 5' gene promoter. Attempts to employ these 5'UTR elements in IRES reporter vectors have been complicated by this residual background transcriptional activity which masks any translational regulation produced by these sequences.

IRES elements have been identified in a number of eukaryotic mRNAs (Bonnal S et al., (2003) Nucleic Acids Res. 31:427-428) and ensure the efficient expression of proteins or fragments thereof during nuclear inactivity or acute cellular stress when "cap-dependent" translation initiation is inhibited (i.e., apoptosis, starvation, gamma-irradiation, hypoxia, mitosis, or terminal differentiation). U.S. Published Patent Application No. 2006/0173168 discloses two low molecular peptides from the C-terminus of the PLP/DM20 gene, PIRP-M and PIRP-L, which are produced by internal translation initiation at an IRES.

The impact of chemical or biopharmaceutical intervention on the overall health of a specific individual is often uncertain. While a pharmaceutical molecule may remedy a targeted symptom, the treatment may be accompanied by serious side effects or unexpected toxicity that can, in some cases be worse than the initial malady. Although the side effects and toxicity of a pharmaceutical preparation are often known and may be limited to a small subset of individuals, these effects may be so severe in this small subset of individuals that a drug may not achieve FDA approval which results in huge pharmaceutical losses.

A large number of chemicals are manufactured in the United States annually. Over 2,000 new chemicals are introduced into the market each year, although very few are comprehensively tested for acute or chronic toxicity. In order to define the potential toxicity of a novel drug or chemical, the Food and Drug Administration (FDA) requires a New Drug Application (NDA) to include a large battery of toxicity, carcinogenicity, mutagenicity and reproductive/fertility tests in at least two animal species. The frequent, invasive testing and postmortem endpoint has raised considerable criticism from animal rights groups and the general public about animal suffering.

This situation underscores the need in the art for alternative, high-throughput molecular and biological screening technologies capable of detecting cell stress and toxicity in a broad spectrum of cell types following acute or chronic exposure to a chemical. Accordingly, novel methods for efficient and less expensive toxicity testing that provide a reliable alternative to animal testing are needed.

SUMMARY

Among the various aspects of the present technology are nucleic acid expression cassettes, which are expressible in mammalian cells and have the following elements in a 5' to 3' direction:
- at least one transcriptional effector sequence,
- a TR element encoding an mRNA molecule which is selectively translated in stressed and/or dying cells,
- a nucleotide sequence operably linked to the TR element, which is a first open reading frame (ORF) sequence and encodes a polypeptide or a fragment thereof and is co-translated with the TR element, and
- a polyadenylation sequence, herein referred to as the TR expression cassettes.

The first ORF sequence can be selected from a reporter gene, cytotoxic tumor suppressor gene, toxin gene, pro-drug activating gene and proapoptotic gene.

In one embodiment, the transcriptional effector sequence is a promoter.

In another aspect, the TR expression cassettes can contain a second ORF sequence, which is situated 5' to the TR sequence and is independently translated. The second ORF sequence can be selected from the same sequences as the first ORF.

It is another aspect of the present technology to provide mammalian cells transformed with a TR expression cassette. Preferably the mammalian cells are embryonic stem (ES) cells.

In still another aspect, the present technology provides methods for determining toxicity of a substance. One such method comprises (a) contacting the mammalian cells transformed with a TR expression cassette, wherein the first ORF sequence encodes a reporter polypeptide; and (b) detecting presence or measuring levels of the reporter polypeptide, wherein the presence or an increase in the level of said reporter polypeptide, compared to control cells that are (i) not exposed to said substance or (ii) not transfected is indicative of the toxicity of the substance. Another method for determining toxicity of a substance comprises (a) transfecting or transducing a mammalian cell or stably transforming a mammalian cell line with a TR expression cassette wherein the first ORF sequence encodes a reporter polypeptide; (b) contacting transfected cells from (a) with the substance; and (c) detecting presence or measuring levels of the reporter polypeptide, wherein the presence or an increase in the level of said reporter polypeptide, compared to control cells that are (i) not exposed to said substance or (ii) not transfected/transduced is indicative of the toxicity of the substance.

It is yet another aspect of the present technology to provide a kit, which includes either a TR expression cassette or mammalian cells transformed with such expression cassette, and instructions for use.

In another aspect, the present technology provides a transgenic non-human animal, which has a TR expression cassette stably integrated into its genome. The preferred transgenic animal is a mouse.

In still another aspect, the present technology provides a method for killing a target cell by transforming said cell with the TR expression cassette, wherein the first ORF sequence is selected from a cytotoxic tumor suppressor, toxin gene, pro-drug activating gene or proapoptotic gene.

DRAWINGS

Figure 1B:
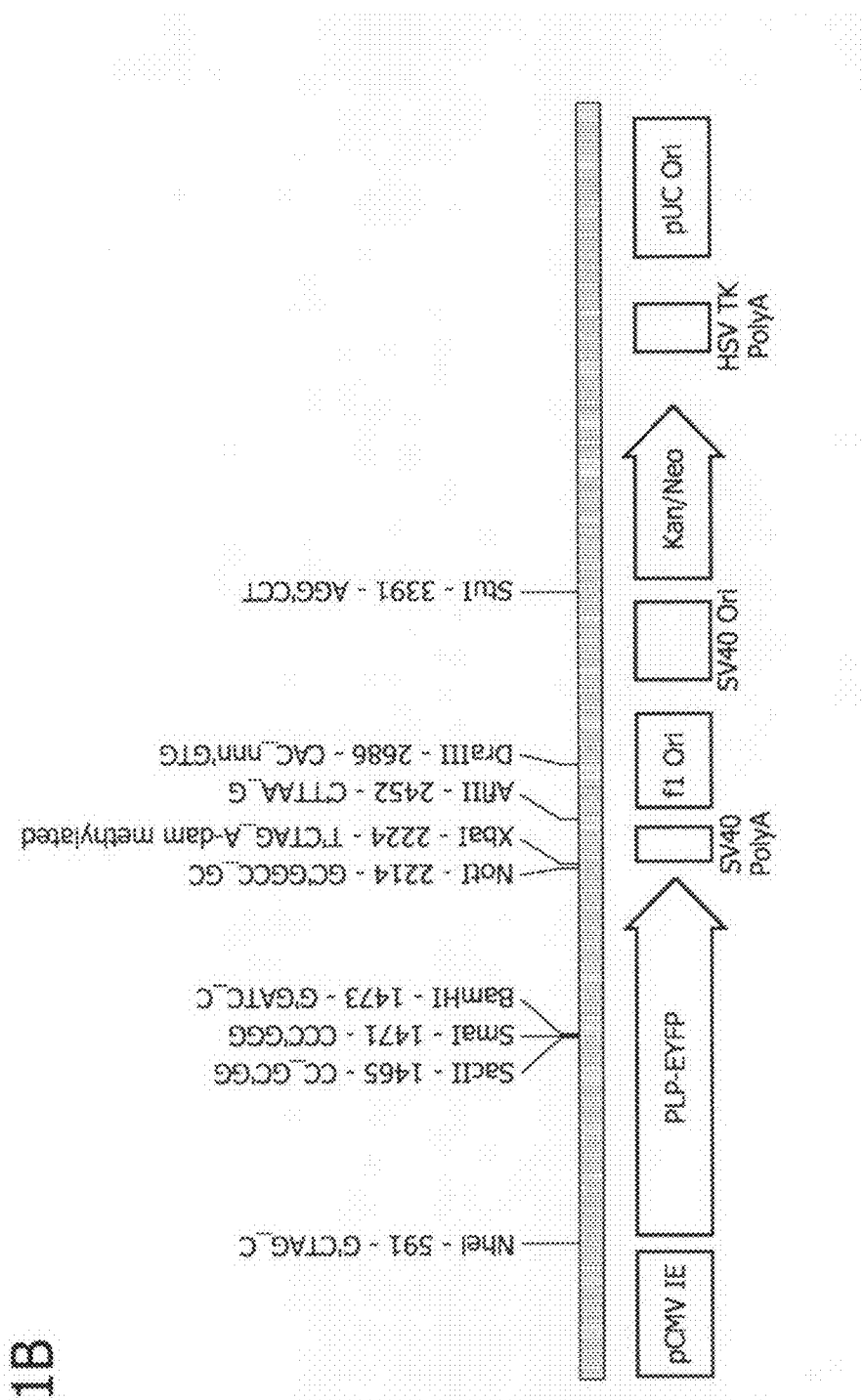
Figure 1C:
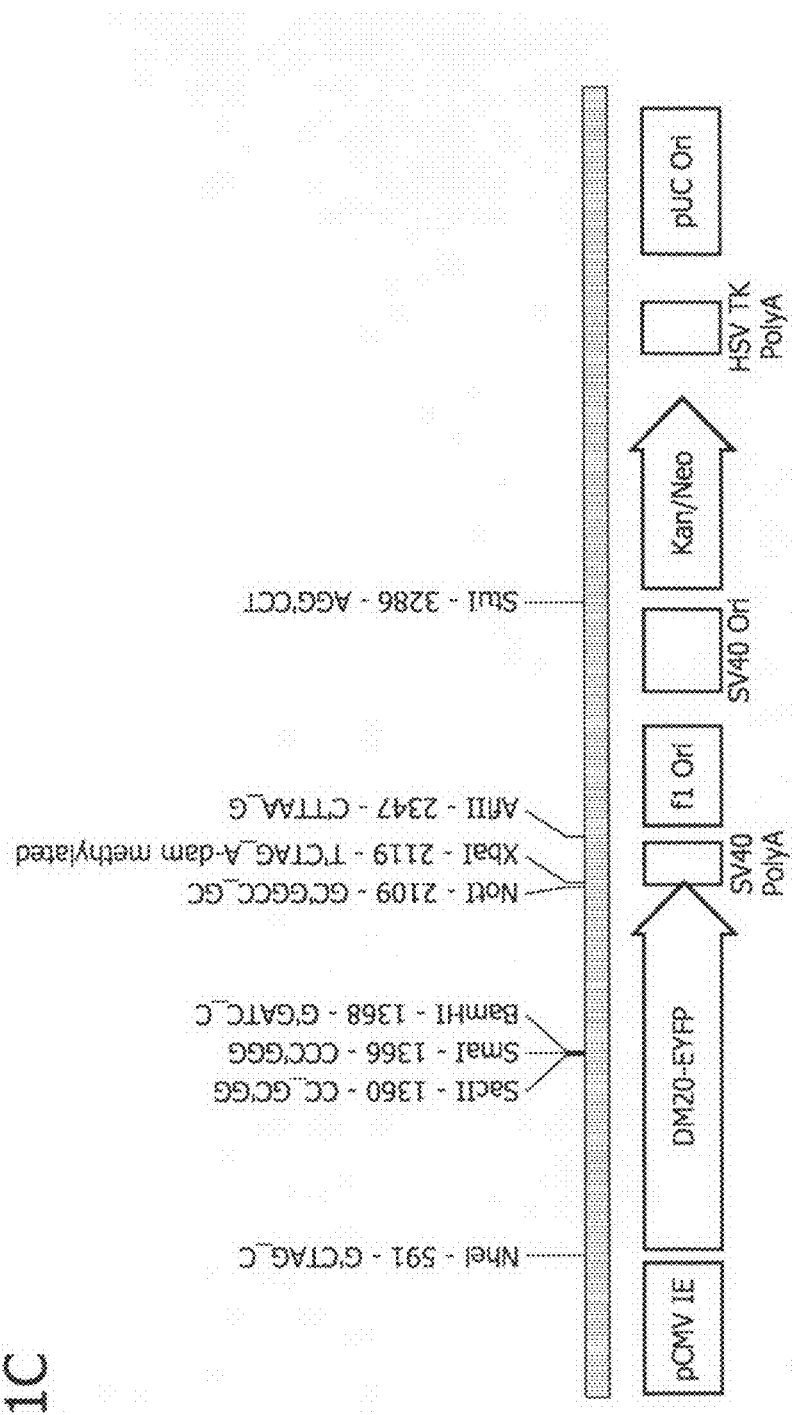

FIG. 1 is a schematic drawing showing the parental plasmids used to produce the pTR-ORF vectors. FIG. 1A shows a restriction map of the pEYFP-N1 vector. FIG. 1B shows the pPLPeyfp expression vector used to express the PLP isoform of the proteolipid protein (PLP) as a fusion protein with the Enhanced Yellow Fluorescence Protein (EYFP). FIG. 1C shows the pDM20eyfp expression vector that expresses the DM20 proteolipid protein isoform as a fusion protein with the EYFP protein. Functional plasmid elements (restriction enzyme sites, origins of replication, open reading frames, etc.) are represented with vertical lines, boxes and arrows as needed.

Figure 2A:
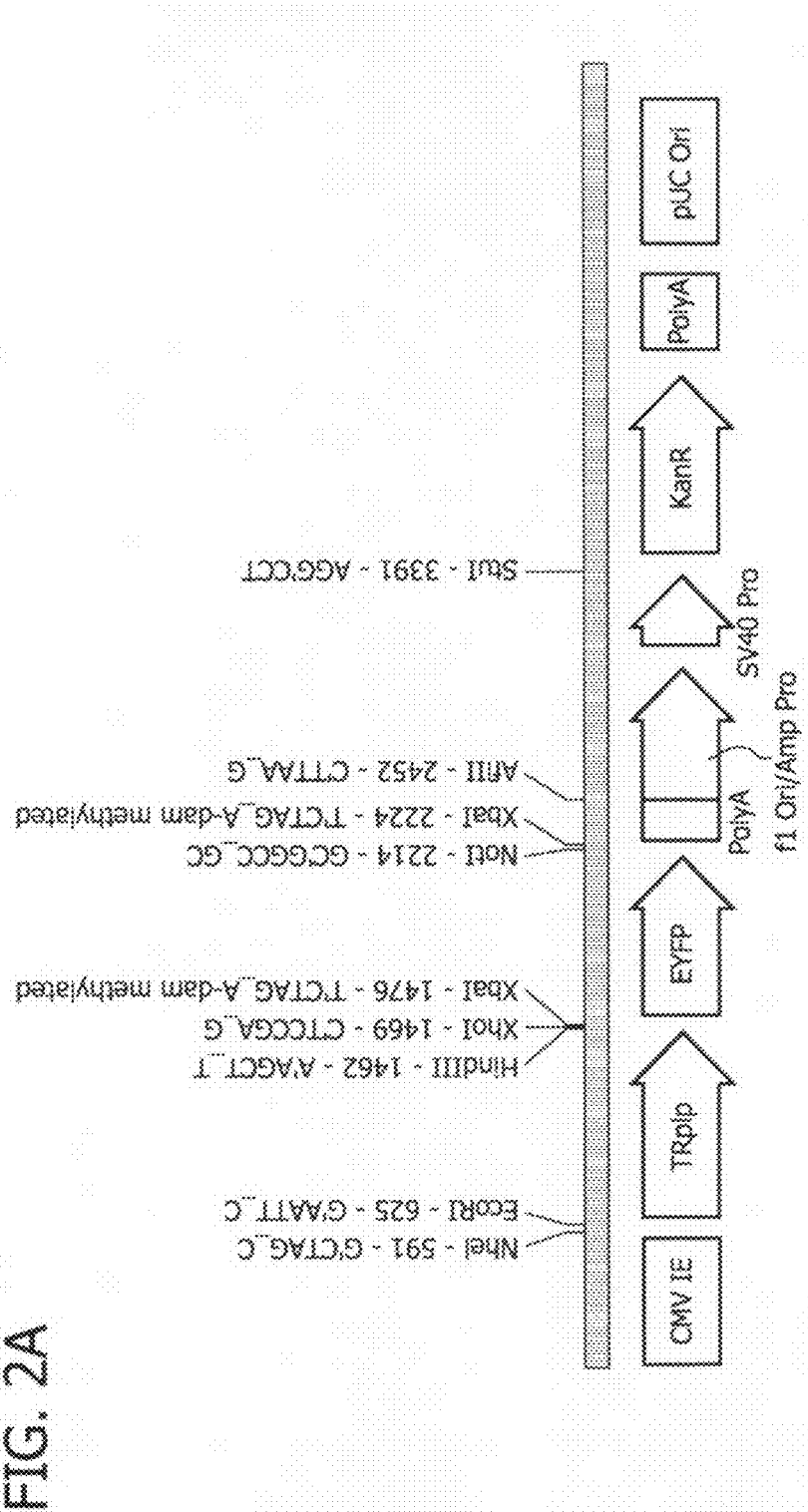
Figure 2B:
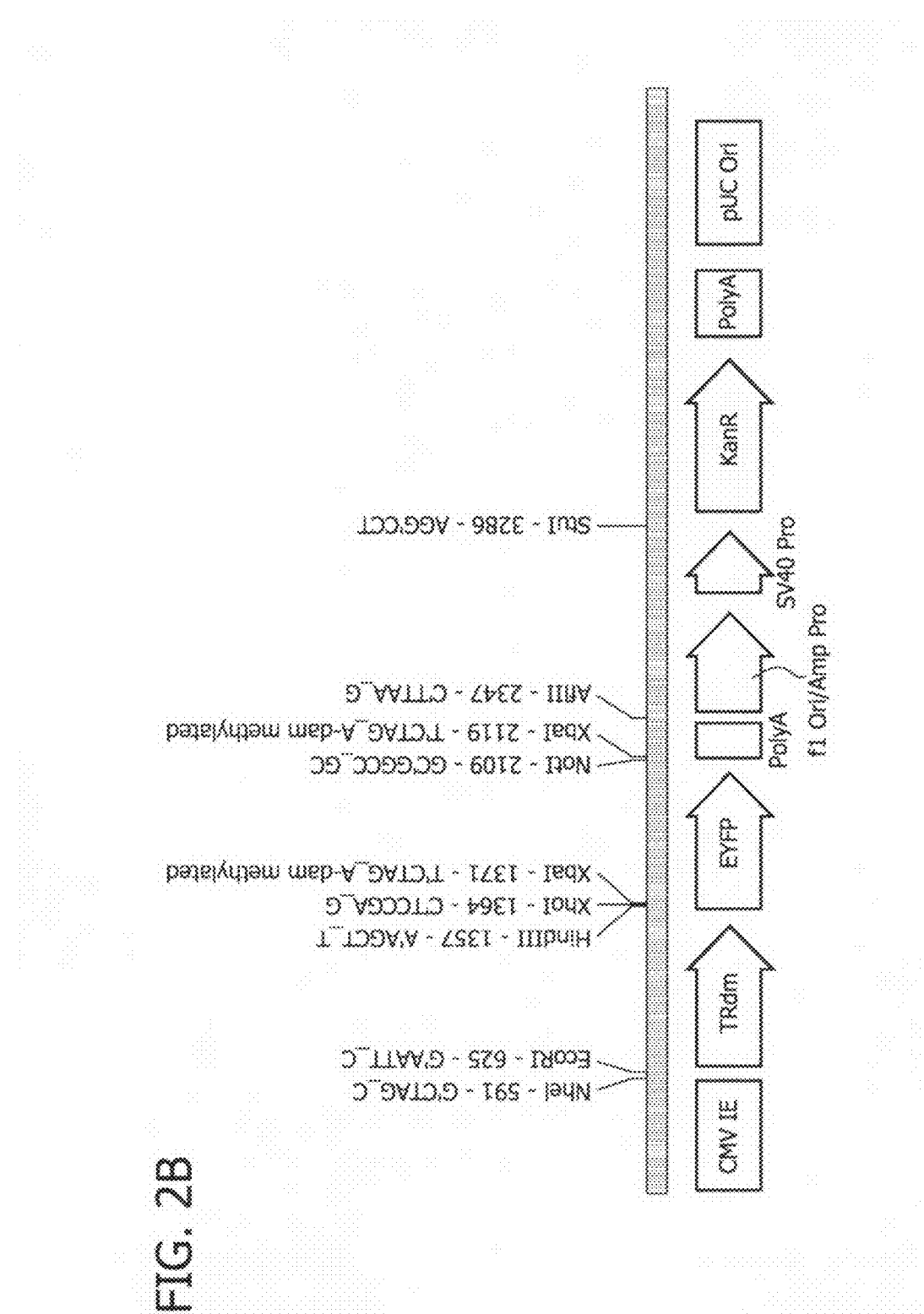
Figure 3A:
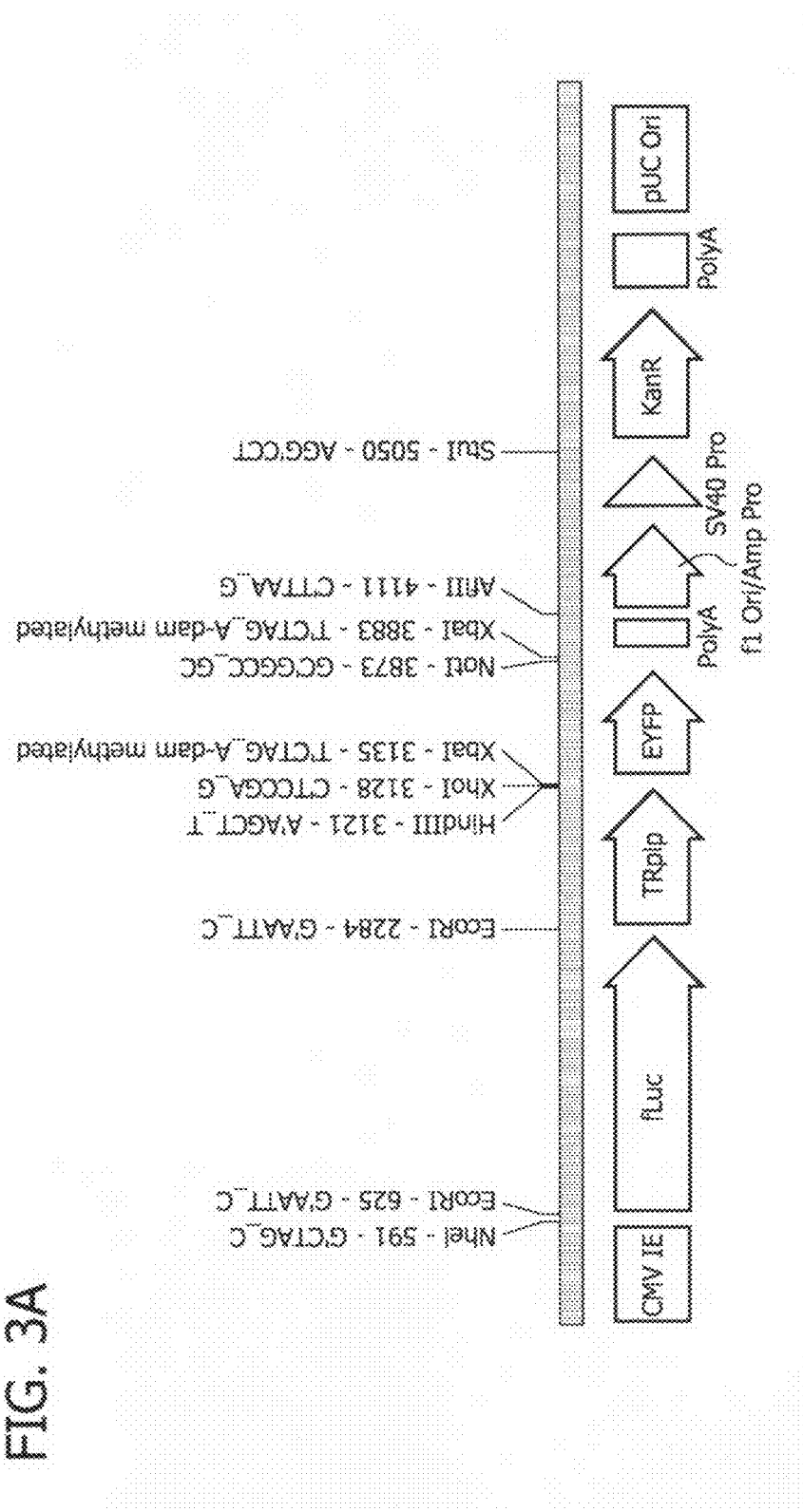
Figure 3B:
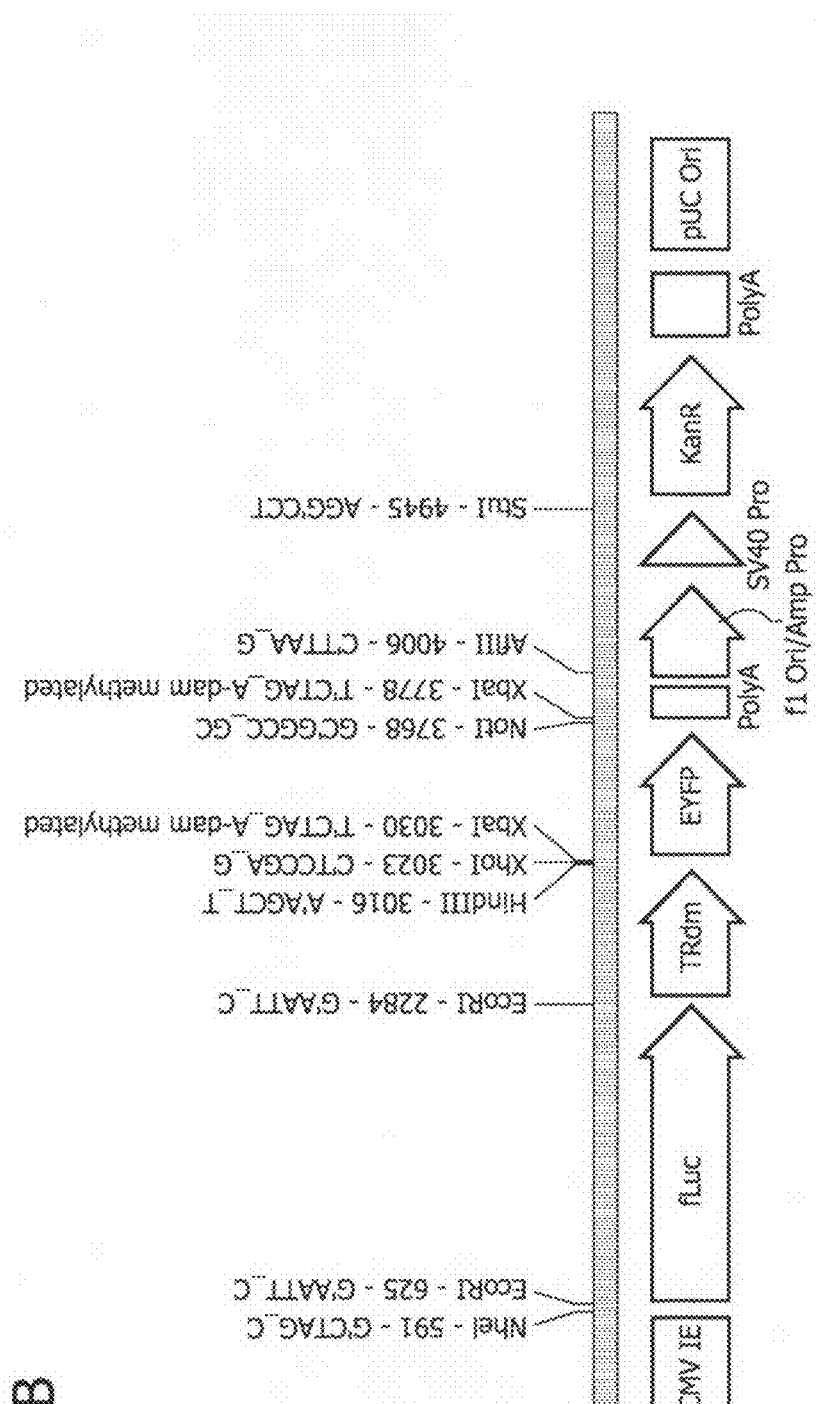
Figure 3C:
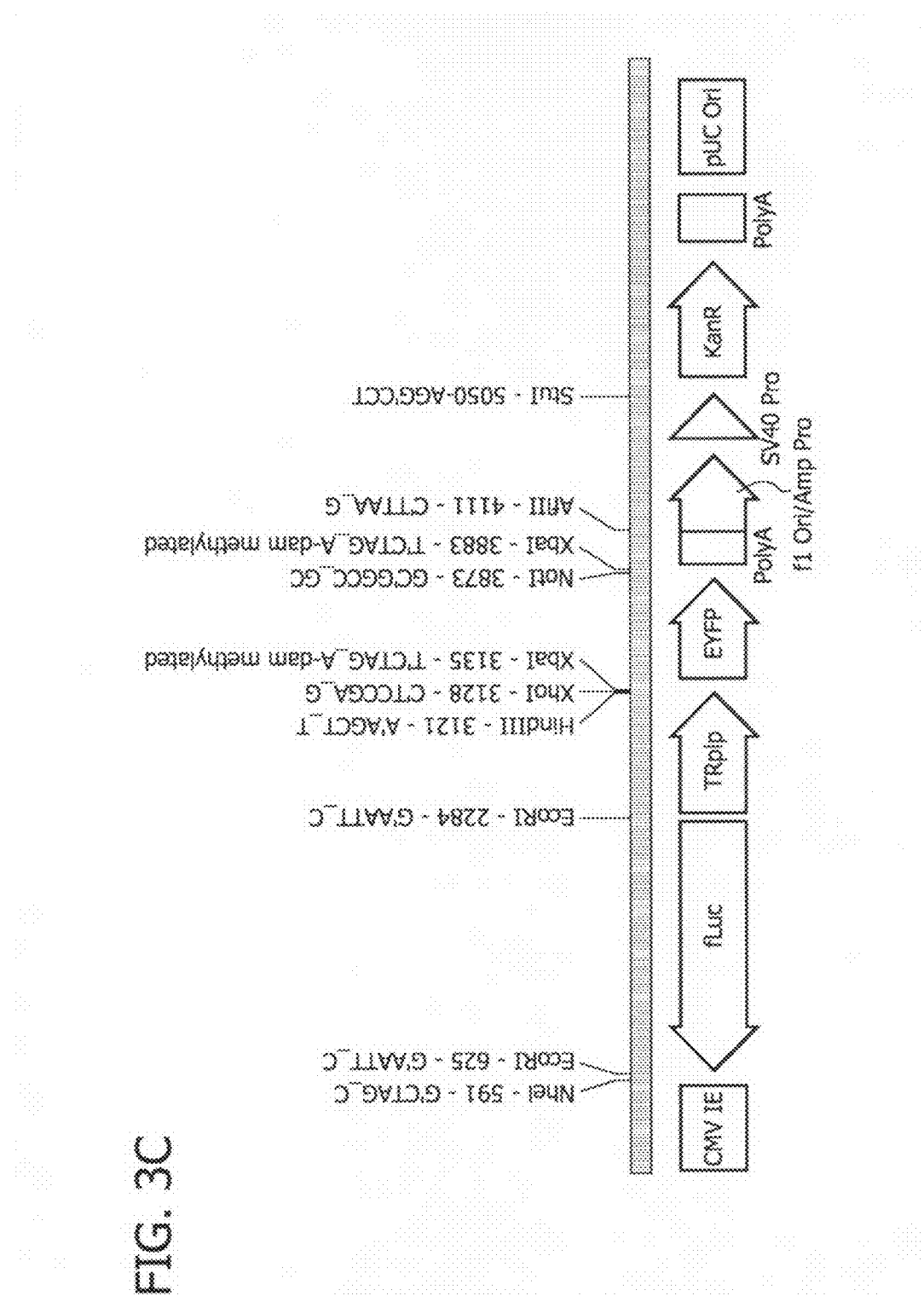
Figure 3D:
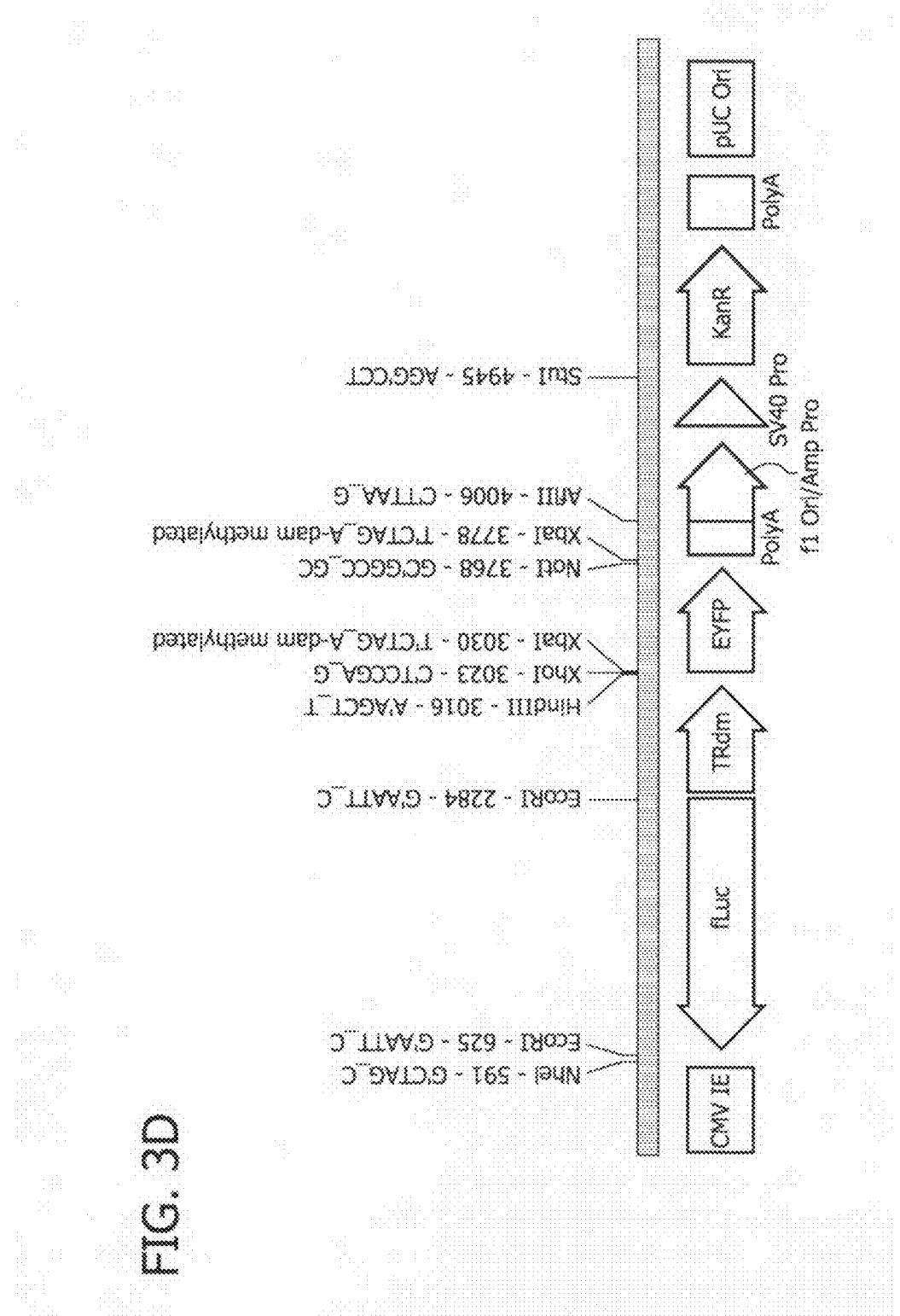

FIG. 2 shows schematic examples of the monocistronic pTR-EYFP expression vectors. FIG. 2A shows a map of the pTR$_{plp}$-EYFP vector. The TR-ORF cassette in this vector is composed of the CMV IE transcriptional promoter, the TR element derived from the PLP isoform cDNA sequence, the EYFP open reading frame and the SV40 polyadenylation signal. FIG. 2B shows a map of the pTR$_{dm}$-EYFP vector. This TR-ORF cassette is similar to FIG. 2A except the TR element is derived from the DM20 isoform cDNA sequence.

FIG. 3 shows schematic representations of the bicistronic pORF-TR-ORF vectors. FIG. 3A shows a map of the pfLuc-TR$_{plp}$-EYFP vector. The bicistronic cassette in this vector is composed of the CMV IE transcriptional promoter, the firefly Luciferase (fLuc) gene in the "sense" orientation relative to the direction of TR transcription, the plp-specific TR element functionally linked to the EYFP ORF and the SV40 polyadenylation signal. Relevant restriction sites and plasmid functional elements are shown. FIG. 3B shows a map of the pfLuc-TR$_{dm}$-EYFP plasmid. FIG. 3C displays a map of the pcuLf-TR$_{plp}$-EYFP vector, in which the fLuc ORF is in an "antisense" orientation in the TR expression cassette. FIG. 3D shows a map for the pcuLf-TR$_{dm}$-EYFP plasmid with an antisense fLuc ORF.

Figure 4:
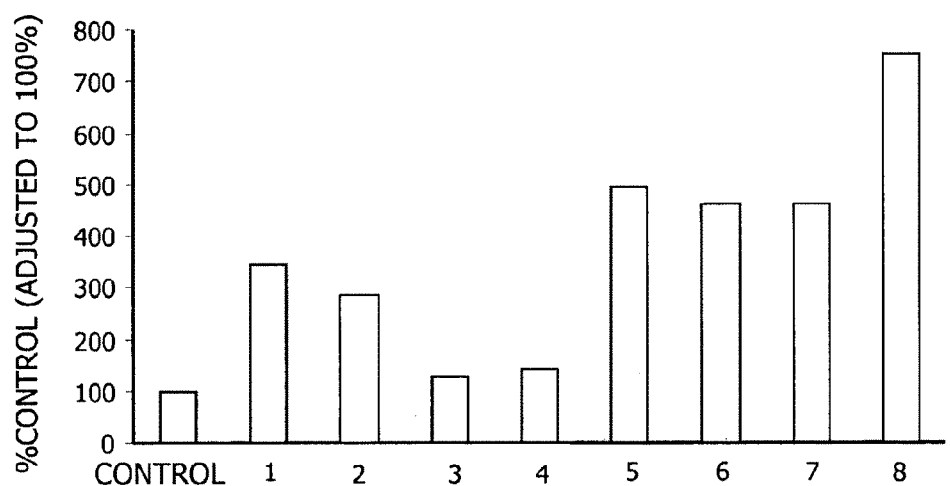

FIG. 4 displays the quantitation of a Western blot analysis showing that cell pools expressing the bicistronic TR cassettes induce EYFP translation after treatment with toxic doses of the calcium ionophore A23187 or the proteasome inhibitor MG132. EYFP protein levels are determined by densitometry and expressed as % of the protein level detected in control HEK293 cells (adjusted to 100%). Cap-independent translation is independent of the orientation of the upstream fLuc ORF (shown as fLuc in the "sense" and cuLf in the "antisense" orientation relative to the TR cassette).

Figure 5A:
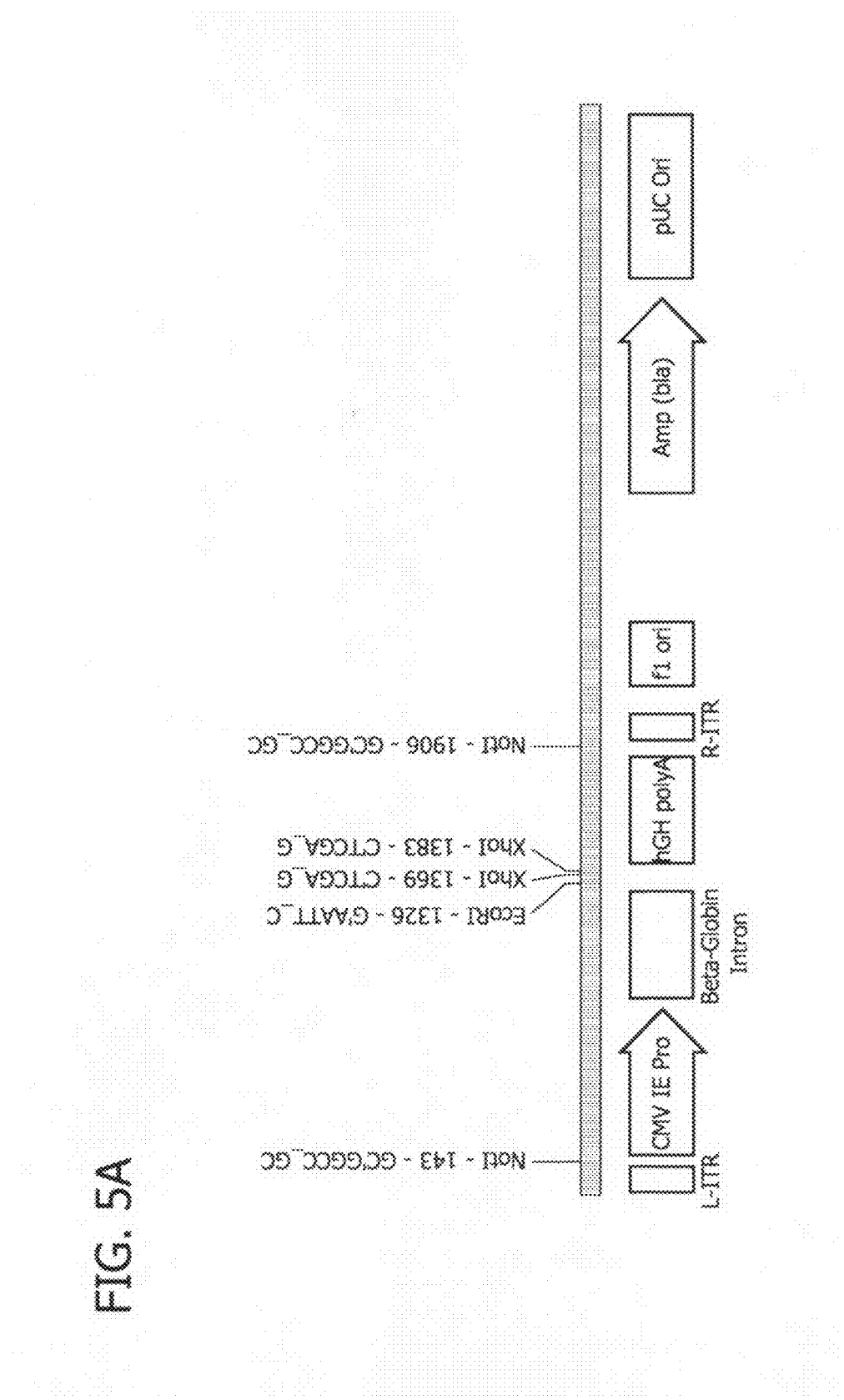
Figure 5B:
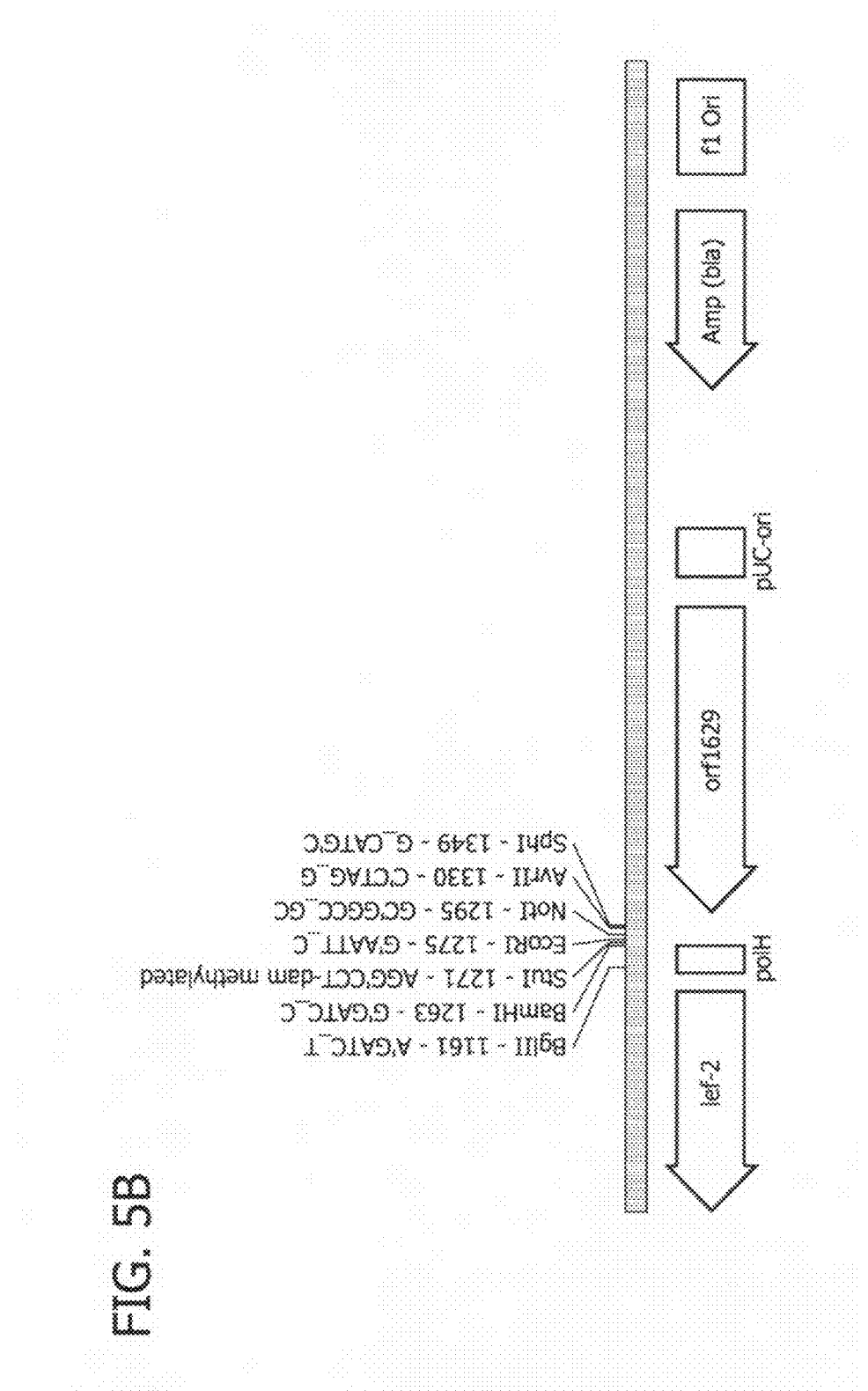

FIG. 5 shows schematic representations of plasmid shuttle vectors that can be used to produce recombinant virus capable of transducing mammalian cells. FIG. 5A shows a map of the pAAV-MCS shuttle vector that can be used to produce recombinant Adeno-associated virus (rAAV) which can transduce mammalian cells in vitro and in vivo. FIG. 5B shows the map of the pBAC-1 shuttle vector that can be used to produce the recombinant Baculovirus (rBAC) virions that transduces mammalian cells to selectively translate the TR-ORF cassettes in stressed and dying cells.

FIG. 6 displays the quantitation of a Western blot analysis showing that cells expressing the monocistronic $TR_{plp/dm}$-fLuc cassettes induce fLuc translation after treatment with toxic doses of the calcium ionophore A23187. fLuc protein levels are determined by densitometry and expressed as % of control HEK293 cells (adjusted to 100%). FIG. 6A shows the fLuc protein levels that are produced by four subclones (#3, 17, 13 and 16) expressing the $TR_{plp}$-fLuc cassette compared to CMV-fLuc and HEK293 cells, as well as a HEK293 $TR_{plp}$-fLuc pool. FIG. 6B shows fLuc protein quantitation for five subclones (#12, 43, 45, 2 and 8) expressing the $TR_{dm}$-fLuc cassette correlated with protein levels in CMV-fLuc, HEK293 and HEK293 $TR_{dm}$-fLuc cells.

Figure 7:
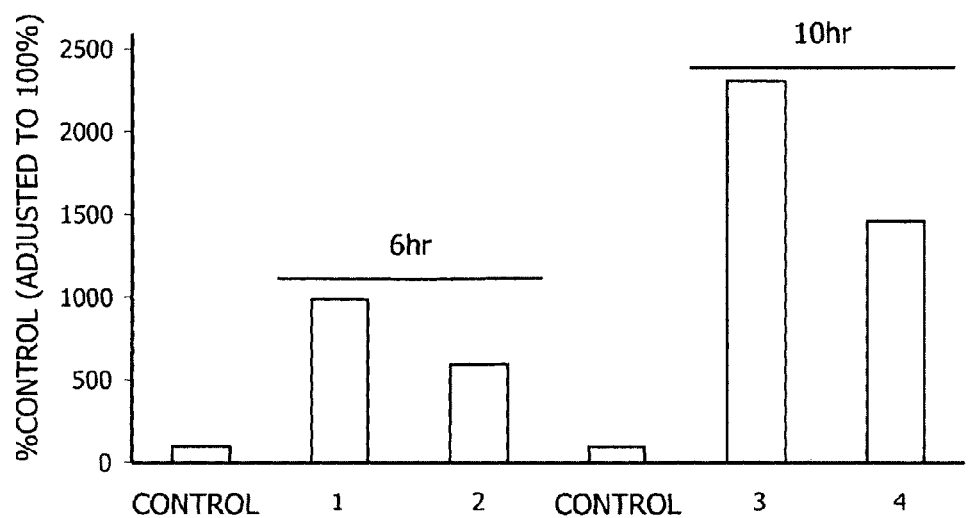

FIG. 7 shows a TR-specific increase in fluorescent HEK293 $TR_{plp/dm}$-EYFP cells at 6 hours and 10 hours post-treatment with a toxic dose of the calcium ionophore A23187. The histogram represents the direct microscopic counts of fluorescent cells. Cell numbers are expressed as the percent of fluorescent cells relative to control HEK293 cells (adjusted to 100%).

Figure 8:
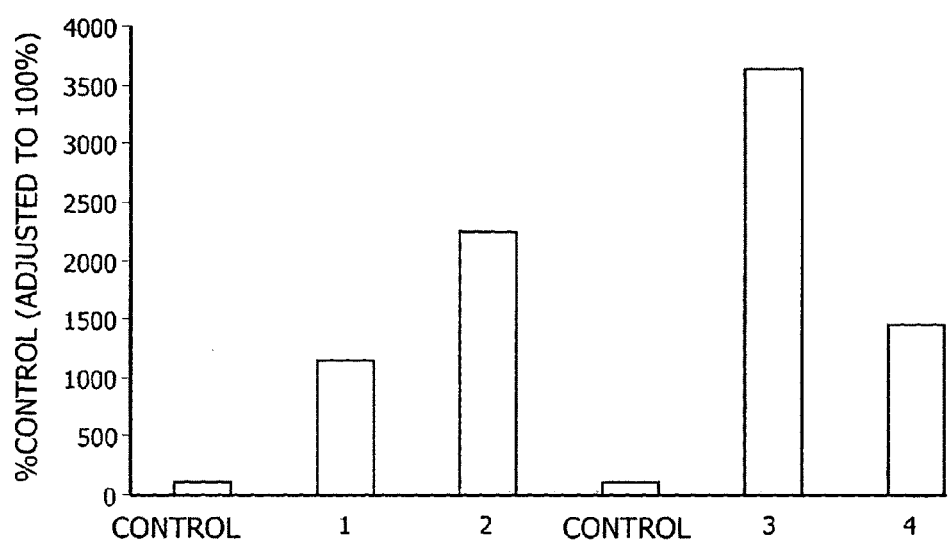

FIG. 8 displays a TR-specific increase in HEK293 $TR_{plp/dm}$-fLuc cells stained by immunofluorescence labeling with an anti-fLuc antibody following treatment with a toxic dose of the calcium ionophore A23187. The histogram represents the direct microscopic count of stained fluorescent cells. Cell numbers are expressed as the percent of fluorescent cells relative to control HEK293 cells (adjusted to 100%).

Figure 9A:
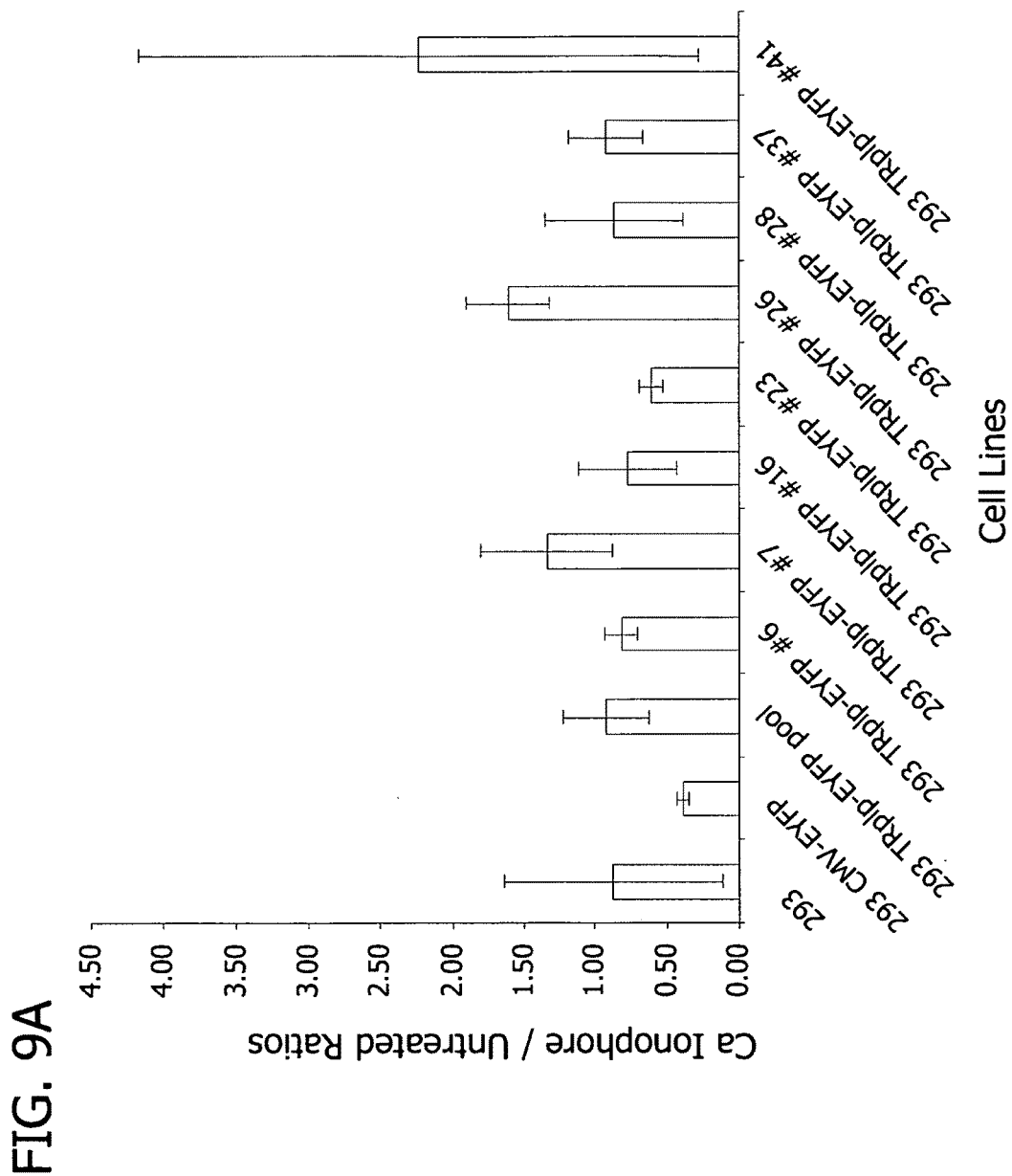
Figure 9B:
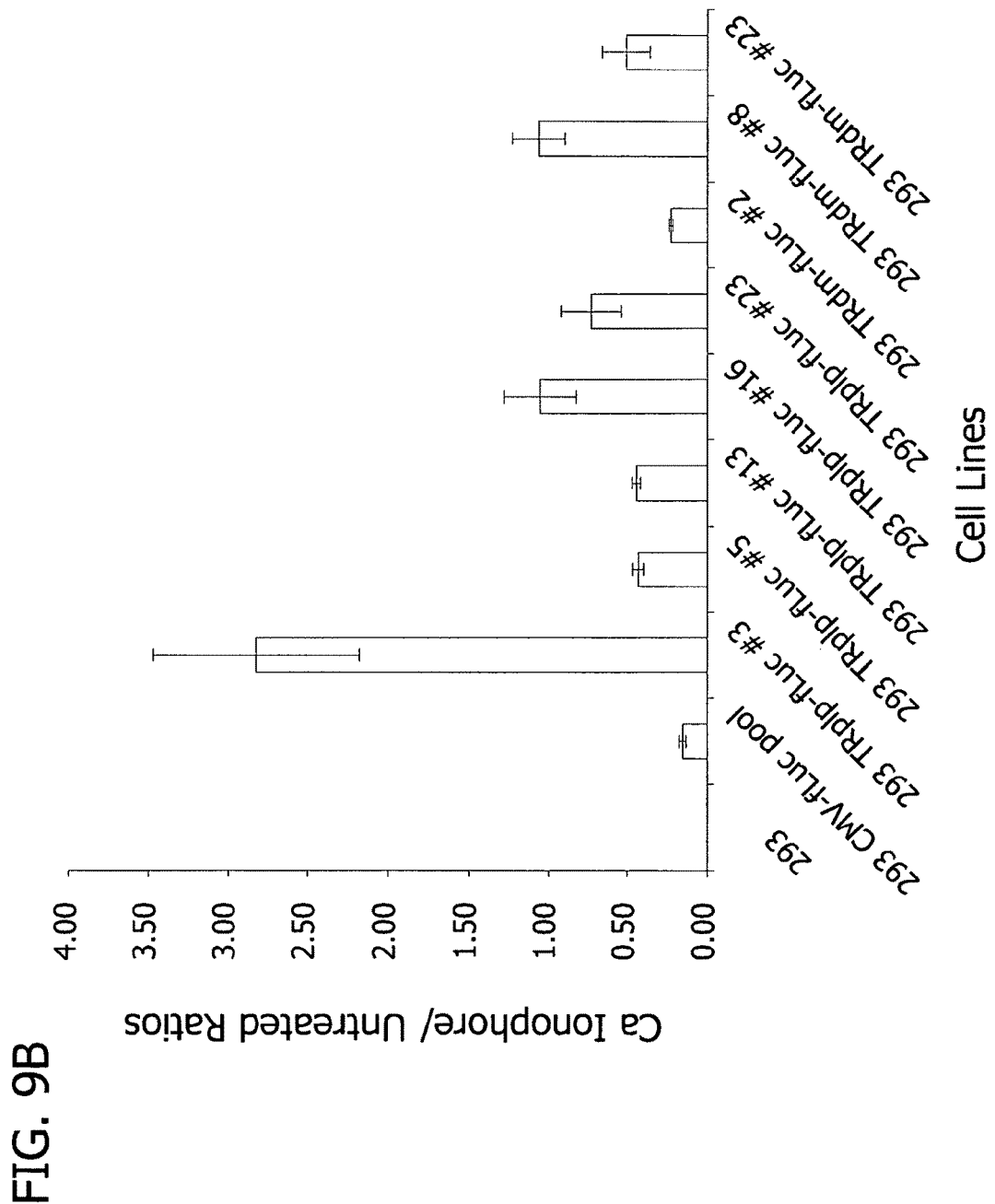
Figure 10A:
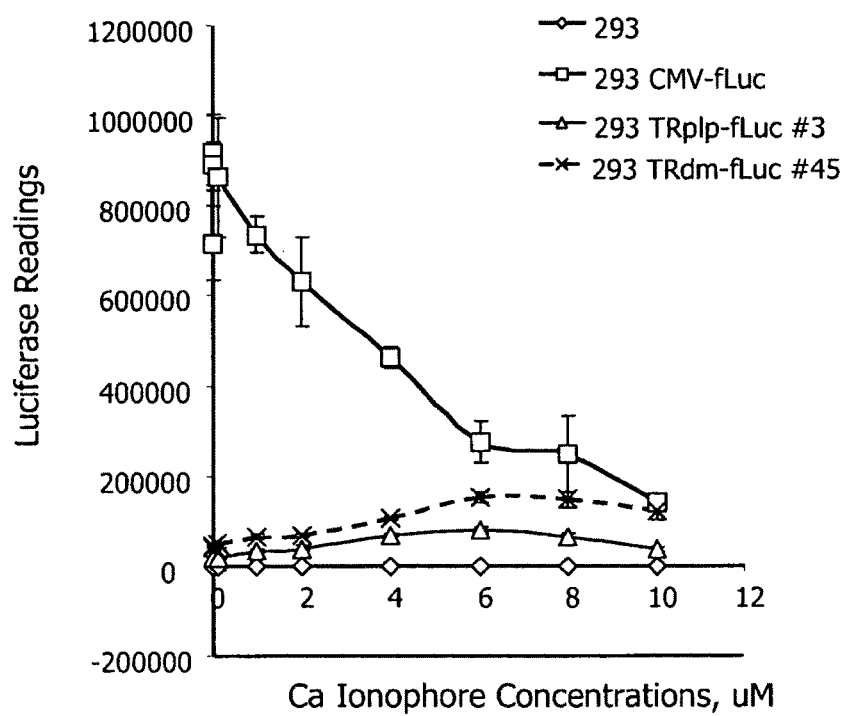
Figure 10B:
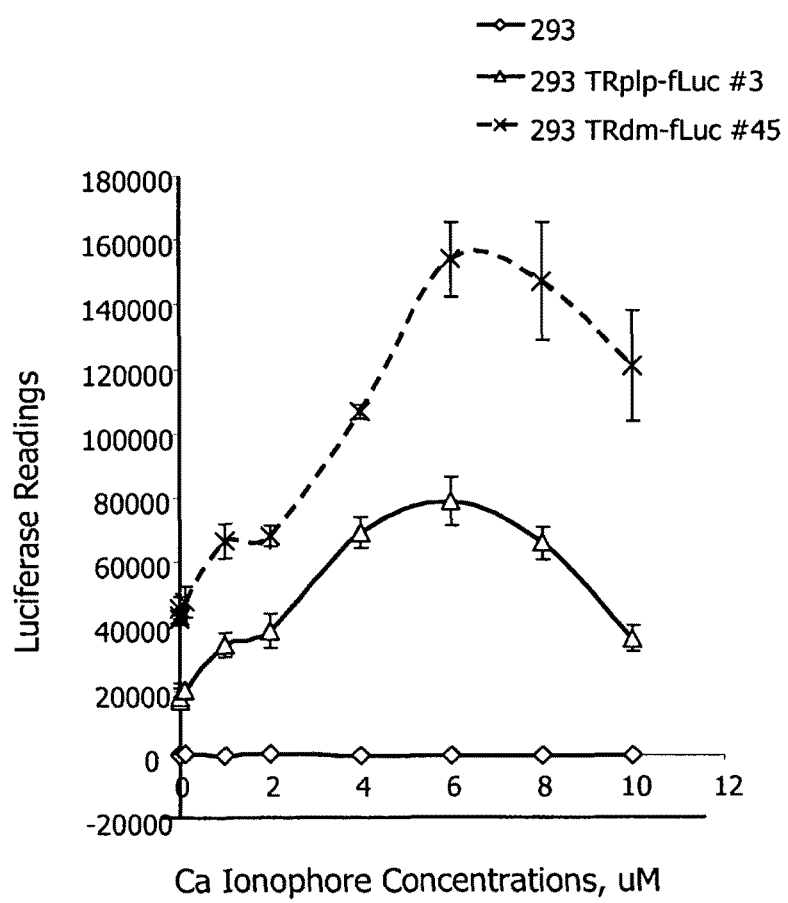
Figure 10C:
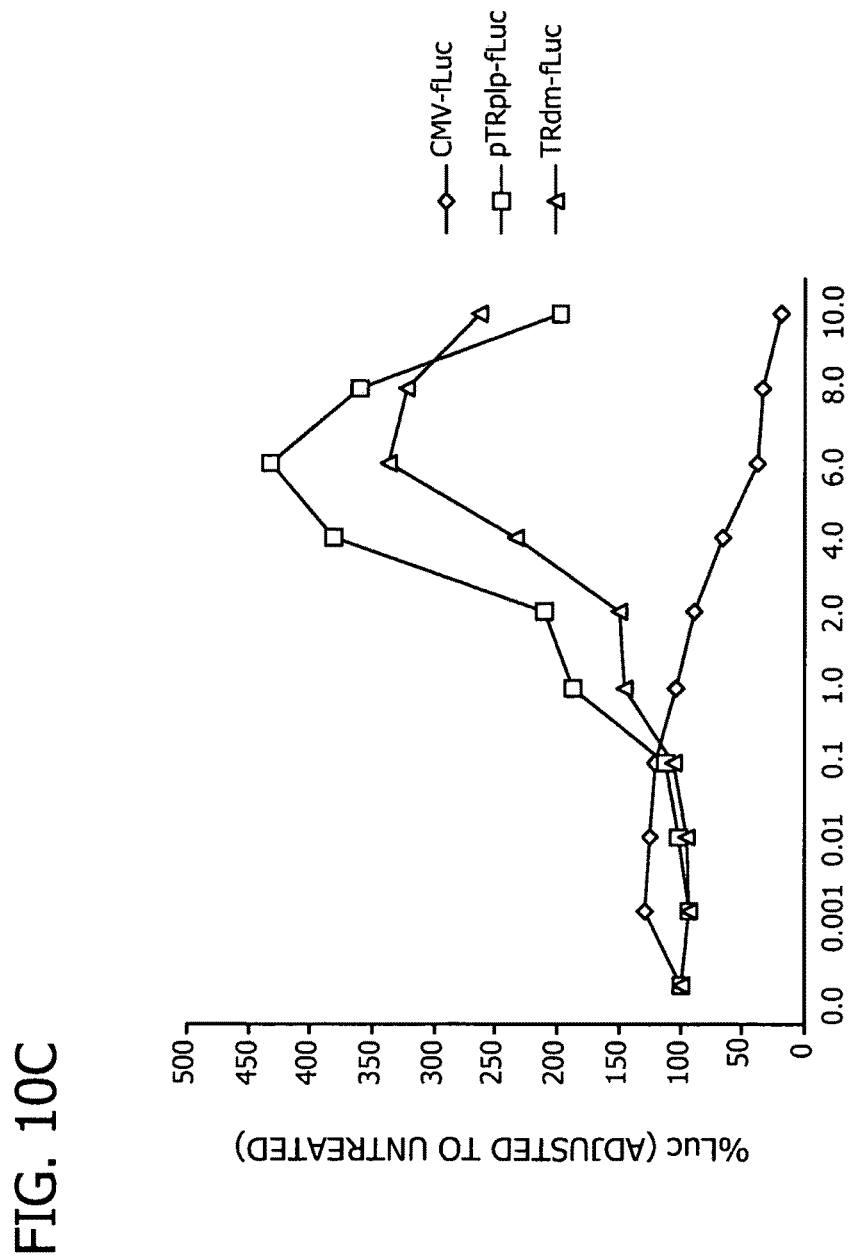
Figure 10D:
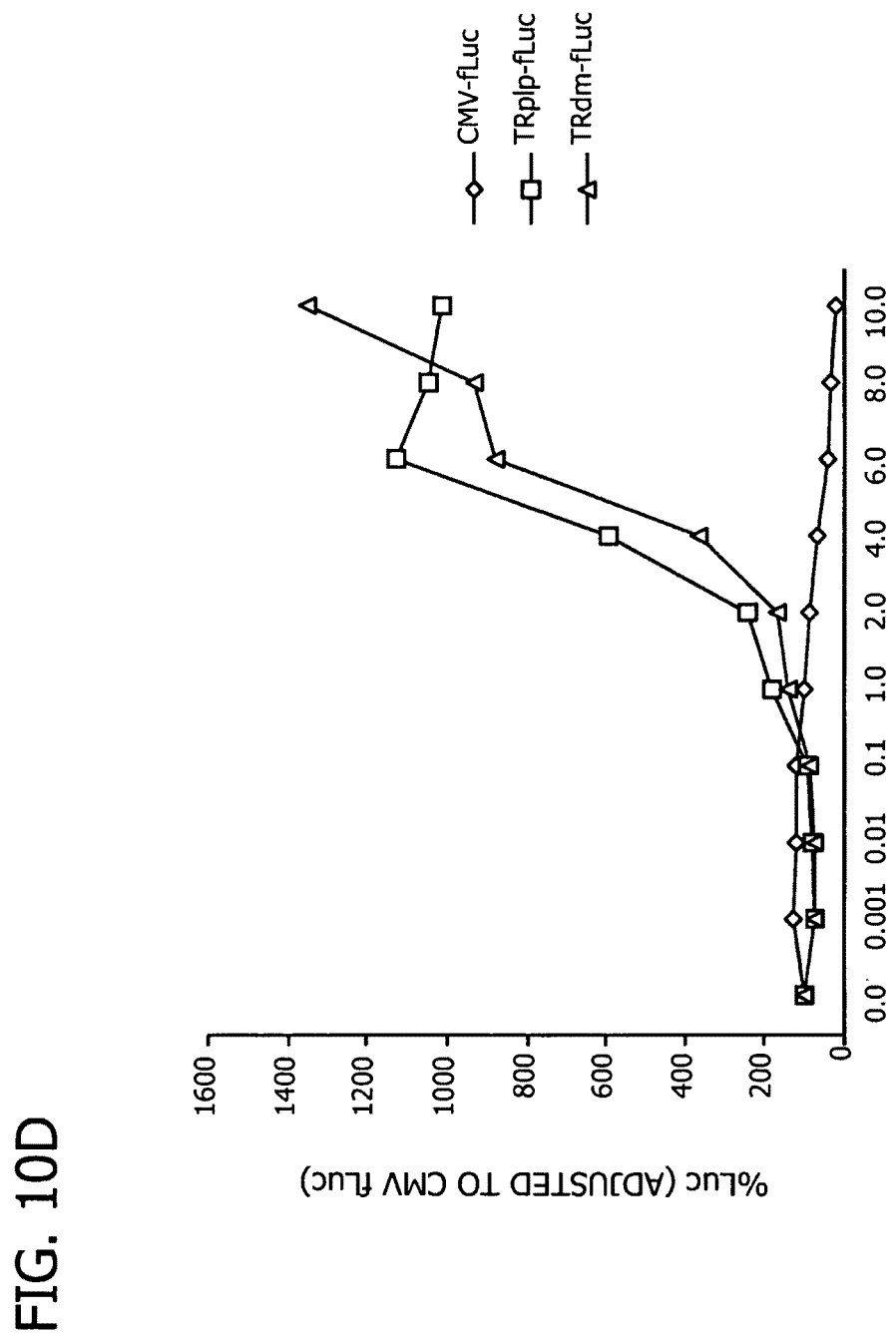
Figure 11A:
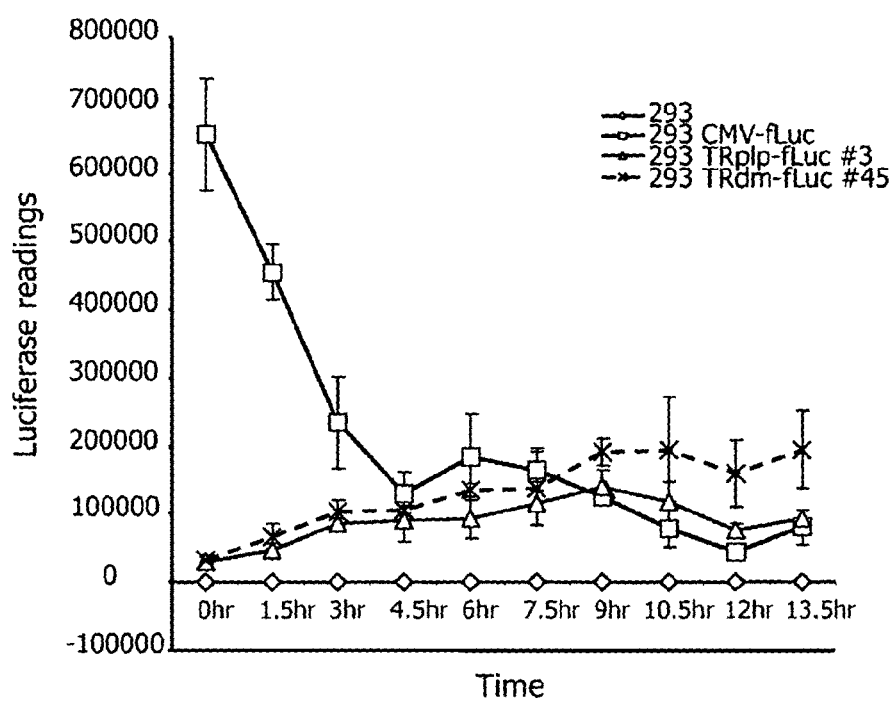
Figure 11B:
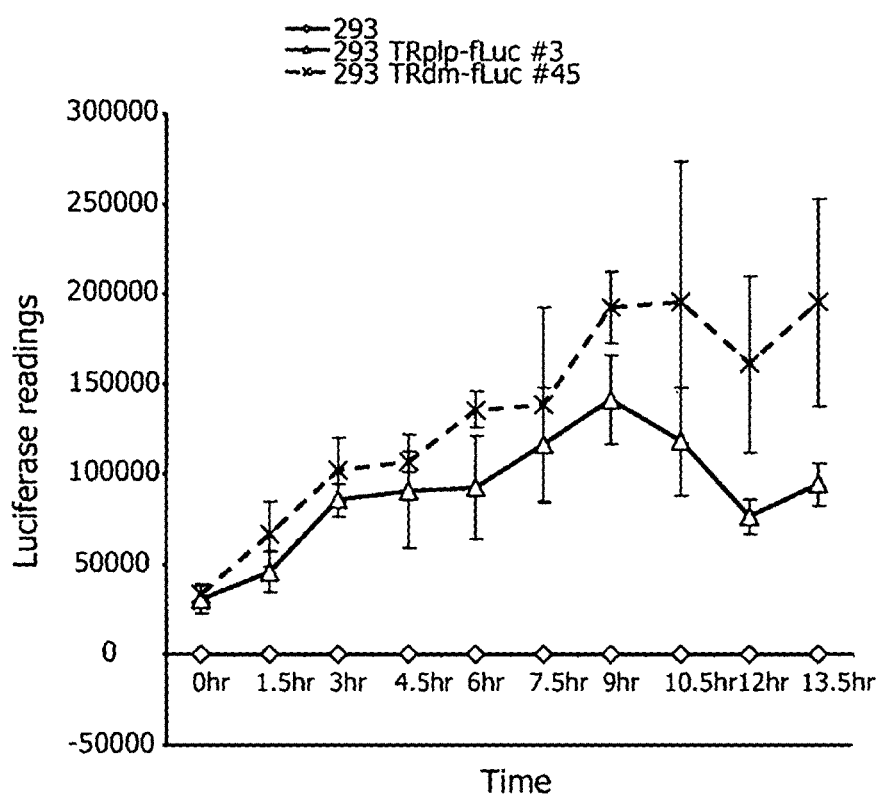
Figure 11C:
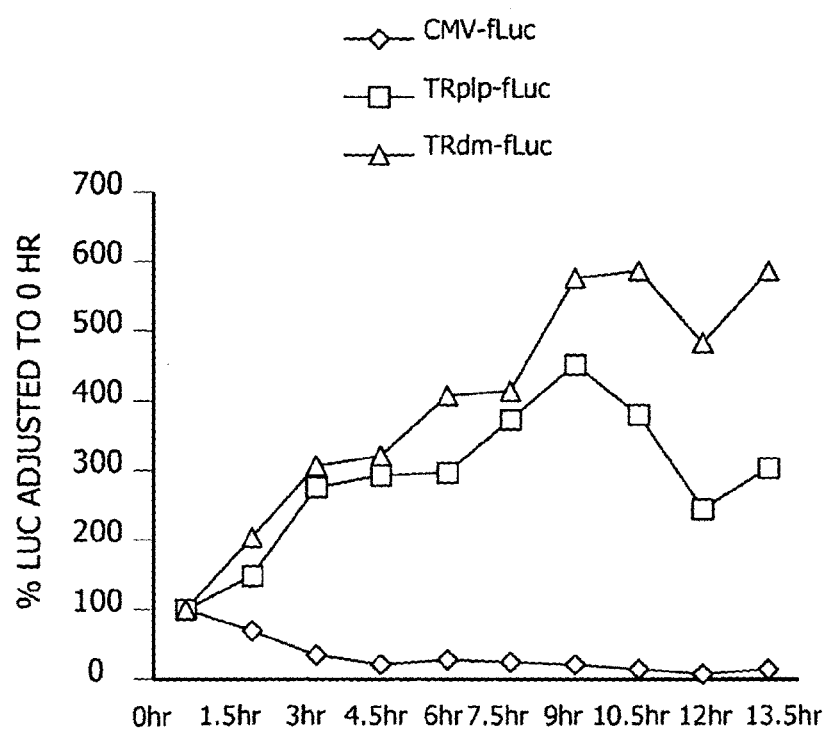
Figure 11D:
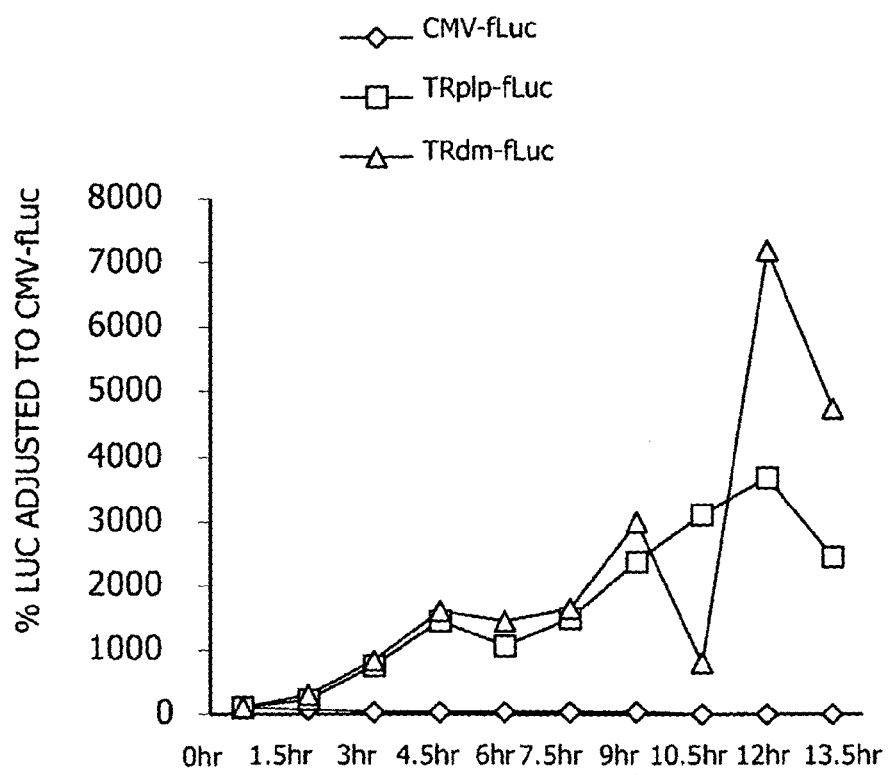

FIG. 9 shows the TR-dependent translation that can be produced by a series of cell lines expressing the $TR_{plp/dm}$-EYFP and $TR_{plp/dm}$-fLuc cassettes following exposure to a toxic dose of the calcium ionophore A23187. The histograms show arbitrary fluorescence or luciferase units that can be obtained by a microplate reader expressed as the ratio of treated to untreated cultures. Ratios in excess of 1.0 are indicative of cells exhibiting TR-dependent translation. FIG. 9A shows the results for eight cell lines expressing the $TR_{plp}$-EYFP cassette compared to HEK293, CMV-EYFP and a $TR_{plp}$-EYFP pool. FIG. 9B shows the results for five cell lines expressing the $TR_{plp}$-fLuc cassette, three cell lines expressing the $TR_{dm}$-fLuc cassette compared to a CMV-fLuc and HEK293 controls.

FIG. 10 shows a TR-dependent dose response that can be produced by cell lines expressing the $TR_{plp/dm}$-fLuc cassettes following exposure to a toxic dose of the calcium ionophore A23187. FIG. 10A shows a chart of arbitrary luminescence units that can be obtained by a microplate reader for HEK293, HEK293 CMV-fLuc, HEK $TR_{plp}$-fLuc (subclone #3) and HEK293 $TR_{dm}$-fLuc (subclone #45) cells after culture in increasing toxin concentrations. FIG. 10B shows only the HEK293 and $TR_{plp/dm}$-fLuc results to emphasize the dose response curve which peaks at 6 μM. FIG. 10C shows a chart that expresses arbritary luciferase readings as the % of luciferase activity in untreated cells. This shows the change in cap-dependent translation that can be produced by the CMV-fLuc cells to the increase in cap-independent luciferase activity exhibited by the TR-ORF cells; however, the shape of the dose response curve is unchanged. FIG. 10D shows the arbitrary luciferase readings as the ratio of the reading to CMV-fLuc cells. This comparison emphasizes the sharp decline in CMV-fLuc activity at high doses and reduces the apparent decline in TR-dependent translation at higher toxin doses.

FIG. 11 shows a TR-dependent temporal response that can be produced by cell lines expressing the $TR_{plp/dm}$-fLuc cassettes following exposure to a toxic dose of the calcium ionophore A23187. FIG. 11A shows a chart of arbritary luciferase readings that can be obtained by a microplate reader for HEK293, HEK293 CMV-fLuc, HEK $TR_{plp}$-fLuc (subclone #3) and HEK293 $TR_{dm}$-fLuc (subclone #45) cells after culture with a toxic dose of the calcium ionophore A23187 as a function of increasing time. FIG. 11B is a chart of HEK293 and $TR_{plp/dm}$-fLuc results that show the increase in luciferase activity observed by 1.5 hr post-treatment. FIG. 11C shows a chart that expresses arbitrary luciferase readings as the % of luciferase activity at 0 hr post-treatment. FIG. 11D shows the arbitrary luciferase readings as the ratio to the CMV-fLuc cells.

Figure 12:
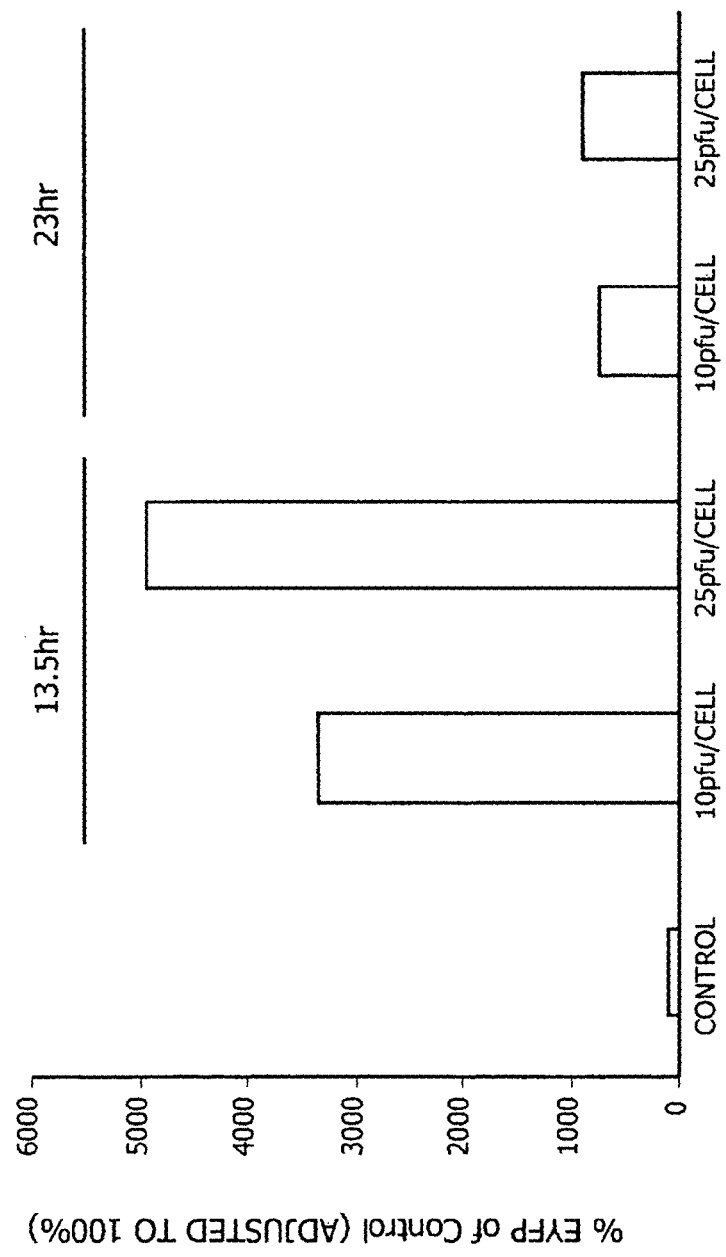

FIG. 12 is a histogram showing the ability of rBAC $TR_{dm}$-EYFP virions to transduce HT1080 cells and exhibit TR-dependent translation in stressed and dying cells. Cells transduced with 10 pfu/cell or 25 pfu/cell rBAC virions are cultured in a toxic concentration of the calcium ionophore A23187 for 13.5 hours or 23 hours. Fluorescent cells are counted microscopically and expressed as the % of control HEK293 cells (infected but not treated with toxin).

Figure 13:
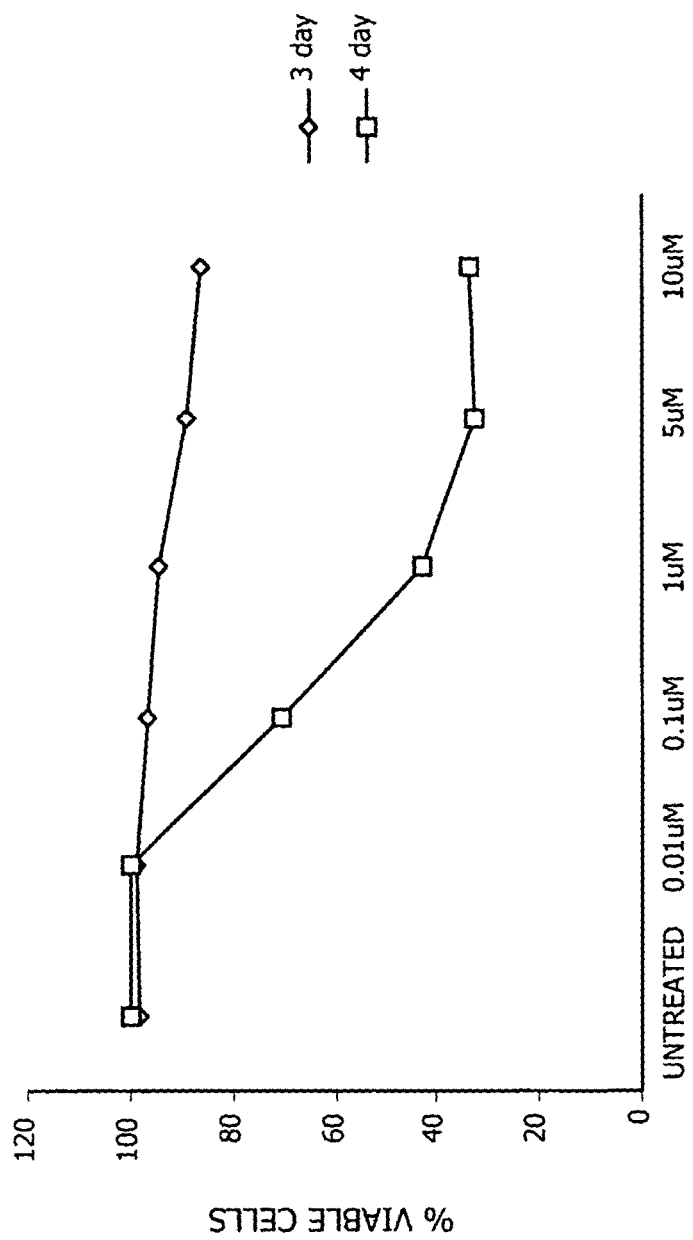

FIG. 13 is a chart showing the ability of the $TR_{plp}$-TKsr39 cell pool to respond to the pro-drug ganciclovir and induce cell death. HEK293, HEK CMV-EYFP and HEK293 $TR_{plp}$-TKsr39 cells are cultured in various concentrations of ganciclovir for 3 or 4 days. Cell viability is determined by the Trypan blue exclusion assay and cell numbers expressed as % viable cells. In contrast to the HEK293 and HEK CMV-EYFP cultures that show no decrease in cell viability at any pro-drug concentration or timepoint, the $TR_{plp}$-TKsr39 cells display reduced viability after 3 days in ganciclovir supplemented medium. By 4 days, the $TR_{plp}$-TKsr39 cells show significant cell death and a dose dependent reduction in cell viability.

FIG. 14 is a sequence comparison table of C-terminal sequences of myelin proteolipid proteins from a variety of vertebrates, taken from the following NCBI Genbank numbers: (1) P60201 *Homo sapiens* SEQ ID NO: 41, (2) Q5R6E6 *Pongo pygmaeus* (orangutan) SEQ ID NO: 42, (3) XP_001140782 *Pan troglodytes* (chimpanzee) SEQ ID NO: 43, (4) XP_001088537 *Macaca mulatta* (rhesus monkey) SEQ ID NO: 44, (5) Q8HXW7 *Macaca fascicularis* (crab-eating macaque) SEQ ID NO: 45, (6) NP_999139 *Sus scrofa* (pig) SEQ ID NO: 46, (7) NP_035253 *Mus musculus* (mouse) SEQ ID NO: 47, (8) NP_112252 *Rattus norvegicus* (rat) SEQ ID NO: 48, (9) XP_001374483 *Monodelphis domestica* (opossum) SEQ ID NO: 49, (10) P47789 *Oryctolagus cuniculus* (rabbit) SEQ ID NO: 50, (11) CAA08909 *Bos taurus* (cattle) SEQ ID NO: 51, (12) 39025 *Canis familiaris* (dog) SEQ ID NO: 52, (13) CAA43839 *Gallus gallus* (chicken) SEQ ID NO: 53, (14) P47790 *Taeniopygia guttata* (zebra finch) SEQ ID NO: 54, (15) AAW79015 *Gekko japonicus* (gecko lizard) SEQ ID NO: 55, (16) CAA79582 *Xenopus laevis* (frog) SEQ ID NO: 56, and (17) BAA84207 *Latimeria chalumnae* (coelacanth) SEQ ID NO: 57. Insertion mutations present in some species are shown double-underlined.

Figure 15B:
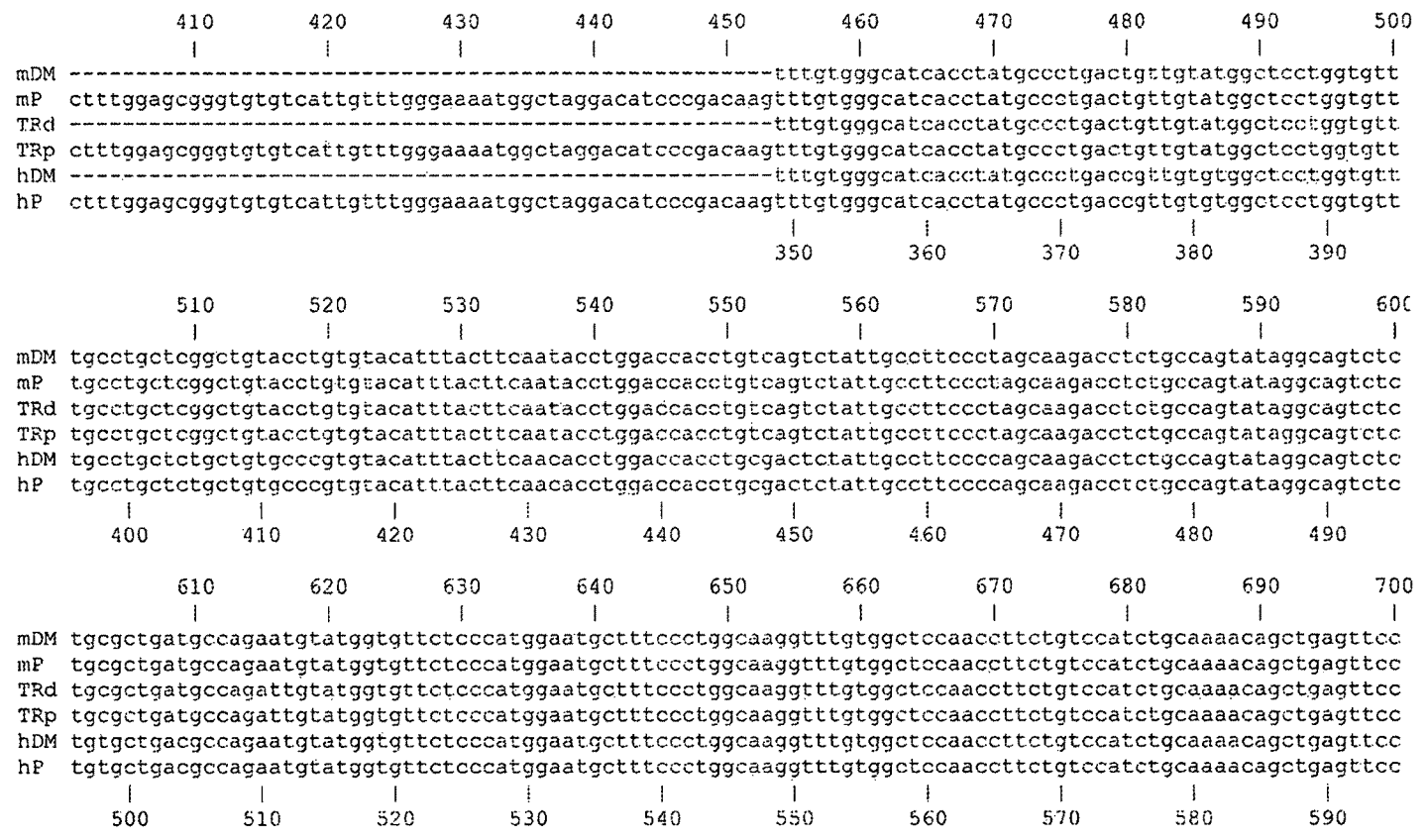

FIG. 15, i.e. 15A-15C, is a sequence alignment chart of murine and human PLP/DM20 coding sequences and TR elements hereof. Key: mDM =murine DM20 cDNA SEQ ID NO: 58; mP=murine PLP cDNA SEQ ID NO: 59; TRd=TRdm [SEQ ID NO: 1]; TRp=TRplp [SEQ ID NO: 2]; hDM=human DM20 SEQ ID NO: 60; and hP=human PLP SEQ ID NO: 61. Because DM20 sequences omit part of the sequence present in full-length PLP coding sequences, the numbering of DM20 sequences in FIG. 15 is discontinuous and, after the omitted segment, DM20 numbering is shown continuing below the aligned sequences. In describing sequences herein with reference to FIG. 15, in some cases dual numbering for PLP/DM20 nucleotide positions is utilized, e.g., residue 560/455; this usage refers to PLP and DM20 numbering in the alternative, with PLP numbering as shown above the aligned sequences, and DM20 numbering as shown below the aligned sequences. The last expressed codon shown is 'ttc' 829/724 to 831/726.

It should be noted that the figures set forth herein are intended to exemplify the general characteristics of materials and methods among those of the present technology, for the purpose of the description of such embodiments herein. These figures may not precisely reflect the characteristics of any given embodiment, and are not necessarily intended to define or limit specific embodiments within the scope of this technology.

DETAILED DESCRIPTION

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary,") and sub-headings (such as "Expression Cassettes") used herein are intended only for general organization of topics within the disclosure of the present technology, and are not intended to limit the disclosure of the technology or any aspect thereof. In particular, subject matter disclosed in the "Introduction" may include aspects of technology within the scope of one or more inventions, and may not constitute a recitation of prior art. Subject matter disclosed in the "Summary" is not an exhaustive or complete disclosure of the entire scope of the technology or any embodiments thereof.

The citation of references herein does not constitute an admission that those references are prior art or have any relevance to the patentability of the technology disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the present technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific Examples are provided for illustrative purposes of how to make, use and practice the materials and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the terms "comprising," "including," and "having," and their variants, are intended to be non-limiting, such that recitation of items in a list is not to the exclusion of other like items that may also be useful in the materials, compositions, and methods of this technology.

As used herein, the term "about," when applied to the value for a parameter of a composition or method of this technology, indicates that the calculation or the measurement of the value allows some slight imprecision without having a substantial effect on the chemical or physical attributes of the composition or method.

When introducing elements of the present technology or the preferred embodiment(s) thereof, the articles "a," "an," "the," and "said" are intended to mean that there are one or more of the elements.

The term "cytotoxic gene" refers to a nucleotide sequence which when expressed in a target cell induces death of the cell by lysis, apoptosis, necrosis or any other mechanism of cell killing.

The term "gene" refers to a nucleic acid (e.g., DNA) sequence that comprises coding sequences necessary for the production of a polypeptide or precursor or RNA (e.g., tRNA, siRNA, rRNA, etc.). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

The term "expression vector" refers to both viral and non-viral vectors comprising a nucleic acid expression cassette.

The term "expression cassette" is used to define a nucleotide sequence containing regulatory elements operably linked to a coding sequence that result in the transcription and translation of the coding sequence in a cell.

A "mammalian promoter" refers to a transcriptional promoter that functions in a mammalian cell that is derived from a mammalian cell, or both.

A "mammalian minimal promoter" refers to a 'core' DNA sequence required to properly initiate transcription via RNA polymerase binding, but which exhibits only token transcriptional activity in the absence of any operably linked transcriptional effector sequences.

The phrase "open reading frame" or "coding sequence" refers to a nucleotide sequence that encodes a polypeptide or protein. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

"Operably linked" is defined to mean that the nucleic acids are placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accord with conventional practice.

"Recombinant" refers to the results of methods, reagents, and laboratory manipulations in which nucleic acids or other biological molecules are enzymatically, chemically or biologically cleaved, synthesized, combined, or otherwise manipulated ex vivo to produce desired products in cells or other biological systems. The term "recombinant DNA" refers to a DNA molecule that is comprised of segments of DNA joined together by means of molecular biology techniques.

"Transfection" is the term used to describe the introduction of foreign material such as foreign DNA into eukaryotic cells. It is used interchangeably with "transformation" and "transduction" although the latter term, in its narrower scope refers to the process of introducing DNA into cells by viruses, which act as carriers. Thus, the cells that undergo transfection are referred to as "transfected," "transformed" or "transduced" cells.

The term "plasmid" as used herein, refers to an independently replicating piece of DNA. It is typically circular and double-stranded.

A "reporter gene" refers to any gene the expression of which can be detected or measured using conventional techniques known to those skilled in the art.

The term "regulatory element" or "effector element" refer to a transcriptional promoter, enhancer, silencer or terminator, as well as to any translational regulatory elements, polyadenylation sites, and the like. Regulatory and effector elements may be arranged so that they allow, enhance or facilitate selective production of a mature coding sequence that is subject to their regulation.

The term "vector" refers to a DNA molecule into which foreign fragments of DNA may be inserted. Generally, they contain regulatory and coding sequences of interest. The term vector includes but is not limited to plasmids, cosmids, phagemids, viral vectors and shuttle vectors.

A "shuttle" vector is a plasmid vector that is capable of prokaryotic replication but contains no eukaryotic replication sequences. Viral DNA sequences contained within this replication-deficient shuttle vector direct recombination within a eukaryotic host cell to produce infective viral particles.

The term "substance" as used herein refers to a matter of defined chemical composition. It is used herein interchangeably with the term "compound."

The term "viral vector" refers to a virus which contains foreign genetic material for delivery into cells it infects.

A "replication-deficient" viral vector is incapable of replication in a "wild-type" or otherwise unmanipulated mammalian cell. Production of significant quantities of such viruses requires that a producer cell line be co-transfected with a helper virus or otherwise modified to supply or complement the missing function(s).

A "replication-competent" viral vectors is one that is capable of infecting cells and undergoing DNA replication, viral packaging and release from the infected cell.

"Conditionally replicating" viral vectors as used herein are replication-competent vectors that are designed to be selectively expressed in particular cell types so that undesired broad spectrum infection is avoided. Conditional replication may be achieved by including in the vector tissue-specific, tumor-specific or cell type-specific or other selectively induced regulatory control sequences that are operably linked to early viral genes.

The terms "stress" and "toxicity" are used to refer to the disturbance of the natural biochemical and biophysical homeostasis of the cell. Whereas stress generally leads to recovery of cellular homeostasis, a toxic response eventually results in cell death.

The translation regulated (TR) sequence (also referred to as the "TR element") employed in the present technology is the IRES element, which can be distinguished from the 5' UTR IRESs by (a) its nucleic acid sequence context and (b) the cellular activity which regulates translation (US Published Patent Application No. 2006/0173168). The combination of these two features forms a basis for selective translation of downstream coding sequences in stressed and/or dying mammalian cells that are operably linked to this IRES sequence. Thus, the present technology contemplates the use of any mammalian IRES as the TR element, which is selectively expressed in stressed and/or dying cells.

In some embodiments, the IRES element of this technology has cap-independent translational activity which localizes within the ORF of the mammalian Proteolipid Protein (plp) gene. In its native context, plp IRES activity resides within a multicistronic RNA containing several upstream ORFS ("uORFs") which effectively block ribosome scanning to internal AUG codons in normal cells. However, exposure of cells to toxic agents results in ribosome binding and translation from specific internal RNA sequences so that an internal amino acid sequence is translated from the 3' end of the plp ORF. Thus, the expression of an appropriate coding sequence, which is regulated by the TR element, permits the visualization, monitoring and modulation of cell death, which finds use in numerous applications. Recombinant DNA molecules provided herein allow for the selective expression of an RNA transcript containing one or more nucleic acid sequences encoding one or more polypeptides in stressed or dying cells.

In some embodiments, the TR element of the present technology is derived from exons 1-7 of the plp gene. While not being bound to a particular theory, it is believed that the exons 1 through 4 are sufficient to encode a functional IRES activity based on mutational analysis data. Furthermore, it is believed that the TR regulatory system, which plays a role in stress/death-specific translation is located within exons 6 and/or 7.

In contrast to the IRES element disclosed in US 2006/0173168, which is expressed in dying cells, a TR element of the present technology derived from PLP/DM20 differs in all of the following features:

1) nucleotide 1 (in SEQ ID Nos. 1 and 2) was mutated from A to T to remove the wild type AUG start codon in the myelin proteolipid protein PLP and DM20 cDNAs that directs the synthesis of the full length PLP and DM20 in order to prevent such synthesis from occurring;

2) nucleotide 4 was mutated from G to A in order to create a stop codon in the second possible reading frame of the PLP and DM20 cDNAs to prevent full length synthesis thereof;

3) nucleotides 6, 7 and 8 were mutated from C to T, T to G and T to A respectively to create a stop codon in the third possible reading frame of the PLP and DM20 cDNAs to prevent synthesis of the full length PLP and DM20;

4) nucleotides 17 and 18 were mutated from G to A and T to G, respectively to create the first stop codon in the main (first) open reading frame of the PLP and DM20 cDNAs to prevent their full length synthesis;

5) nucleotide 21 was mutated from T to A in order to create the second stop codon in the main (first) open reading frame of the PLP and DM20 cDNAs to prevent full length synthesis thereof;

6) nucleotide 27 was mutated from A to T in order to remove the AUG codon from the third possible reading frame of the PLP and DM20 cDNAs to prevent out-of frame translation initiation in the absence of the wild type AUG codon; and 7) the stop codon was deleted from the PLP and DM20 cDNAs to reduce interference with translation of the downstream open reading frame.

As a result, the TR elements of the present technology derived from PLP/DM20 do not direct cap-dependent translation of either PIRP-M or PIRP-L. In addition to the above changes, the following mutations were introduced into the TR elements from the DM 20 variant of the cDNA:

1) nucleotide 511 was mutated from A to T in order to remove the first in-frame internal AUG start codon in the DM20 variant that directs the synthesis of PIRP-M protein to prevent such synthesis from occurring; and 2) nucleotide 598 was mutated from A to T to remove the second in-frame internal AUG start codon in the DM20 variant that directs the synthesis of PIRP-L protein in order to prevent such synthesis from occurring.

Similarly, the following mutations were introduced into the TR elements from the PLP variant of the cDNA:

1) nucleotide 616 was mutated from A to T in order to remove the first in-frame internal AUG start codon in the PLP variant that directs the synthesis of PIRP-M protein to prevent such synthesis from occurring; and 2) nucleotide 703 was mutated from A to T to remove the second in-frame internal AUG start codon in the PLP variant that directs the synthesis of PIRP-L protein in order to prevent such synthesis from occurring.

The TR cassette of the present technology finds many uses in methods such as detecting cell death ex vivo or in vivo; determining the cytotoxicity of a compound in vivo or ex vivo; in vivo diagnostics; inducing apoptosis in a cell in vivo or ex vivo; preventing apoptosis in a cell in vivo or ex vivo; and combining the imaging of cell stress and/or death with subsequent treatment. In addition, the present technology details the methods for screening for additional TR cassettes, i.e., the IRES elements which are selectively expressed in stressed and/or dying cells.

Expression Cassettes

One aspect of the present technology is directed to a nucleic acid expression cassette expressible in mammalian cells. The expression cassette contains the following elements in a 5' to 3' direction: at least one transcriptional effector sequence, a TR element encoding an mRNA molecule that is selectively translated in stressed and/or dying cells, a nucleotide sequence operably linked to the TR element, and a polyadenylation sequence. The nucleotide sequence is a first open reading frame (ORF) sequence and encodes a polypeptide or a fragment thereof and is co-translated with the TR element.

In various embodiments, the TR elements of the present technology exhibit selective translation in stressed and/or dying cells. The term "selectively translated" or "selective translation" in stressed and/or dying cells means that the mRNA translation activity is observed in more than 95% of any cell line transformed with the TR expression cassette at the peak of the translation activity, e.g., within about 9 to about 18 hours following treatment with an acute toxic agent that induces cell stress and/or death, and that the translational levels of the first ORF of the inventive expression cassette rise to at least 50% of the expression levels of the same ORF when transcribed and translated from the same expression cassette lacking an operably linked TR element following treatment with the acute toxic agent. For example, a TR element within an expression cassette of the technology exhibits selective translation in stressed and/or dying cells within about 9 hours following treatment with calcium ionophore A23187 at a concentration of 5 µM, with mRNA translation being observed in more than 95% of a HEK293 cell line transformed with the expression cassette, and translation levels of the first ORF of the expression cassette being at least 50% of the translation levels of the same ORF when transcribed and translated from the same expression cassette lacking an operably linked TR element following the treatment. In some instances, a TR element within an expression cassette of the technology exhibits selective translation in stressed and/or dying cells within about 6 to about 9 hours following treatment with calcium ionophore A23187 at a concentration of 5 µM, with mRNA translation being observed in about 96, 97, 98, 99, 99.5 or 99.9% of a HEK293 cell line transformed with the expression cassette, and translation levels of the first ORF of the expression cassette being about 55, 60, 65, 70, 75, 80, 85, 90, or 95% of the translation levels of the same ORF when transcribed and translated from the same expression cassette lacking an operably linked TR element following the treatment.

In some embodiments of the present invention, the TR element is a plp IRES element, which does not direct translation of PIRP-M or PIRP-L. In other embodiments, the TR element is not derived from the plp IRES.

Thus, in one embodiment, the present technology relates to a nucleic acid expression cassette expressible in mammalian cells, wherein the expression cassette has the following elements in a 5' to 3' direction: at least one transcriptional effector sequence; a TR element encoding a mRNA molecule which is translated in stressed and/or dying cells; a 3' sequence flanking the TR element that contains restriction enzyme sites common in the art; a nucleotide sequence operably linked to the TR element, which is a first open reading frame (ORF) sequence and encodes a polypeptide or a fragment thereof and is co-translated with the TR element; and a polyadenylation sequence.

In a preferred embodiment, a TR element is selected from a human or a mouse TR element. More preferably, the TR element is selected from murine sequences $TR_{dm}$ (SEQ ID NO: 1) and $TR_{plp}$ (SEQ ID NO: 2).

$TR_{dm}$ nucleic sequence (SEQ ID NO: 1) was derived from the DM20 splice variant cDNA of the mouse proteolipid protein gene 1, but has been modified at nucleotide positions 1, 4, 6, 7, 8, 17, 18, 21, 27, 511, and 598. In addition, the last 3 nucleotides encoding the stop codon were removed.

$TR_{plp}$ nucleic sequence (SEQ ID NO: 2) was derived from the PLP splice variant cDNA of the mouse proteolipid protein gene 1, and it contains modifications at nucleotide positions 1, 4, 6, 7, 8, 17, 18, 21, 27, 616, and 703. $TR_{plp}$ differs from $TR_{dm}$ by the presence of nucleotides 349-453. The last 3 nucleotides encoding the stop codon were removed.

In addition to the TR element, the expression cassettes of the present technology comprise an upstream transcriptional effector sequence which regulates gene expression. In one embodiment, the transcriptional effector sequence is a mammalian promoter. In addition, the transcriptional effector can also include additional promoter sequences and/or transcriptional regulators, such as enhancer and silencers or combinations thereof. These transcriptional effector sequences can include portions known to bind to cellular components which regulate the transcription of any operably linked coding sequence. For example, an enhancer or silencer sequence can include sequences that bind known cellular components, such as transcriptional regulatory proteins. The transcriptional effector sequence can be selected from any suitable nucleic acid, such as genomic DNA, plasmid DNA, viral DNA, mRNA or cDNA, or any suitable organism (e.g., a virus, bacterium, yeast, fungus, plant, insect or mammal). It is within the skill of the art to select appropriate transcriptional effector sequences based upon the transcription and/or translation system being utilized. Any individual regulatory sequence can be arranged within the transcriptional effector element in a wild-type arrangement (as present in the native genomic order), or in an artificial arrangement. For example, a modified enhancer or promoter sequence may include repeating units of a regulatory sequence so that transcriptional activity from the vector is modified by these changes.

In one embodiment, the promoters are selected from constitutive, inducible, tissue specific, tumor specific and response gene promoters. Constitutive promoters can be selected, e.g., from Rous sarcoma virus (RSV) long terminal repeat (LTR) promoter, cytomegalovirus immediate early gene (CMV) promoter, simian virus 40 early (SV40E) promoter, cytoplasmic beta-actin promoter, adenovirus major late promoter, and the phosphoglycerol kinase (PGK) promoter. In a preferred embodiment, a constitutive promoter is a CMV promoter. In another preferred embodiment, a constitutive promoter is an SV40E promoter.

Selection of a promoter that is regulated in response to specific physiologic or synthetic signals can permit inducible transcription of the gene product. For example, in the case where expression of a transgene is toxic to the cells in which the vector is produced, it may be desirable to prevent or reduce transcription of the transgene. By way of example, a proapoptotic transgene can be toxic to the cell in which it is produced. Thus, several inducible promoter systems are available for production of vectors, which contain a transgene encoding a toxic protein.

Non-limiting examples of inducible promoters include the metal-regulated human metallothionine (hMT-IIA) promoter, the zinc-inducible human Zinc Transporter 1 (hZnT-1) promoter, dexamethasone (Dex)-inducible promoter, mouse mammary tumor virus (MMTV) promoter, ecdysone-responsive insect promoter, tetracycline responsive Tet-On® and Tet-Off® systems, RU486-inducible promoter and rapamycin-responsive promoter. In one embodiment, the inducible promoter is a metallothionine hMT-IIA promoter. In another embodiment, the inducible promoter is a zinc-inducible hZnT-1 promoter.

Methods and compositions are provided for the controlled induction of gene expression in a mammalian host cell. For example, DNA sequences which comprise the human metallothionein II (hMT-IIA) and zinc-inducible Zinc Transporter 1 (hZnT-1) transcriptional regulatory systems are induced by elevated concentrations of heavy metal ions and glucocorticoids. These inducible promoters are composed of multiple metal-regulatory elements (e.g., MRE) adjacent to a basal level transcriptional regulator.

In other indications, it may be desirable to activate transcription using promoters responsive to hormones or antibiotics. The ecdysone system (Invitrogen, Carlsbad, Calif.) consists of a tightly regulated expression mechanism that prevents basal level transgene expression, but allows for an over 200-fold induction of transcription. The system is based on the heterodimeric ecdysone receptor of *Drosophila*, and when ecdysone or an analog thereof (such as muristerone A) binds to the receptor, the receptor activates a promoter to turn on expression of the downstream transgene. In this system, both monomers of the heterodimeric receptor are constitutively expressed from one vector, whereas the ecdysone-responsive promoter which drives the expression of transgene is on a second plasmid. Thus, cotransfection of the two plasmids containing the regulated transgene and the receptor monomers into a reporter cell allows for the inducible expression of even toxic transgenes.

The Tet-Off® or Tet-On® system (Clontech, Palo Alto, Calif.) originally developed by Gossen and Bujard (Gossen and Bujard, 1992; Gossen et al., 1995) utilize tetracycline or tetracycline derivatives, such as doxycycline, to regulate transgene expression. In the Tet-On® system, gene expression is induced by tetracycline or doxycycline, whereas in the Tet-Off® system, antibiotic exposure eliminates gene expression. These systems are based on two regulatory elements derived from the tetracycline resistance operon of *E. coli*, namely the tetracycline operator DNA sequence and the tetracycline repressor protein. A Tet-regulated plasmid contains a minimal promoter with tetracycline-responsive operator elements. A second plasmid contains the tetracycline-controlled transactivator protein, which is a fusion protein comprised of the VP16 transcriptional activator domain and the wild-type tetracycline repressor protein of the Tet-Off® system. In the Tet-On® system, the tetracycline repressor protein has been altered so that transcription is activated by the presence of tetracycline or doxycycline.

Tissue specific promoters can be selected, e.g., from the transferrin (TF), tyrosinase (TYR), albumin (ALB), muscle creatine kinase (CKM), myelin basic protein (MBP), glial fibrillary acidic protein (GFAP), neuron-specific enolase (NSE), and synapsin I (SYN1) promoters. In one embodiment, the tissue specific promoter is a synapsin I (SYN1) promoter. In another embodiment, the tissue specific promoter is the ALB promoter.

Tumor specific promoters include but are not limited to promoters for vascular endothelial growth factor (VEGF), a VEGF receptor (i.e. KDR, E-selectin, or endoglin), alpha-fetoprotein (AFP), carcinoembryonic antigen (CEA), erbB2 (v-erb-b2 erythroblastic leukemia viral oncogene homolog 2), osteocalcin (bone gamma-carboxyglutamate protein, BGLAP), SLP1 (secretory leukoproteinase inhibitor or anti-leukoproteinase 1), hypoxia-response element (HRE), L-plastin (lymphocyte cytosolic protein 1) and hexokinase II (HK2). In one embodiment, the tumor specific promoter is an alpha fetoprotein (AFP) promoter. In another embodiment, the tumor specific promoter is a SLP1 promoter.

Response gene promoters, which stimulate transcription preferentially or uniquely under certain cellular states and/or in response to external chemical or environmental stimuli (i.e., heat or cold shock), can be selected, e.g., from promoters for early growth response gene 1 (EGR1/ZIF268), tissue-type plasminogen activator (t-PA), multidrug-resistance protein 1 (mdr-1), HSPA5/Grp78/BIP (heat shock 70 kDa protein 5), c-fos (v-fos FBJ murine osteosarcoma viral oncogene homolog), c-jun (v-jun sarcoma virus 17 oncogene homolog) or from cell cycle-regulated genes such as, but not limited to, E2F-1 (E2F transcription factor 1), cyclin A1 (CCNA1) and CDC25C (cell division cycle 25C). In a preferred embodiment, the response gene promoter is a promoter for HSPA5. In another preferred embodiment, the response gene promoter is an EGR1 promoter.

In some embodiments, a specific transcriptional effector element is isolated and then operatively linked to a minimal promoter to produce an expression cassette whose transcriptional activity is dependent upon a single or limited type of cellular response (e.g., a heat shock response or metal-regulated element).

The expression cassette can include species-specific transcriptional regulatory sequences. Such DNA regulatory sequences can be selected on the basis of the cell type into which the expression cassette will be inserted and can be isolated from prokaryotic or eukaryotic cells, including but not limited to bacteria, yeast, plant, insect, mammalian cells or from viruses. In such example, a mammalian promoter would be selected to express a nucleic acid of choice in a mammalian cell.

The TR expression cassettes of the present technology enable selective gene expression in stressed and dying cells, allowing for a heterologous ORF to be inserted 3' to the TR sequence and 5' of a polyadenylation signal. The heterologous gene can be either a full genomic sequence (e.g., including introns), synthetic nucleic acid or a cDNA copy of a gene of interest, which encodes a protein or a polypeptide of interest, wherein the polypeptide includes biologically active ("bioactive") protein fragments. In a preferred embodiment, cDNA sequences are used for the purposes of the present technology due to the reduction in genomic complexity provided by removal of mRNA splice sites.

Thus, in one embodiment, a first ORF sequence is selected from the group of reporter genes, cytotoxic tumor suppressor genes, toxin genes, prodrug activating genes and proapoptotic genes.

In various embodiments, the first ORF sequence is a reporter gene. As the name implies, a reporter gene does not confer any selective advantage on the cell into which it is introduced. Rather, a reporter gene encodes a product that confers on the cell a detectable biochemical or visually observable (e.g., fluorescent) phenotype. The reporter polypeptide can also include a fused or hybrid polypeptide in which another polypeptide is fused at the N-terminus or the C-terminus of the polypeptide or fragment thereof. A fused polypeptide is produced by cloning a nucleic acid sequence (or a portion thereof) encoding one polypeptide in-frame with a nucleic acid sequence (or a portion thereof) encoding another polypeptide. Techniques for producing fusion polypeptides are known in the art, and include, ligating the coding sequences encoding the polypeptides so that they are in-frame and translation of the fused polypeptide is under the control of the TR cassette. For example, cloning the plp ORF in-frame with the enhanced green fluorescent protein (EGFP) ORF produced a fusion protein that was used to monitor the expression, subcellular localization and biological effect of the fusion protein in cultured cells (Ghandour S et al. Glia (2002) 40(3):300-11; Boucher S et al. J Neurosci (2002) 22(5): 1772-83).

One commonly used class of reporter genes encodes an enzyme or other biochemical marker, which, when expressed in a mammalian cell, cause a visible change in the cell or the cell environment. Such a change can be observed directly, can involve the addition of an appropriate substrate that is converted into a detectable product or the addition and binding of a metabolic tracer. Examples of these reporter genes are the bacterial lacZ gene which encodes the β-galactosidase (β-gal) enzyme, the Chloramphenicol acetyltransferase (CAT) enzyme, Firefly luciferase (Coleoptera beetle), *Renilla* luciferase (sea pansy), Herpes Simplex 1 thymidine kinase (HSV1-TK) and the mutant Herpes Simplex 1 thymidine kinase (HSV1-sr39tk) genes. In the case of β-gal, incubation of expressing cells with halogen-derivatized galactose results in a colored or fluorescent product that can be detected and quantitated histochemically or fluorimetrically. In the case of CAT, a cell lysate is incubated with radiolabeled chloramphenicol or another acetyl donor molecule such as acetyl-CoA, and the acetylated chloramphenicol product is assayed chromatographically. Other useful reporter genes encode proteins that are naturally fluorescent, including the (green fluorescent protein (GFP), enhanced yellow fluorescent protein (EYFP), or monomeric red fluorescent protein (mRFP1).

As can be seen from above, exemplary reporter genes can be selected from GFP, EYFP, mRFP1, β-Gal, and CAT, but any other reporter gene known in the art can be used. See, e.g., the http World Wide Web olympusconfocal.com/applications/fpcolorpalette.html site. In a preferred embodiment, the reporter gene is Firefly Luciferase. In another preferred embodiment, the reporter gene is *Renilla* Luciferase.

The first ORF sequence can also encode a cytotoxic tumor suppressor gene that encodes a polypeptide capable of suppressing the neoplastic phenotype and/or inducing apoptosis. Examples of tumor suppressor genes useful in the practice of the present technology include the p53, adenomatous polyposis coli (APC), Breast Cancer-1 (BRCA-1), BRCA-2, Wilm's Tumor (WT-1), retinoblastoma gene (Rb), Neurofibromatosis-1 (NF-1), NF-2 and von Hippel-Lindau (VHL) genes. In a preferred embodiment, the cytotoxic tumor suppressor gene is the p53 gene.

In another embodiment, the first ORF sequence encodes a "toxin gene" that binds to cellular receptor proteins and after uptake interferes with protein synthesis by blocking ribosome assembly or function. Examples of toxin genes include proteins such as *Pseudomonas* exotoxin (e.g., Exotoxin A or "ETA"), ricin toxin, diphtheria toxin, and the like. In a preferred embodiment, the toxin gene is the diphtheria toxin gene.

In another embodiment, the first ORF sequence is a pro-drug activating gene (e.g., drug-susceptibility or suicide gene), which codes for a protein that converts a prodrug, which lacks a therapeutic effect into a drug which renders a cell expressing said gene susceptible to death following exposure to said prodrug. Examples of pro-drug genes include the thymidine kinase of Herpes Simplex Virus (HSV-tk), cytochrome P450, human deoxycytidine kinase and the bacterial enzymes cytosine deaminase and guanine phosphoribosyl transferase (gpt) genes. Cells which express these genes are rendered sensitive to the prodrugs ganciclovir (HSV-tk), cyclophosphamide (cytochrome P450), cytosine arabinoside (deoxycytidine kinase), 5-fluorocytosine (bacterial cytosonine deaminase) or thioxanthine (gpt). In a preferred embodiment, the prodrug activating gene is the HSV-tk gene which can also provide an important therapeutic advantage. During TK catalysis of the antiviral guanosine analogue ganciclovir, apoptotic molecules are released that kill surrounding cells by a process termed "bystander" killing. Although a limited number of target cells may initially express the HSV-tk gene, this localized cytocidal effect provides a therapeutic effect to adjacent non-expressing, undesired bystander cells.

In embodiments in which the first ORF sequence is a proapoptotic gene, such a sequence causes programmed cell death or apoptosis of an expressing cell. Examples of pro-apoptotic genes include p. 53, the Apoptosis Stimulating Proteins of p53 (e.g. ASPP1, ASPP2, and ASPP3), the Bcl-2 homologs Bax and Bcl2-L-10 (Diva), the Apoptosis-Inducing Factor (AIF), Fas, initiator caspases such as caspase-8 and caspase-9 or an effector caspase such as caspase-3. In a preferred embodiment, the proapoptotic gene is the caspase-3 gene.

In another embodiment, the first ORF sequence encodes a recombinant intracellular antibody ("intrabody") comprising an Fab or single chain Fv (scFv) molecule but does not encode an operable secretory sequence and hence are restricted to intracellular compartments where they bind, neutralize or modify the activity of a target antigen. This interaction may result in the direct inhibition of target antigen function, restoration of a mutant deficient activity, interference with the intracellular trafficking of the antigen or restriction of the folding of a pathological mutant protein. To exert their function, recombinant intrabodies are directed to a subcellular compartment where the antigen is located. This can be achieved by incorporating signal sequences routinely fused to the N- or C-terminus. For example, the KDEL peptide sequence allows the retention of recombinant antibodies within the endoplasmic reticulum and hence, can be used to block the processing of cell surface targeted proteins. Other signal sequences can be incorporated into the intrabody ORF and produce nuclear localization, ER or Golgi routing, nucleolar localization, as well as transport to the endosomal or liposomal compartments.

Methods for the production of single chain antibodies are well known to those with skill in the art. By way of example, the skilled artisan is referred to U.S. Pat. No. 5,359,046 for such methods. A single chain antibody ("scFv" or "SCA") is composed of an antibody variable light-chain amino acid sequence (VL) tethered to a variable heavy-chain sequence (VH) by a designed peptide that links the carboxyl terminus of the VL sequence to the amino terminus of the VH sequence, thereby reconstituting an antigen binding site on a single molecule. SCAs have the binding specificity and affinity of monoclonal antibodies and, in their native form, are about one-fifth to one-sixth of the size of a monoclonal antibody. In addition to these benefits, fully-human intrabodies can be isolated directly from human libraries (such as the human single-fold, single-chain variable fragment (scFv) libraries) without the need for costly and time consuming "humanization" procedures.

Almost any kind of biologic molecule can serve as an intrabody target antigen, for example, intermediate metabolites, sugars, lipids, and hormones as well as macromolecules such as complex carbohydrates, phospholipids, nucleic acids and proteins. The preferred target molecule is an endogenous protein. Intrabodies have been developed for a number of target proteins involved in cancer, infectious disease, transplantation, neurodegenerative disease and other diseases associated with protein overexpression or mutagenesis. Specific examples of intrabody target proteins include erbB-2 (androgen receptor), IL-2 receptor, epidermal growth factor receptor, vascular endothelial growth factor receptor 2, the folate receptor, HIV gp120 protein, CCR5, CXCR4, alphaV integrin, metalloproteinase MMP-2 and MMP-9, the RelA subunit of NF-kappaB, the prion-like protein PrP, the huntingtin protein and the beta-amyloid precursor protein. In one embodiment, the intrabody is directed to the RelA subunit of NF-kappaB.

In embodiments in which the first ORF encodes a secreted antibody fusion protein, such proteins can induce apoptosis or an enhanced immune response in targeted cells. Examples include any antibody fusion protein that delivers a therapeutic response such as the human interleukin-2-truncated diphtheria toxin, anti-CD22 dsFv-truncated *Pseudomonas* exotoxin, anti-CD25 scFv-truncated *Pseudomonas* exotoxin and the anti-B4-blocked ricin (anti-CD19) immunotoxin proteins. In one preferred embodiment, the antibody fusion protein is the anti-B4-blocked ricin immunotoxin protein.

Sequence Variants

In certain instances, sequence elements operably linked to the TR sequences might disrupt the selective translational activity displayed by the TR expression cassette or exhibit sub-optimal translational activity. To alleviate any effect on TR activity by the linked ORF, the present technology provides for codon-usage variants of the disclosed nucleotide sequences, that employ alternate codons which do not alter the polypeptide sequence (and thereby do not affect the biological activity) of the ORF products. These variants are based on the degeneracy of the genetic code, whereby several amino acids are encoded by more than one codon triplet. An example would be the codons CGT, CGG, CGC, and CGA, which all encode the amino acid, arginine (R). Thus, a protein can be encoded by a variant nucleic acid sequence that differs in its precise sequence, but still encodes a polypeptide with an identical amino acid sequence. Based on codon utilization/preference, codons can be selected to optimize the translation efficiency of an ORF without affecting regulated translation from the TR expression cassette.

Site directed mutagenesis is one particularly useful method for producing sequence variants by altering a nucleotide sequence at one of more desired positions. Site directed (or site specific) mutagenesis uses oligonucleotide sequences comprising a DNA sequence with the desired mutation, as well as a sufficient number of adjacent nucleotides to provide a sequence of sufficient size and complexity to form a stable duplex on both sides of the proposed mutation. Typically, a synthetic primer of about 20 to 25 nucleotides in length is preferred, with about 5 to 10 residues on both sides of the proposed mutation of the sequence being altered. Typical vectors useful in site directed mutagenesis include the disclosed vectors, as well as any commercially or academically available plasmid vector. In general, nucleotide substitutions are introduced by annealing the appropriate DNA oligonucleotide sequence with the target DNA and amplifying the target sequence by PCR procedures known in the art. The present technology contemplates the use of every possible codon in a coding sequence for producing the desired ORF sequence for use in accordance with this invention.

Directed evolution techniques can be used to prepare sequence variants having improved TR function. In a directed evolution technique, at least one round of nucleic acid mutation or nucleic acid splicing or homologous recombination can be performed, starting from a TR-containing polynucleotide. Mutation, splicing, and homologous recombination can be performed in a directed or random manner. For example, one or more oligonucleotides can be designed for site-directed mutagenesis of the TR element, as described above, or one or more randomly generated oligonucleotides can be contacted with the initial TR-containing polynucleotide template. Alternatively, or in addition, PCR amplification of the initial template can be performed under error-permissive conditions and/or an error-prone polymerase to permit introduction of mutations, a technique referred to a "sloppy" PCR.

Similarly, a set of homologous, TR-element-containing polynucleotides can be spliced or recombined in a directed or random manner. For example, one or more restriction endonucleases can be used to digest the homologous polynucleotide templates, randomly or in a predetermined manner, and the resulting fragments can then be ligated together. Alternatively or in addition, the set of TR-element-containing polynucleotides can be pooled and treated under conditions favoring homologous recombination among them, either in vitro or in cyto. A combination of mutation and splicing or recombination techniques can be employed. One or more than one rounds of any of these can be performed.

After one or more rounds of mutation, splicing, and/or recombination, the resulting polynucleotides are then tested to screen them for TR activity. Typically, this can be done by placing a reporter molecule coding sequence under the operative control of one or more of the TR variants that have been produced. The resulting construct(s) are then expressed in a cell that is placed under conditions, such as a condition of stress, for which TR translation can take place. The testing can be used to detect a desired improvement in TR element function. For example, any one of improvement in specificity of TR element translation to a stress condition, sensitivity of TR element activation to a cellular stress response (e.g., a biochemical change antecent to cell stress and/or death), or efficiency (i.e. magnitude) of translation initiation upon TR element activation can be the focus of the assay.

Based on the assay result, one or more improved TR elements can be selected for use, or for further development; in some embodiments, the selected improved TR element nucleic acids can be used as a starting polynucleotide or as a starting set of polynucleotides for another round, or course of rounds, of directed evolution.

In various embodiments herein, a TR element can comprise, or can be made by mutation of a PLP/DM20 polynucleotide comprising bases of, or corresponding to, bases from about 27 to about 615/510 of a murine or human PLP/DM20 DNA sequences of FIG. 15; and this can comprise further bases of, or corresponding to, bases from about 616/511 to about 702/597, bases from about 703/598 to about 772/666, and/or bases from about 773/667 to about 810/705. For example, a TR element can comprise, or can be made by mutation of a PLP/DM20 polynucleotide comprising bases of, or corresponding to, bases from about 27 to about 810/705, with or without omission of bases from about 616/511 to about 702/597, numbered with reference to FIG. 15.

In PLP/DM20 coding sequences, and TR elements thereof or constructed therefrom, mutations can be made, without adverse effect on TR-element function, at one or more positions corresponding to the following PLP/DM20 positions stated with reference to FIG. 15, i.e. positions: 01, 02, 03, 04 to 21 (including deletion of all of part of this segment), 25, 26, 314, 332, 560/455, 614/509, 622/518 to 696/591 (including deletion of all or part of this segment, which removes exon 5), 616/511, 703/598, 806/701, 811/706, 817/712, 818/713, and 827/722. In various embodiments, other nucleobases than the foregoing can be conserved in PLP/DM20 coding sequences.

For example, in various embodiments, a nucleobase sequence of a PLP/DM20 coding sequence hereof can comprise polypyrimidine motifs at nucleotide positions corresponding to PLP nucleotide positions 41-48, 50-56, 75-81, 150-156, 200-205, 227-244, 251-257, and 563-570. In some embodiments, such a sequence can further comprise polypyrimidine motifs at one or more of PLP positions 270-274, 299-303, 490-494, 578-582, 597-601; and in some embodiments, also at one or more of PLP positions 626-632, 642-648, 669-674, 707-712, 755-761, 767-771, and 800-804.

Similarly, in various embodiments, a nucleobase sequence of a PLP/DM20 coding sequence hereof can comprise GNRA motifs at nucleotide positions corresponding to PLP nucleotide positions: 130-133, 142-145, 190-193, 220-223, 305-308; and in some embodiments further at 635-638; and in other embodiments further at one or more of positions 329-332, 343-346, and 572-575; and in some, still further at one or more of positions 650-653 and 683-686.

However, as mentioned, mutation of the following positions can be undertaken with no adverse effect, and in some cases with an enhancing effect: 01, 04, 06, 07, 08, 17, 18, 21, 27. In some embodiments, these mutations can be one or more of: 01t, 04a, 06t, 07g, 08a, 17a, 18g, 21a, and 27t. Other positions that can be mutated with no adverse effect on function include mutations at one or more of PLP positions: 25, 26, 314, 332, 560/455, 616/511, 703/598, 806/701, 811/706, 817/712, 818/713, and 827/722. In some embodiments, these can be one or more of: 25g, 26c, 314g, 332g, 560/455c, 616/511t, 703/598t, 806/701g, 811/706t, 817/712a, 818/713a, and 827/722g. In addition, insertions, e.g., insertions of up to or about 5 nucleotides, can be made at PLP position 614/509, with no adverse effect on function. In addition, fusions to position 831/726, e.g., in-frame fusions thereto of reporter or other target gene coding sequences, do not exhibit any adverse effect on TR element function.

In various embodiments, a PLP or DM20 sequences useful herein can be a vertebrate sequence; in some embodiments, this can be a human, primate, rodent, equine, bovine, ovine, porcine, canine, feline, lapine, marsupial, avian, piscine, amphibian, or reptilian sequence. In various embodiments, a vertebrate sequence can be a native sequence, whether wild-type or variant; in some embodiments, a vertebrate sequence can be a wild-type sequence.

As used herein in regard to PLP/DM20 sequences, "vertebrate consensus sequence" refers to the DNA sequence as shown in SEQ ID NO: 62:

```
  1 atgggyykgy wdgakkgytg yrynmgmtgy mtbrtwgggg ymccmttygc ytchbtsrtb
 61 gccacwgkvy tvtgyttyky tggrgtsgcv ctvttctgyg gmtgyggrca ygargchytv
121 asygghacmg armagytvat ygagacmtay ttytccaara aytaccaaga mtaygartay
181 ctcatyvayg tsatymaygc yttycagtay gtcatctatg gaaywgccwy yttcttctty
241 cthtwyggrr ycctvctkyt ggcygarggm ttctacacca cmrsygchrt cargcavatc
301 ythggsgast wcmrrmccmc mryywkmrrs rrkggsctga kykcwacrgt racwggrggm
361 cmkaarggga grrghdcsmg rggmmvvcak cvagyycayw cywtrsagck srtstgtcrb
421 tgyttgggaa artggctmgg acayccygay aagtttgtsg gyrtyacyta tryyhtsacy
481 rtykt vtggm tmctrrystt ygcctgctcd gcygtdccyg tvtacatyta yttyaayacc
541 tggrycacyt gycagtctat ygcckyccch rssaagacyw cwrccagyrt mrgyasbcts
601 tgykcdgayg symgvatgta yggtgtycts ccmtggaayg cbttycchgg saargtktgy
661 ggswccarcc tkctbkccat ctgcaaracm rsygagttcc aratgacntt ycayctbttt
```

-continued

```
721 atygckgcvt tygtgggkgc wgcngchacw ctdgtbkcmc tgctcacytw yatgrthgsy 781 gcmwcwtwca actwygcygt sctbmrastb aykggccgrr gcwcmaagtt ytga
``` and to DNA complements thereof, to RNA sequences corresponding to any of the foregoing, to nucleic acid analogs having a nucleobase sequence corresponding to any of these, and to amino acid sequences encoded thereby.

As used herein in regard to PLP/DM20 amino acid and nucleotide sequences, "vertebrate specific sequence" refers to the PLP or DM20 sequences of the species listed in FIG. 14, i.e. *Homo sapiens, Pongo pygmaeus* (orangutan), *Pan troglodytes* (chimpanzee), *Macaca mulatta* (rhesus monkey), *Macaca fascicularis* (crab-eating macaque), *Sus scrofa* (pig), *Mus musculus* (mouse), *Rattus norvegicus* (rat), *Monodelphis domestica* (opossum), *Oryctolagus cuniculus* (rabbit), *Bos taurus* (cattle), *Canis familiaris* (dog), *Gallus gallus* (chicken), *Taeniopygia guttata* (zebra finch); *Gekko japonicus* (gecko lizard), *Xenopus laevis* (frog), and *Latimeria chalumnae* (coelacanth). In some embodiments, the vertebrate specific sequence can comprise, or encode, any one of the amino acid sequences having Genbank numbers: P60201 (human), Q5R6E6 (orangutan), XP_001140782 (chimpanzee), XP_001088537 (rhesus monkey), Q8HXW7 (crab-eating macaque), NP_999139 (pig), NP_035253 (mouse), NP_112252 (rat), XP_001374483 (opossum), P47789 (rabbit), CAA08909 (cattle), 39025 (dog), CAA43839 (chicken), P47790 (zebra finch), AAW79015 (gecko lizard), CAA79582 (frog), or BAA84207 (coelacanth).

DNA sequences encoding these are readily available to one of ordinary skill in the art by searching NCBI Genbank in the Nucleotide menu at the http World Wide Web ncbi.nlm.nih.gov/sites/entrez website. For example, useful DNA sequences include those listed under Genbank accession numbers: AJ006976 (human), CR860432 (orangutan), XM_001140782 (chimpanzee), XM_001088537 (rhesus monkey), AB083324 (crab-eating macaque), NM_213974 (pig), NM_011123 (mouse), NM_030990 (rat), XM_001374446 (opossum), NM_001082328 (rabbit), AJ009913 (cattle), X55317 (dog), X61661 (chicken), NM_001076703 (residues 113-946, zebra finch), AY880400 (gecko lizard), Z19522 (frog), and AB025938(coelacanth).

In various embodiments, a PLP or DM20 sequence useful herein can be a mammalian sequence; in some embodiments, this can be a human, primate, rodent, equine, bovine, ovine, porcine, canine, feline, lapine, or marsupial sequence.

As used herein in regard to PLP/DM20 sequences, "mammalian consensus sequence" refers to the DNA sequence as shown in SEQ ID NO: 63:

```
  1 atgggcytgt tagagtgytg ygcnagatgy ctsgtagggg cccctttgc ttccytggtg 61 gccactggat trtgtttctt tggrgtggca ctsttctgtg gmtgtggaca tgaagchytm 121 actggyacag aaaagytaat tgagacmtat ttctccaaaa aytaccaaga ctaygagtat 181 ctcatyaatg tgatycatgc yttccagtat gtcatctatg gaactgcctc tttcttcttc 241 ctttatgggg ccctcctgct ggcygagggc ttctacacca ccggygcwgt caggcagatc 301 tttggcgact acaagaccac catctgcggs aagggcctga gygcaacggt aacagggggc 361 cagaagggga ggggttccag aggccaacat caagctcatt ctttggagcg ggtgtgtcat 421 tgtttgggaa aatggctagg acatcccgac aagtttgtgg gcatcaccta tgccytgacy 481 gttgtrtggc tcctrgtgtt tgcctgctck gctgtrcctg tgtacattta yttcaayacc 541 tggaccacyt gycagtctat tgcckycccy agcaagacyt ctgccagyat aggcastctc 601 tgygctgatg ccagaatgta tggtgttctc ccatggaatg ctttyccwgg caargtktgt 661 ggctccaacc ttctgtccat ctgcaaaaca gctgagttcc aaatgacstt ccayctgttt 721 attgctgcvt tygtgggkgc tgcrgcyaca ctrgtktccc tgctcacctt catgattgct 781 gccacttaca acttygccgt cctkaaactc atgggccgag gcaccaagtt ctga
``` and to DNA complements thereof, to RNA sequences corresponding to any of the foregoing, to nucleic acid analogs having a nucleobase sequence of any of these, and to amino acid sequences encoded thereby.

As used herein in regard to PLP/DM20 amino acid and nucleotide sequences, "mammalian specific sequence" refers to the PLP or DM20 sequences of the mammalian species listed in FIG. 14, i.e. *Homo sapiens, Pongo pygmaeus* (orangutan), *Pan troglodytes* (chimpanzee), *Macaca mulatta* (rhesus monkey), *Macaca fascicularis* (crab-eating macaque), *Sus scrofa* (pig), *Mus musculus* (mouse), *Rattus norvegicus* (rat), *Monodelphis domestica* (opossum), *Oryctolagus cuniculus* (rabbit), *Bos taurus* (cattle), or *Canis familiaris* (dog). In some embodiments, the mammalian specific sequence can comprise, or encode, any one of the amino acid sequences having Genbank numbers: P60201 (human), Q5R6E6 (orangutan), XP_001140782 (chimpanzee), XP_001088537 (rhesus monkey), Q8HXW7 (crab-eating macaque), NP_999139 (pig), NP_035253 (mouse), NP_112252 (rat), XP_001374483 (opossum), P47789 (rabbit), CAA08909 (cattle), or 39025 (dog). TR elements comprising such TR polynucleotides are useful herein, as are expression cassettes comprising those TR elements.

In various embodiments, a TR element can have a PLP or DM20 nucleotide sequence that is at least 62% identical to a FIG. 15 PLP sequence or a FIG. 15 DM20 sequence, respectively. The sequence identicality can be at least or about 65, 70, 75, 80, 85, 90, or 95% thereto. In some embodiments, the sequence can be 97, 98, 99% or more identical thereto. Such a non-identical sequence will retain operative features a PLP or DM20 TR element, i.e. the defined polypyrimidine tracts, GNRA motifs, and 19S rRNA binding site thereof.

In various embodiments, TR elements hereof can be used to identify agents that induce, enhance, or inhibit a cellular stress response, e.g., a reponse to heat stress, cold stress, oxidation stress, tonic stress, toxication, or a combination thereof. The cellular stress response can comprises apoptosis and/or necrosis. In some embodiments, a process for identifying such agents can involve identifying the degree to which an agent induces, enhances, inhibits, or reverses a cellular stress response; this can be accomplished, e.g., by identifying a degree of cellular stress response that is proportional to the magnitude of a signal detected from a reporter molecule expressed under the control of the TR element.

In various embodiments, TR elements hereof can be used in processes for prophylactic, curative, or palliative treatment of a human subject who has need for protection against a cellular stress response. In such an embodiment, the TR element being part of a construct in which it is operatively attached to a polynucleotide comprising a coding sequence encoding an expression product that provides protection against a cellular stress response, and the treatment comprises administering a composition comprising such a construct. The protection provided thereby can be, e.g., an activity that sequesters or degrades a toxifying agent, that stabilizes biomolecules in the cell, that catalyzes the formation of a protective agent, or that causes expression of a protective agent from a different coding sequence.

Bicistronic TR Expression Cassettes

The expression cassette as described in the above sections is referred to as a monocistronic cassette due to the presence of only a single ORF sequence is the TR transcript. In addition to the monocistronic cassette, the present technology also contemplates the use of bicistronic TR expression cassettes, which include two ORF sequences.

Accordingly, in one embodiment of the present technology, the bicistronic TR expression cassette includes the second ORF sequence located 5' to the TR sequence in addition to the same elements described above for the monocistronic TR expression cassette, wherein the second ORF sequence is not operatively linked to the TR element. Thus, one skilled in the art will readily recognize that while the second ORF sequence is transcribed with the TR sequence and the first ORF in a single mRNA species, it is translated independently of the TR element and the first ORF sequence via a cap-dependent mechanism. The second ORF sequence finds utility when one would like to observe the differential effect of any agent or molecule on cap-dependent or cap-independent translation. For example, toxic agents will induce a transition from cap-dependent to cap-independent translation. Where the second ORF sequence is a reporter gene, the loss of reporter gene activity provides a temporal and quantitative measure of the transition from cap-dependent to cap-independent translation. Hence, a number of embodiments include a bicistronic expression cassette in which the first ORF sequence is a reporter gene, cytotoxic tumor suppressor, toxin gene, prodrug activating gene, antibody, derivative antibody or a proapoptotic gene, and the second ORF sequence is a reporter gene. Alternatively, a bicistronic TR expression cassette can include a first ORF sequence which is a reporter gene, and a second ORF sequence which is selected from a cytotoxic tumor suppressor, toxin gene, prodrug activating gene, single chain antibody or a proapoptotic gene. In this embodiment, the second ORF provides for the translation of a putative toxic gene product which stimulates the transition from cap-dependent to cap-independent translation which can subsequently be measured by reporter gene activity produced by TR-regulated translation of the first ORF. One skilled in the art can readily prepare any of these combinations. Exemplary monocistronic and bicistronic cassettes are shown in Tables 1-4.

In addition, SEQ ID NOs: 3-4 and SEQ ID NOs: 5-6 describe nucleic acid sequences for specific examples of monocistronic and bicistronic TR expression cassettes, respectively.

$TR_{dm}$ monocistronic cassette (pCMV-$TR_{dm}$-Luc) (SEQ ID NO: 3) contains the $TR_{dm}$ nucleic sequence operatively linked to firefly luciferase coding sequence. Nucleotides 1 to 589 of the cassette correspond to human cytomegalovirus immediate early promoter from pEYFP-N1 plasmid (Clontech). Nucleotides 590 to 630 correspond to an artificial linker sequence, which was extensively modified from the original pEYFP-N1 version. Nucleotides 631 to 1356 correspond to $TR_{dm}$. The next eight nucleotides are an artificial linker. Nucleotides 1369 to 1371 correspond to a Kozak consensus translation initiation site derived from the pEYFP-N1 plasmid. Nucleotides 1372 to 3024 correspond to the firefly luciferase open reading frame derived from phCMV-Luc-FSR plasmid (Genlantis). Nucleotides 3025 to 3171, 3179 to 3200, and 3207 to 3223 correspond to linker DNA derived from pEYFP-N1 plasmid. Nucleotides 3172 to 3178 and 3201 to 3207 correspond to the simian virus 40 (SV40) early gene polyadenylation signals derived from pEYFP-N1 plasmid. The mRNAs transcribed from this cassette start at nucleotide 583 and end at nucleotides 3211 or 3223.

$TR_{plp}$ monocistronic cassette (pCMV-$TR_{plp}$-Luc) (SEQ ID NO: 4) contains the $TR_{plp}$ nucleic sequence operatively linked to firefly luciferase coding sequence. Nucleotides 1 to 589 of the cassette correspond to human cytomegalovirus immediate early promoter from pEYFP-N1 plasmid (Clontech). Nucleotides 590 to 630 correspond to an artificial linker sequence (extensively modified from the original pEYFP-N1 version). Nucleotides 631 to 1461 correspond to $TR_{plp}$. The next eight nucleotides are an artificial linker. Nucleotides 1470 to 1476 correspond to a Kozak consensus translation initiation site derived from pEYFP-N1 plasmid. Nucleotides 1477 to 3129 correspond to the firefly luciferase open reading frame derived from phCMV-Luc-FSR plasmid (Genlantis). Nucleotides 3230 to 3276, 3284 to 3305, and 3313 to 3328 correspond to a linker DNA derived from pEYFP-N1 plasmid. Nucleotides 3277 to 3283 and 3306 to 3312 correspond to the SV40 early gene polyadenylation signals derived from pEYFP-N1 plasmid. The mRNAs transcribed from this cassette start at nucleotide 583 and end at nucleotides 3316 or 3328.

The $TR_{dm}$ bicistronic cassette (pCMV-Luc-$TR_{dm}$-EYFP) (SEQ ID NO: 5) contains the $TR_{dm}$ nucleic acid sequence with the second ORF encoding the firefly luciferase coding sequence and the operably linked first ORF encoding the EYFP coding sequence (the enhanced yellow-green variant of the Aequorea victoria green fluorescent protein). Nucleotides 1 to 589 of the cassette correspond to human cytomegalovirus immediate early promoter from pEYFP-N1 plasmid (Clontech). Nucleotides 590 to 630 correspond to an artificial linker sequence (extensively modified from the original pEYFP-N1 version). Nucleotides 631 to 2283 correspond to the firefly luciferase open reading frame derived from phCMV-Luc-FSR plasmid (Genlantis). The next six nucleotides are an artificial linker. Nucleotides 2290 to 3015 correspond to $TR_{dm}$. Next 23 nucleotides (3016 to 3038)

correspond to an artificial linker DNA from the pEYFP-N1 plasmid. Nucleotides 3039 to 3045 correspond to a Kozak consensus translation initiation site derived from pEYFP-N1 plasmid. Nucleotides 3046 to 3760 correspond to EYFP open reading frame derived from pEYFP-N1 plasmid. Nucleotides 3761 to 3912, 3920 to 3941, and 3949 to 3964 correspond to linker DNA derived from pEYFP-N1 plasmid. Nucleotides 3913 to 3919 and 3942 to 3948 correspond to the SV40 early gene polyadenylation signals derived from pEYFP-N1 plasmid. The mRNAs transcribed from this cassette start at nucleotide 583 and end at nucleotides 3952 or 3964.

The $TR_{plp}$ bicistronic cassette (pCMV-Luc-$TR_{plp}$-EYFP) (SEQ ID NO: 6) contains the $TR_{plp}$ nucleic acid sequence with the second ORF encoding the firefly luciferase coding sequence and the operably linked first ORF encoding the EYFP coding sequence (the enhanced yellow-green variant of the *Aequorea victoria* green fluorescent protein). Nucleotides 1 to 589 of the cassette correspond to human cytomegalovirus immediate early promoter from pEYFP-N1 plasmid (Clontech). Nucleotides 590 to 630 correspond to an artificial linker sequence (extensively modified from the original pEYFP-N1 version). Nucleotides 631 to 2283 correspond to the firefly luciferase open reading frame derived from phCMV-Luc-FSR plasmid (Genlantis). Next 6 nucleotides are an aritificial linker. Nucleotides 2290 to 3120 correspond to $TR_{plp}$. The next 23 nucleotides (3121 to 3143) correspond to an artificial linker DNA from the pEYFP-N1 plasmid. Nucleotides 3144 to 3150 correspond to a Kozak consensus translation initiation site derived from pEYFP-N1 plasmid. Nucleotides 3151 to 3865 correspond to EYFP open reading frame derived from pEYFP-N1 plasmid. Nucleotides 3866 to 4017, 4025 to 4046, and 4054 to 4069 correspond to linker DNA derived from pEYFP-N1 plasmid. Nucleotides 4018 to 4024 and 4047 to 4053 correspond to the SV40 early gene polyadenylation signals derived from pEYFP-N1 plasmid. The mRNAs transcribed from this cassette would start at nucleotide 583 and end at nucleotides 4057 or 4069.

Polyadenylation Sequence

One skilled in the art will readily recognize that any polyadenylation (polyA) signal can be incorporated into the 3' untranslated (3'UTR) of the monocistronic or bicistronic TR expression cassettes described herein. Examples of polyA sequences useful for the present technology include the SV40 early and late gene, the HSV-TK, and human growth hormone (hGH) sequences. In a preferred embodiment, the polyA sequence is the SV40 early gene sequence.

Optional Elements

In various embodiments, the 3'UTR of the TR cassette sequence can include one or more elements which regulate TR gene expression by altering mRNA stability. Typically, mRNA decay is exemplified by the loss of the mRNA polyA tail, recruitment of the deadenylated RNA to the exosome, and ribonuclease (RNAse) degradation. In select mRNAs, this process is accelerated by specific RNA instability elements that promote the selective recognition of a mRNA by cellular degradation systems. In this invention, an unstable TR cassette mRNA contains 3'UTR AU-rich element ("ARE") sequences derived from mRNA species encoding cellular response/recovery genes.

Examples of ARE sequences available to this technology include 3'UTR sequences from the c-fos, the granulocytemacrophage colony stimulating factor (GM-CSF), c-jun, tumor necrosis factor alpha (TNF-α), and IL-8 mRNAs. In a preferred embodiment, the ARE sequences from the c-fos gene are used.

The monocistronic and bicistronic expression cassettes of the present technology can also include a 5' untranslated region (5'UTR), which is located 3' to the promoter and 5' to the TR element. In some embodiments, such a region comprises a mRNA transcription initiation site. In other embodiments, the 5' untranslated region comprises an intron sequence, which directs mRNA splicing and is required for the efficient processing of some mRNA species in vivo. A general mechanism for mRNA splicing in eukaryotic cells is defined and summarized in Sharp (Science 235: 736-771 (1987)). There are four nucleic acid sequences which are necessary for mRNA splicing: a 5' splice donor, a branch point, a polypyrimidine tract and a 3' splice acceptor. Consensus 5' and 3' splice junctions (Mount, Nucl. Acids. Res. 10:459-472 (1992)) and branch site sequences (Zhuang et al., PNAS 86:2752-2756 (1989)) are known in the art.

In some embodiments, the 5' UTR sequences comprise natural introns which exist in a native gene sequence or an artificial intron, such as the human beta-globin-immunoglobulin sequence present in the pAAV-MCS vector (Stratagene).

Additionally, the expression cassettes of the present technology can include one or more of the following:

- a sequence of between about 15-50 nucleotides located 5' to the promoter, that includes one or more restriction sites for insertion of the TR cassette into a plasmid, shuttle vector or viral vector;
- a sequence of between about 15-50 nucleotides located 3' to the TR element and 5' to the ORF sequence, that includes one or more restriction sites for insertion and operative linkage of the TR element and the ORF sequence;
- a sequence of between about 15-50 nucleotides located 3' to the ORF sequence and 5' to the polyadenylation signal, that includes one or more restriction sites for insertion and operative linkage of the ORF sequence and the polyadenylation sequence; and
- a sequence of between about 15-50 nucleotides located 3' to the polyadenylation sequence, that includes one or more restriction sites for insertion of the TR cassette into a plasmid, shuttle vector or viral vector.

Vectors

The TR expression cassettes described herein can be inserted into plasmid or viral ("shuttle") vectors depending upon the host cell which is used to replicate the TR cassette. In general, the TR DNA expression cassette is inserted into the appropriate restriction endonuclease site(s) in the disclosed vectors using techniques known in the art. Numerous vectors useful for this purpose are generally known (Miller, Human Gene Therapy 15-14, 1990; Friedman, Science 244: 1275-1281, 1989; Eglitis and Anderson, BioTechniques 6:608-614, 1988; Tolstoshev and Anderson, Current Opinion in Biotechnology 1:55-61, 1990; Sharp, The Lancet 337: 1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechniques 7:980-990, 1989; Le Gal La Salle et al., Science 259:988-990, 1993; and Johnson, Chest 107:77 S-83S, 1995).

A plasmid vector is selected in part based upon the host cell that is to be transformed with the plasmid. For example, the presence of bacterial or mammalian selectable markers present in the plasmid, the origin of replication, plasmid copy number, an ability to direct random or site specific recombination with chromosomal DNA, etc. can influence the choice of an appropriate vector. In some embodiments, bacterial plasmids such as pBluescript II, pET14, pUC19, pCMV-MCS and pCMVneo are employed for propagating a TR cassette of the present technology in bacterial cells. In a preferred embodiment, a plasmid is the pCMVneo vector. In another preferred embodiment, the plasmid is the pBluescript II vector.

In another embodiment, a TR expression cassette is inserted into a mammalian or viral shuttle vector. Whereas mammalian shuttle vectors contain mammalian selectable markers and provide for the isolation of cells containing stable genomic integrants, viral shuttle vectors provide for the reconstitution of a viral genome using recombination or genetic complementation. In some embodiments, a mammalian shuttle vector is selected from the pCMV, pEYFP-N1, pEGFP-N1, or pEGFP-C1 plasmids. In a preferred embodiment, the mammalian shuttle vector is pEYFP-N1. In some embodiments, a viral shuttle vector is selected from the pAAV-MCS (Adeno-associated Virus serotype 2 or AAV2 genome) or pBac-1, pBacPAK8/9 (*Autographa californica* baculovirus genome) plasmids. In one preferred embodiment, the viral shuttle vector is pAAV-MCS. In another preferred embodiment, the viral shuttle vector is the pBac-1 plasmid.

To insure efficient delivery of the expression cassette to a particular cell, tissue or organ, it can be incorporated into a non-viral delivery system, which facilitates cellular targeting. For example, a mammalian shuttle plasmid that includes a TR cassette may be encapsulated into liposomes. Liposomes include emulsions, foams, micelles, insoluble monolayers, liquid crystals, phospholipid dispersions, lamellar layers and the like. The delivery of DNA sequences to target cells using liposome carriers is well known in the art as are methods for preparing such liposomes.

The viruses useful in the practice of the present technology include recombinantly modified enveloped or non-enveloped DNA and RNA viruses, preferably selected from the baculoviridiae, parvoviridiae, picornoviridiae, herpesviridiae (e.g., HSV), poxyiridiae, and adenoviridiae viruses. In some embodiments, the recombinant virus is a baculoviridiae virus. In a preferred embodiment, the baculovirus is an *Autographa californica* derivative virus. In other embodiments, the virus is a parvoviridiae virus, e.g., an adeno-associated virus ("AAV"). In a preferred embodiment, the AAV is an AAV serotype 2. In another embodiment, the AAV is an AAV serotype 1. This list is non-exclusive and can include, e.g., retroviridae such as lentivirus. A selected virus can be avirulent, or can be made avirulent as part of preparation as a viral vector hereof.

The viral genomes are preferably modified by recombinant DNA techniques to include the TR expression cassette and may be engineered to be replication deficient, conditionally replicating or replication competent. For example, it may prove useful to use a conditionally replicating virus to limit viral replication to specific, regulated cell culture conditions.

Chimeric viral vectors which exploit advantageous elements of more than one "parent" virus properties are included herein. Minimal vector systems in which the viral backbone contains only the sequences needed for packaging of the viral vector and optionally includes the expression cassette may also be produced and used in the present invention. It is generally preferred to employ a virus from the species to be treated, such as a human herpes virus when a human cell or a human cell line is transduced with it. In some instances, viruses which originated from species other than the one which is to be transduced therewith can be used. For example, adeno-associated viruses (AAV) of serotypes derived from non-human sources may be useful for treating humans because the non-human serotypes should not be immediately recognized by natural or pre-existing human antibodies. By minimizing immune responses to the vectors, rapid systemic clearance of the vector is avoided and the duration of the vector's effectiveness in vivo is increased.

Mammalian Cells

Mammalian cells of this technology containing a TR cassette can be used to screen for molecules (such as chemicals, drugs, peptides and nucleic acids) or environmental conditions (such as culture conditions or manipulations) that affect metabolism or cellular stasis and induces cell stress or death. These cells also enable the study of drug absorption, metabolism and safety, the identification of factors that affect drug metabolism and the evaluation and validation of pharmacological effects. A monocistronic or a bicistronic TR expression cassette in any of the mammalian shuttle vectors described above can be transformed into a mammalian cell. A shuttle vector can be introduced into the host cell by any technique available to those of skill in the art. These include, but are not limited to, chemical transfection (e.g., calcium chloride method, calcium phosphate method), lipofection, electroporation, cell fusion, microinjection, and infection with virus (Ridgway, A. "Mammalian Expression Vectors" Ch 24, pg 470-472, Rodriguez and Denhardt, Eds., Butterworhs, Boston Mass. 1988).

A mammalian cell can be a mammalian cell that is isolated from an animal (i.e., a primary cell) or a mammalian cell line. Methods for cell isolation from animals are well known in the art. In some embodiments, a primary cell is isolated from a mouse. In other embodiments, a primary cell is isolated from a human. In still other embodiments, a mammalian cell line can be used. Exemplary cell lines include HEK293 (human embryonic kidney), HT1080 (human fibrosarcoma), NTera2D (human embryonic teratoma), HeLa (human cervical adenocarcinoma), Caco2 (human colon adenocarcinoma), HepG2 (human liver hepatocellular carcinoma), Cos-7 (monkey kidney), ES-D3 (mouse embryonic stem cell), BALBC/3T3 (mouse fibroblast), and hES H1 (human embryonic stem cell). Host cell lines are typically available from, for example, the American Tissue Culture Collection (ATCC), any approved Budapest treaty site or other biological depository.

In still other embodiments, a mammalian embryonic stem (ES) cell can be used, such as a mouse ES cell mES-D3 or a human ES cell hES H1.

Cell Selection

The foregoing method requires the preparation of mammalian cell cultures. The cells used in the assays may be recombinant cells tailored to express the TR cassette. Once a mammalian cell or cell line is transformed with the TR expression cassette described herein, it is desirable to select cells with high expression of the first and/or second ORF. Several methods for doing so are known in the art, and are briefly described below.

A drug resistance gene, referred to as a "dominant selectable marker" that is present on the mammalian shuttle vector is utilized for such selection. The selective marker allows for the isolation of cells that have stably integrated the exogenous expression vector into the genomic DNA so that the cells that functionally incorporate the exogenous DNA develop constitutive resistance to the corresponding drug. This is most typically followed by the selective growth of cells in restrictive mediums and the establishment of a continuous supply of recombinant expressing cells. Examples of selectable markers include neomycin phosphotransferase ("NeoR or G418R"), hygromycin phosphotransferase ("HygR"), and puromycin N-acetyltransferase ("PurR").

Two methods are typically employed in the art to establish, characterize and store an expressing cell. The first involves the establishment, collection and storage of the entire population of transformed and drug resistant cells, in which each cell comprises at least one integration event of the transgene conferring drug resistance, termed a "cell pool." The second involves the isolation of individual cell colonies/clones derived from a single drug resistant cell, screening for a desired trait and storage as a cellular stock termed a "cell line."

In contrast to the first approach, which provides a mixed population of resistant cells with a wide array of gene expression levels, the second approach requires the selection of distinct clones from hundreds of isolated cell colonies to identify a select group of colonies which express the desired gene product at a desired level. Once these cells are identified, they are amplified, and either maintained in cell culture or frozen for future use.

Embryonic Stem Cells

Stem cells in particular find application in the methods of the present invention. Pluripotent, adult, blastocyst-derived, gonadal, teratoma-derived, totipotent, multipotent, embryonic (ES), embryonic germ (EG), and embryonic carcinoma (EC) cells are all examples of stem cells for use in these methods.

Pluripotent stem cells can be produced from the fetal material of any animal, such as any mammal. However, in one embodiment, the mammal is a rodent, such as a mouse, guinea pig or rat. In a preferred embodiment, the mouse ES cell is mES-D3. The fetal material can be from livestock, such as cattle, horses, pigs, sheep, goats, etc. The fetal material can also be from primates, including humans. Pluripotent stem cell lines have been reported, for example but not limited to, in chicken (Pain, B. et al., (1996) Development (Cambridge, U.K.) 122, 2339-2348), mink (Sukoyan, M. A. et al., (1993) Mol. Reprod. Dev. 36, 148-158), hamster (Doetschman, T. et al., (1988) Dev. Biol. 127, 224-227), pig (Wheeler, M. B. (1994) Reprod. Fertil. Dev. 6, 563-568; Shim, H. et al., (1997) Biol. Reprod. 57, 1089-1095), rhesus monkey (Thomson, J. A. et al., (1995) Proc. Natl. Acad. Sci. USA 92, 7844-7848), and common marmoset (Thomson, J. A. et al., (1996) Biol. Reprod. 55, 254-259). The derivation of stem cell lines is described in the references cited in the above paragraph.

Stem cells exhibit a variety of distinct properties and categories of properties. For example, in some forms, stem cell lines are capable of prolonged proliferation ex vivo (>1 year) in an undifferentiated state. Stem cells can also maintain a normal karyotype while proliferating and/or differentiating. Stem cells can also exhibit the ability to form every cell type in an organism (i.e. totipotent trait). Other stem cells retain the ability to differentiate into mesoderm, endoderm and ectoderm tissues, including germ cells, eggs and sperm. Some stem cells can form embryoid bodies (EBs) under certain growth conditions, such as culture conditions which do not maintain an undifferentiated state. Moreover, stem cells can often form chimeras through fusion with blastocysts, which is required for producing transgenic animals.

In addition to being kept in an undifferentiated state, the ES cells can be manipulated through changing growth conditions to induce differentiation into a particular cell type (referred to as "directed differentiation"). For example, pluripotent stem cells can be directed towards a specific lineage by molecules such as drugs, prodrugs, peptides and nucleic acids that 1) activate endogenous transcription programs which regulate differentiation; 2) introduce exogenous nucleic acids that ubiquitously express differentiation-specific transcription factors; 3) provide cell cultures with medium containing growth factors/regulatory molecules that induce differentiation; or 4) allow cocultures of stem cells and cell types capable of lineage induction. A number of ectodermal derivatives (ED) directed differentiation methods are described below, and can be used in the methods of the present invention.

In various embodiments, the present technology provides cell based systems for the identification of toxic agents. More specifically, transgenic ES cells, transformed with the TR cassette, may be programmed by directed differentiation to differentiate into specific cell lineages, to provide ex vivo cell-specific screens of toxic agents. In one embodiment the TR-regulated ORF is a reporter gene, more specifically, the firefly luciferase gene. In another embodiment, the TR-regulated ORF is the EYFP protein.

Genetic manipulation can be used to alter the properties of the stem cells. A modified stem cell is a stem cell that has a genetic background different than the original genotype of the cell. For example, a modified stem cell can be a stem cell that expresses protein sequences from an extra-chromosomal or integrated DNA sequence. Stem cell properties can be modified using selection for dominant selectable markers. For example, transformation/transduction with a vector encoding an antibiotic resistance gene can be used to select for a cell population that can survive antibiotic application. Cells that express the marker gene can also integrate cis-linked transgenes such as the TR cassette so that these transgenes are stably incorporated into the genome. Various methods exist in the art to prepare cell lines of genetically modified stem cells. One application of this technology is a method to employ genetically modified stem cell lines, capable of expressing the TR cassette, for cell based cytotoxicology assays. In one embodiment, the TR cassette encodes a reporter gene such as firefly luciferase, from the CMV promoter, providing a method for constitutive imaging of cell death. In another embodiment, the TR cassette encodes a reporter gene such as firefly luciferase, from the EGR-1 promoter, providing a method for imaging cell death during early stress responses. It is anticipated that a skilled artisan could design similar methods of imaging cell death in transgenic stem cells based upon a particular need or process of measuring and/or inducing cell death. By way of example, a number of methods are described in the art for producing the directed differentiation of stem cells ex vivo. Some of these are summarized in the subsequent sections. The formation of ectodermal derivative cells is common in spontaneously differentiating stem cells and is generally considered a default developmental pathway. The neuroectoderm cell fate can be selectively promoted to generate neural progenitors and differentiated neural cell types (e.g. neurons, astroglia and oligodendroglia) (Carpenter M K, et al. 2001). Oligodendrocytes can be produced from stem cell lines using FGF (e.g. FGF2) and epidermal growth factor (EGF), followed by supplementation with retinoic acid (RA). These oligodendrocyte precursors are able to mature and remyelinate neurons (Nistor G I, et al. 2005). Alternative multistep methods can produce dopaminergic neurons (Park S, et al. 2004; Perrier A L, et al. 2004) and motor neurons by culturing stem cells in RA and FGF-2, then RA and sonic hedgehog (SHH), and finally brain-derived neurotrophic factor (BDNF), glial-derived neurotrophic factor (GDNF), insulin-like growth factor-1 (IGF1) and low levels of SHH.

In contrast, treating stem cell cultures with bone morphogenetic protein (BMP), an antagonist of Noggin, generates stem cells with a flattened epithelial morphology and a gene expression pattern characteristic of extra-embryonic endoderm, a cell type commonly associated with the yolk sac and placenta in developing embryos. Thus, prolonged culture of stem cells in serum-free medium with BMP4 will produce flat epithelial cells that express genes (e.g., MSX2), and proteins (e.g., human chorionic gonadotrophin) associated with trophoblast or placental development.

Similarly, coculture of stem cells with the mouse bone marrow mesenchymal PA6 cell line, which expresses stromal cell derived inducing activity (SDIA), will produce a mixture of midbrain neurons that are tyrosine hydrolase positive (TH+) and express the nurr1 and LMX1b genes (Kawasaki H, et al. 2002; Mizuseki K, et al. 2003), as well as pigmented retinal epithelium cells. Further manipulation of culture conditions with BMP4 induces the formation of neural crest cells and dorsal-most central nervous system cells. Suppression of SHH promotes the formation of motor neurons (Trounson A. 2004). Stem cells can also be directed into midbrain dopamine neurons when grown with mouse bone marrow mesenchyme cell lines (e.g. MS5 and S2 cells), where there is sequential expression of the Pax2, Pax5 and engrailed-1 transcription factors in response to FGF-8, SHH, ascorbic acid/vitamin C and BDNF (Perrier A L, et al. 2004).

Exposure of partially differentiated neuroepithelial derivatives to FGF-8 and SHH promotes the production of dopaminergic neurons with a forebrain phenotype; however, early exposure to FGF-8 during neuroepithelial specification promotes a midbrain phenotype and a differentiation pathway leading to midbrain dopaminergic neurons. Hence, the order of administering FGF-8 and SHH can determine neuronal fate.

Coculture methodologies have also been used to produce differentiated cardiomyocytes from stem cells. 15-20% of cultures of stem cells grown with the mouse visceral endoderm cell type END-2, form beating heart muscle colonies (e.g. cardiomyocytes) (Mummery C, et al. 2002; Mummery C, et al. 2003). Beating heart muscle cells derived from stem cells express cardiomyocyte markers including alpha-myosin heavy chain, cardiac troponins and atrial natriuretic factor as well as transcription factors typical of cardiomyocytes, (e.g. GATA4 and MEF3) (Kehat I, et al. 2001; Xu C, et al. 2002). These cells respond to pharmacological drugs and exhibit cardiomyocyte action potentials most commonly observed in human fetal left ventricular cardiomyocytes, which can be easily distinguished from mouse cardiomyocytes (Mummery C, et al. 2003; He J Q, et al. 2003). Atrial- and pacemaker-like cells can also be formed in the differentiating stem cell cultures. These stem cell derived cardiomyocytes integrate normally into transplanted rodent and porcine heart muscle, form normal gap junction connections between stem cell myocytes and the recipient mouse adult cardiomyocytes (Xue T, et al. 2005; Kehat I, et al. 2004; Hassink R J, et al. 2003).

Type II pneumocytes that express Surfactant Protein C (SPC), a respiratory specific marker, can be generated by coculture of stem cells with mouse embryonic foregut mesenchyme (Denham M, et al. 2002). Stem cells can also be induced to form airway epithelial tissue when differentiated as embryoid bodies or grown on type 1 collagen, and then the resulting Clara cells grown in an air-fluid interface to form a pseudostratified surface epithelium (Coraux C, et al. 2005).

Keratinocytes can be derived from stem cells by replating embryoid bodies (Green H, et al. 2003). Cells expressing the transcription factor p63 in the periphery of the secondary cultures identify the keratinocyte progenitors that produce more mature cell types in which cytokeratin 14 and basonuclin are detected. These cells can form terminally differentiated stratifying epithelium but are not the same as keratinocyte epithelium isolated from neonatal or adult skin.

Embryoid bodies (EBs) can also be used to produce hematopoietic progenitors using a cocktail of hematopoietic cytokines and BMP-4 (Kaufman D S, 2001, Chadwick K, et al. 2003). EBs are formed by withdrawal of leukemia inhibitory factor (LIF) from the ES cell culture and manifest as cell clusters or spherical multicellular aggregates. These progenitors are immunologically similar to hematopoietic progenitors of the dorsal aorta. Growth factors such as stem cell factor (SCF), interleukins-3 and -6 (IL-3, IL-6), granulocyte colony-stimulating factor (GCSF), Flt-3 ligand, as well as vascular endothelial growth factor-A (VEGF-A) (Cerdan C, et al. 2004).

Endodermal cells can be detected in stem cells cultures following exposure to Activin A (Kubo A, et al. 2004). Insulin producing cells can be formed by differentiating neuroectodermal cells using the method of Lumelsky et al. (Lumelsky N, et al. 2001). Similarly, Segev et al. (Segev H, et al. 2004) produced islet-like clusters by culturing embryoid bodies in medium containing insulin, transferrin, selenium and fibronectin. Disaggregated cultures were allowed to form clusters in medium containing FGF-2 and then exposed to nicotinamide with low glucose in suspension culture. A high percentage of cell clusters expressed insulin, glucagon and somatostatin similar to immature pancreatic cells. Responsiveness to glucose and other antagonists suggested that these cells were immature, fetal-like pancreatic beta-islet cells.

Rambhatla et al. (2003) reported differentiation of stem cells into cells that expressed markers of hepatocytes (albumin, alpha-1-antitrypsin, cytokeratin 8 and 18) and accumulate glycogen. Treating embryoid bodies with sodium butyrate or adherent stem cell cultures with dimethyl sulfoxide followed by sodium butyrate resulted in hepatic-like endodermal cells (Lavon N, et al. 2004). Cellular morphology in differentiated adherent stem cell cultures can be used to select for endodermal populations that express markers of fetal liver (Stamp L A, et al. 2003).

Transgenic Animals

The present technology further relates to transgenic animals, which contain a TR expression cassette stably integrated into its genome. In some embodiments, the targeting nucleic acid constructs comprising the TR cassette are introduced into a pluripotent cell (e.g., ES cell, Robertson, E. J., In: Current Communications in Molecular Biology, Capecchi, M. R. (ed.), Cold Spring Harbor Press, Cold Spring Harbor, N.Y. (1989), pp. 39-44). Suitable ES cells may be derived or isolated from any species or from any strain of a particular species. In some embodiments, the species is a mouse, such as a 129 or C57BL/6 strain. In other embodiments, the species is a rat. Although not required, the pluripotent cells are typically derived from the same species as the intended recipient. ES cells may also be obtained from commercial sources (e.g., Genome Systems, Inc), from International Depositories (e.g., the ATCC), from University facilities (e.g., the Siteman Cancer Center Murine Embryonic Stem Cell Core, Washington University, St. Louis, Mo.) or, alternatively, may be derived as described in Robertson, supra. Examples of clonally-derived ES cells lines include 129/SVJ, RW-4 and C57BL/6 ES cells (Genome Systems, Inc.) or SCC10, B6/Blu, EDJ22, R1 and B6/GFP ES cells (Washington University).

ES cells are cultured under suitable conditions, for example, as described in Ausubel et al., CURRENT PROTOCOLS IN MOLECULAR BIOLOGY. Preferably, ES cells are cultured on non-mitotic "feeder layers" of stomal cells (such as STO cells (especially SNC4 STO cells) and/or primary embryonic fibroblast cells) as described by E. J. Robertson, supra, pp 71-112. Culture media preferably includes leukocyte inhibitory factor ("lif") (Gough, N. M. et al., Reprod. Fertil. Dev. 1:281-288 (1989); Yamamori, Y. et al., Science 246:1412-1416 (1989)), which prevents ES cell differentiation ex vivo. Stomal cells transformed with and constitutively expressing the lif growth factor can also be used as feeder cells.

The targeting constructs are introduced into the ES cells by any method which will permit the introduced molecule to undergo recombination at its regions of homology or by random integration, for example, but not limited to, micro-injection, calcium phosphate transformation, lipofection, viral vector or electroporation (Toneguzzo, F. et al., Nucleic Acids Res. 16:5515-5532 (1988); Quillet, A. et al., J. Immunol. 141:17-20 (1988); Machy, P. et al., Proc. Natl. Acad, Sci. (U.S.A.) 85:8027-8031 (1988)). In some embodiments, microinjection is used for inserting the constructs into ES cells with the nucleic acid construct being linearized prior to introduction into ES cells, e.g., by digestion with restriction nucleases.

In one aspect, the technology provides a method of expressing the TR cassette in a host cell using a promoterless DNA cassette according to the invention, allowing it to undergo site directed recombination into the coding sequence of a target gene of interest. Related aspects provide a method of expressing the TR cassette in a host cell by engineering a functional expression construct prior to introducing the construct into the host genome. One such "genomic transgene" is engineered ex vivo by inserting the TR cassette into a large genomic sequence (i.e. a cosmid or artificial eukaryotic chromosome encompassing the ORF of a target gene of interest), which replaces a target gene ORF and drives expression of the TR cassette from the transcriptional regulatory elements of the target gene. Large genomic transgenes then provide the desired TR cassette expression pattern using the target gene transcriptional regulatory system following random integration into the host cell.

Screening and selection of those cells into which the targeting construct has been integrated can be achieved using the positive selection marker and/or the negative selection marker in the construct. In various embodiments, the construct contains both positive and negative selection markers. In one aspect, methods which rely on expression of the selection marker are used, for example, by adding the appropriate substrate to select only those cells which express the product of the positive selection marker or to eliminate those cells expressing the negative selection marker. For example, where the positive selection marker encodes neomycin resistance, G418 is added to the transformed ES cell culture media at increasing dosages. Similarly, where the negative selection marker is used, a suitable substrate (e.g., gancyclovir if the negative selection marker encodes HSV-TK) is added to the cell culture. Either before or after selection using the appropriate substrate, the presence of the positive and/or negative selection markers in a recipient cell can also be determined by others methods, for example, hybridization, detection of radiolabelled nucleotides, PCR and the like. In various embodiments, cells having integrated targeting constructs are first selected by adding the appropriate substrate for the positive and/or negative selection markers. Cells that survive the selection process are then screened by other methods, such as PCR or Southern blotting, for the presence of integrated sequences.

After suitable ES cells containing the construct in the proper location have been identified, the cells can be inserted into an embryo, preferably a blastocyst. The blastocysts are obtained by perfusing the uterus of pregnant females. Suitable methods for accomplishing this are known to the skilled artisan, and are set forth by, e.g., Bradley et al, (1992) Biotechnology, 10:534-539. As an example, naturally cycling or superovulated female mice mated with males can be used to harvest embryos for the implantation of ES cells. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10 to 20 ES cells are injected into blastocysts using a glass microneedle with an internal diameter of approximately 20 μm. Insertion into the embryo may be accomplished in a variety of ways known to the skilled artisan; however, a preferred method is by microinjection. For microinjection, about 10-30 ES cells are collected into a micropipet and injected into embryos that are at the proper stage of development to permit integration of the foreign ES cell containing the construct into the developing embryo. In one embodiment, the blastocysts are obtained from, for example, the FVB/N strain of mice and the ES cells are obtained from, for example, the C57BL/6 strain of mice. With respect to recipient female mice, randomly cycling adult females are paired with vasectomized males. Mouse strains such as Swiss Webster, ICR or others can be used for this purpose. In one embodiment, recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

While any embryo of the right stage of development is suitable for use, it is preferred that blastocysts are used. In addition, preferred blastocysts are male and, furthermore, preferably have genes encoding a coat color that is different from that encoded by the genes ES cells. In this way, the offspring can be screened easily for the presence of the knockout construct by looking for mosaic coat color (indicating that the ES cell was incorporated into the developing embryo). Thus, for example, if the ES cell line carries the genes for black fur, the blastocyst selected will carry genes for white or brown fur. Southern blots and/or PCR may also be used to determine the presence of the sequences of interest. Mosaic (chimeric) offspring are then bred to each other to generate homozygous animals. Homozygotes and heterozygotes may be identified by Southern blotting of equivalent amounts of genomic DNA from mice that are the product of this cross, as well as mice that are known heterozygotes and wild type mice. Alternatively, Northern blots can be used to probe the mRNA to identify the presence or absence of transcripts encoding the TR cassette, the ORF nucleic sequence, or both. In addition, Western blots can be used to assess the level of expression of the ORF coding polypeptide, if a suitable antibody against such polypeptide exists. By way of example and not of limitation, if the polypeptide is GFP, an antibody against GFP can be used. Finally, in situ analysis (such as fixing the cells and labeling with antibody) and/or FACS (fluorescence activated cell sorting) analysis of various cells from the offspring can be conducted using suitable antibodies to look for the presence or absence of the targeting construct.

In another embodiment, transgenic animals can be made, which express the TR cassette and the ORF nucleic sequence only in a particular organ, tissue, cell or cell condition. The protocol for making such animals is the same as described above, except that a targeting construct comprises a promoter which is expressed only in the desired cells, tissue or organ, as well as cellular condition such as heavy metal application, thus limiting the expression of the TR cassette and the ORF coding polypeptide thereto. For example, if it is desirable that the targeting sequences be expressed in the liver and small intestine, the fatty acid binding protein (FABP) promoter can be used. In another example, transthyretin (TTR) (Ye et al., Mol Cell Biol., 1999 Dec., 19(12), 8570-80) promoter is also well described and widely used promoter to achieve liver-specific expression of transgenes. Other promoters for achieving tissue specific expression of genes are well known in the art and readily available.

Methods of Detecting a Reporter Protein or Reporter Nucleic Acid

Included in this technology are methods for detecting the reporter protein expressed in a cell transformed with a TR expression cassette wherein the first ORF sequence is a reporter gene. Briefly, the method comprises exposing the cell expressing such TR cassette to conditions suitable for translation of the reporter polypeptide, and detecting the presence of the reporter polypeptide. Any cell such as a primary cell, cell line, a cell that has been transduced in a subject, or a donor cell implanted in a subject can be used.

A variety of ex vivo protein detection methods are known in the art. For example, the polypeptides may be detected using methods known in the art that are specific for the polypeptides. These detection methods may include use of specific antibodies, formation of an enzyme product or disappearance of an enzyme substrate. Thus, the detection of reporter proteins can be achieved using any of the standard methods known in the art, such as fluorescence microscopy, immunohistochemistry, or ELISA assays. For example, fluorescence microscopy can be used to detect EYFP and mRFP1. Similarly, antibodies against Firefly Luciferase or β-Galactosidase can be used to detect presence thereof following immunofluorescence staining.

A number of noninvasive methods are available in the art to detect protein synthesis in vivo. By way of example, Herpes simplex virus type 1 thymidine kinase (HSV1-TK) ORF placed downstream of the TR element can be used to detect in vivo cell death using metabolic tracers. Unlike mammalian thymidine kinase, this enzyme can efficiently phosphorylate nucleoside analogues (e.g., ganciclovir, penciclovir), as well as various radioactive derivatives such as (9-(4-[18F]-fluoro-3-hydroxymethylbutyl)guanine; [18F]FHBG), which is then retained and accumulates within expressing cells. Thus if a cell is undergoing stress/death, the HSV1-TK will be translated from the TR cassette, resulting in accummulation of a radioactive tracer. The radioactivity can be detected using positron emmission tomography (PET), which allows for monitoring of the detailed location, magnitude, and persistence of reporter gene expression. Methods are also provided for mutant HSV1-TK enzymes (e.g., TKsr39) that exhibit enhanced enzymatic activity and/or binding constants that improve the sensitivity of PET imaging by enhancing the cellular accumulation of a radioactive tracer.

In a specific embodiment, transgenic cells and animals expressing TR-regulated light generating proteins, for example the firefly luciferase enzyme, are described. As demonstrated in specific examples, TR-regulated luciferase expression serves as a bioluminescent reporter of cell stress/death. In this embodiment, luciferase is particularly useful as a reporter for low-light imaging of bioluminescence in living cells and organisms. Although resolution is less than with MRI or PET, bioluminescence imaging, typically with a sensitive charged coupled device (CCD) camera, allows rapid, high throughput (simple data collection from multiple animals simultaneously), progressive (repeated analysis of the same animal), noninvasive, nondestructive data collection in vivo. A variety of detection devices, image processors and image analysis systems are available in the art.

The present technology also provides methods using transgenic cells and animals containing a TR cassette operably linked to stress- and response-specific promoters to restrict TR mRNA synthesis to selective cellular stress and response conditions. In this method, the TR nucleic acid (mRNA) and TR-regulated protein translation provide independent measures of cell stress and death. It is anticipated that this method will allow the detection of transcriptional activity regulated by cell stress which does not result in the stress/death-specific translational changes detected by the TR cassette. Various methods are available in the art to isolate, purify, and quantitate TR mRNA levels, such as, e.g., quantitative polymerase chain reaction (Q-PCR), real time PCR (RT-PCR), reverse transcriptase PCR (RT-PCR), in situ hybridization or nucleic acid hybridization in solution or solid support.

Method of Detecting Cell Stress and Apoptosis

In one embodiment, methods of detecting a reporter protein as described above are particularly useful in detecting cell stress and death. Cellular stress and death detection can be done either ex vivo or vivo. Thus, the present methods find use in studying normal biological processes, response of cells to injury or medication, exposure to a compound or condition thought to induce cytotoxicity, and the like. For example, as part of studying biological processes, a skilled artisan may want to determine if, and to what extent apoptosis plays a role in, e.g., cell differentiation. It may also be useful to determine the apoptotic potential of cells after a physical injury such as, e.g., a spinal cord trauma or after exposure to a cancer treatment drug. In addition, apoptosis detection is usable in evaluating cytotoxicity, e.g., of novel drugs.

In embodiments where detection is done ex vivo, one skilled in the art can use a primary cell, a cell line, or cells isolated from an animal, as discussed in above sections. Briefly, the cell that is to be evaluated for stress or death is initially transformed with a TR expression cassette, wherein the first ORF sequence is a reporter gene, such as EYFP. The methods for transforming cells are discussed above. The cells are cultured for an appropriate amount of time under toxic conditions, following which the reporter protein expression is detected using any of the above-mentioned methods. By way of example, fluorescence microscopy can be used to evaluate the number of cells that are translating a TR-EYFP cassette and exhibiting a toxic phenotype. Additionally, antibodies against a reporter protein, such as EYFP, can be used to determine the level of reporter protein expression using Western blot analysis.

For in vivo use, a TR cassette can be inserted into an ES cell line by any of the currently used transformation methods, such as, e.g., liposomes, electroporation, microinjection, etc., and a transgenic animal produced as described. For tissue specific expression of the TR cassette, a tissue specific promoter can be used. In some embodiments, a stress-specific promoter may be operably linked to the TR cassette to further restrict TR expression to stressed cells. In one preferred embodiment, a mammalian shuttle vector is used to deliver the TR cassette to ES cells. The transgenic animal would be exposed for an appropriate amount of time to a putative toxic drug or condition, following which reporter gene transcription and translation can be detected using the above-mentioned methods. Moreover, various standard methods for assaying gene expression and protein synthesis using postmortem animal tissue sections are well known in the art. An example would be the use of antibodies against a reporter protein, such as EYFP, to evaluate cell- and tissue-specific protein synthesis, as well as protein expression levels in stressed and dying cells in tissue sections. In other embodiments, the TR cassette provides methods for nondestructive in vivo imaging of cell stress and death. By way of example, micro-PET scanning can be used to evaluate the location and number of cells that are translating a TR-TKsr39 cassette.

Embryotoxicity and Cytotoxicity Assays

The technology provides in vitro test procedures for the detection of chemically-induced embryotoxicity and teratogenic effects based on differentiated, transgenic pluripotent embryonic stem cell (ESC) lines from the mouse and rat, as well as transgenic embryonic germ cells (EGCs) obtained from primordial germ cells of rodent embryos that have been transformed with the TR expression cassette. Previous in vitro efforts employing ESC lines to detect embryotoxic and mutagenic compounds, termed the Embryonic Stem Cell Test or EST, are known in the art (Laschinski et al., Reproductive Toxicol. 5, 57-65 (1991); Spielmann et al., Ex vivo Toxicol. 10: 119-27 (1997)). In summary, assaying disturbances of in vitro ES differentiation can be correlated with embryonic germ-layer aberrations. Since abnormal mammalian development can also lead to enhanced cell death and a resulting preimplantative embryo death, developmental defects, maldevelopment or malformations, early test procedures measured cytotoxic effects using the MTT test. In this embodiment, the EST procedure will be modified to examine cytotoxicity resulting in cell stress/death using TR-specific translation, which will serve as a measure of embryocidal properties of teratogenic/embryotoxic substances.

In some embodiments, the toxicity of a substance to the transgenic ES cell can be tested. The selection of appropriate ES cells for a particular substance and selection of factors such as substance concentration, duration of incubation of the substance with the ES cells and methods of detection can be easily performed by a skilled artisan. In general, such assays are performed ex vivo, utilizing transgenic ES or EG cell cultures transformed with the TR cassette. Briefly, a substance being tested is contacted with a population of ESCs for a period of time and assayed for TR-mediated translational activity, as described above. For example, a substance can be incubated with several different ES cell cultures over several different time periods (e.g., 12 hours, 24 hours, 48 hours, 72 hours), wherein the substance is applied to each culture at 4-20 different concentrations. The TR-based toxicity assay can then be determined using standard methods for reporter protein detection, as discussed above. An agent's toxic potential can be expressed in several ways, for example in terms of the time needed to achieve cell death or the amount of TR-regulated reporter protein detectable at a given time point. In one preferred embodiment, bioluminiscence is used to detect a TR-regulated reporter protein.

By way of example and not of limitation, if the substance that is tested is toxic to the tested cells, the cell will rapidly undergo stress and death resulting in translation of the TR cassette and the TR-regulated reporter protein, such as EYFP or firefly luciferase. The presence and/or amount of the reporter protein can then be determined by using, for example, fluorescence or bioluminiscence detection. In another embodiment, a substance can be administered to animals which have previously incorporated a TR cassette into at least some of their cells. For example, a mouse can be exposed to a potentially toxic substance following the injection of a virus encoding the TR cassette into an appropriate testing tissue or tissue site, wherein the first ORF sequence is a reporter gene. This will result in a focal infection and transduction of susceptible cells at the injection site. Methods are provided in this technology for measuring the toxicity of the substance to the animal by detecting the reporter protein in cells of said animal using any of in vivo or ex vivo methods already discussed.

In still another embodiment, the transgenic animals, or animal cells derived from transgenic animals, are used to screen compounds or substances for cytotoxicity using standard methodology and as described above. As an example, in such screening assays, the substance is administered to the animals, or introduced into the culture media of cells derived from these animals, over a period of time and in various dosages, following which the animals or animal cells are examined for reporter protein expression, as indicative of the cytotoxicity.

In addition to the cytotoxicity assays above, an assay to evaluate the "temporal" transition to a toxic phenotype in the presence of the toxic cellular stimulus can also be envisioned. In such an assay, one can compare stress-induced RNA synthesis from the TR cassette transcribed from inducible or stress-regulated promoters with death induced TR-dependent protein synthesis. Another example of a transitional assay employs cell-type specific or organ-specific transcriptional regulatory elements to allow the detection of cell type-specific or organ-specific toxins using any of the previously described detection methods.

Method of Identifying Additional TR Elements

The present technology also provides methods for identifying translationally regulated (TR) genes that are selectively translated during cell stress/death by stimulating translation of an unknown target mRNA with a toxic agent that induces stress or death in cells containing the target mRNA. After the treatment with the toxic agent, such as MG132 or calcium ionophore A23187, cellular mRNA is harvested, purified and separated into pools of actively translated and untranslated mRNA. While not being bound to a particular theory, it is believed that an mRNA encoding a protein required for a quick response to a toxic environment is rapidly translated following exposure to the toxic agent and that the encoded protein quickly appears. Methods of the present technology identify mRNAs actively translated during cell death by preparing mRNA pools containing multiple ribosomes ("polysomal") and ribosome-free, untranslated mRNAs. Following the induction of cell/tissue death using any physiological, chemical, or pathological stress, the mRNAs remaining engaged in translation (putative TR genes translated via cap-independent translation) can be separated from those which are untranslated using procedures such as fractionation on a sucrose density gradient, high performance gel filtration chromatography, or polyacrylamide gel matrix separation (Ogishima et al., 1984, Menaker et al., 1974, Hirama et al., 1986, Mechler, 1987, and Bharucha and Murthy, 1992), since mRNAs that are being translated contain bound ribosomes and, therefore, migrate differently than ribosome-free untranslated mRNAs.

The mRNA-ribosome fractionation can be enhanced by treating target cell/tissue with drugs that specifically inhibit or modulate transcription or translation and prevent mRNA-ribosome dissociation. Examples of such drugs are actinomycin D and cyclohexamide, respectively. A further refinement of the polysomal fraction can be made to discriminate between total polyribosomes or membrane bound ribosomes by methods known in the art (Mechler, 1987).

Following polysomal isolation and division into translated and untranslated pools, the mRNA is isolated utilizing techniques which are well known to those skilled in the art and are described, for example, in "Molecular Cloning; A Laboratory Manual" (Cold Springs Harbor Laboratory Press, Cold Spring Harbor, N.Y., 1989). Other methods for the isolation and extraction of RNA from cells/tissue can be used and will be known to those of ordinary skill in the art (Mach et al., 1986, Jefferies et al., 1994). mRNA is further purified to remove any contaminating ribosomal RNA using poly A selection, which is well known in the art.

The relative abundance of the many mRNA species found in each pool can be compared using any of the differential analysis technique common in the art including serial analysis of gene expression ("SAGE"), differential display, oligonucleotide arrays, representational difference analysis (RDA), cDNA microarrays and suppressive subtraction hybridization (SSH). Labeled mRNA (in a cDNA or PCR product form) from translated and untranslated fractions can be used as probes, to identify cDNA, genomic clones, or mRNA species that are fixed onto a solid matrix like microarrays (GEM) or membranes of any kind where clones can be either attached by electrophoresis, direct loading or capillary action onto the membrane. The label can be radioactive, fluorescent, or incorporating a modified base such as digoxigenin or biotin. As a control, mRNA levels in the translated fraction are compared to the total unfractionated material to discriminate between differentials in expression levels produced by transcription modulation from those that result from modulation of translation per se. A strong association of a particular mRNA with the translated mRNA pool can indicate that said gene is selectively expressed during cell stress/death.

Following the differential expression analysis, the genes which have been identified as putatively regulated by cap-independent translation can be PCR amplified from any of the available genomic or cDNA gene collections and inserted into the described TR cassette replacing the existing TR sequence and producing an "investigational" TR cassette. PCR primers will be designed to incorporate mutations analogous to those inserted into the previously described TR element to prevent translation from any cap-dependent translation initiation site. Any investigational TR element will be subjected to comparative analysis to determine whether these clones exhibit selective cell stress and/or death-specific translation.

In various embodiments, to exhibit the TR defined activity, an investigational TR clone displays the following translational parameters:

a) Minimal translational activity in normal mitotic cells, displaying no expression level greater than the normal level of cell death in these cultures determined by any of the standard assays present in the art, b) A rapid increase in translational activity in cells treated with an acute dose of a toxic agent, such as MG132 or the calcium ionophore A23187, which is initiated prior to 6 hours but no more than 9 hours after treatment, c) Translation activity observed in more than 95% of any cell line transformed with the investigational TR cassette and treated with an acute toxic agent, d) Translational levels that rise to more than 50% of the expression levels of the ORF transcribed and translated without an operably linked TR sequence following an acute toxic exposure, and preferably more than 60%, 70%, 80%, 85%, 90%, 95%, or 100%, e) Stress or death-specific translation initiation that occurs proximal to the initiation site of the operably linked ORF, f) No transcriptional or translational activity in the absence of any operably linked transcriptional effector sequence/promoter element in normal or dying cells, g) No evidence of TR-specific mRNA splicing in expressing cells which removes any TR sequence from the investigational TR cassette in normal or dying cells, h) Stress or death-specific translation is detected in multiple cell types composed of not less than 3 cell lines or tissues representing 3 distinct tissue types.

In a preferred embodiment, investigational TR elements will be derived from mammalian cells, preferably human cells. In another embodiment, investigational TR elements will be derived from rodent cells, preferably mouse cells.

Screening Assays for Substances Affecting Cell Stress or Toxicity

Use of the TR expression cassette of this technology in toxicity testing involves combining a cell line expressing the TR cassette with the agent to be screened (typically by adding it to the culture medium). The present technology also provides high-throughput screening assays of substances or compounds that induce, ameliorate or prevent cellular stress or toxicity.

In one embodiment, a compound's cytotoxic ability is evaluated using any of the cytotoxicity assays described above or by detecting the reporter protein, which is cotranslated with the TR element. Briefly, the compound is tested by incubating it with cells that have previously been transformed with a TR expression cassette, wherein the first ORF sequence encodes a reporter protein. Next, the cells are screened for expression of the reporter protein, wherein the presence of the reporter protein indicates the cytotoxic potential of the compound. Furthermore, the higher the concentration of the reporter protein in the cells and/or the larger the percentage of cells which are expressing the reporter protein correlate with the increase with cytotoxicity of the compound.

In another embodiment, in order to identify a substance that can alleviate or prevent cytotoxicity, the putative therapeutic substance is administered to any of the mammalian cells or transgenic animals described above after exposing the cells or animals to conditions that promote or induce cellular toxicity. For example, the cells can be initially exposed to radiation or treated with drugs which induce cytotoxicity, such as, e.g., methotrexate. Following the incubation of the putative therapeutic substance with the cells or transgenic animals, the differential expression of the reporter protein in cells or animals which were treated compared to the cells or animals which were untreated indicates the ability of the substance to alleviate or prevent cytotoxicity. For example, if the reporter gene is GFP, the reduction of the GFP expression in treated cells or animals compared to the untreated ones indicates the ability of a substance to reduce cytotoxicity. It should be obvious to one of ordinary skill in the art that the greater the reduction in the reporter protein expression in the treated cells or animals, the greater the ability of the substance that was used to treat such cells or animals to prevent or ameliorate cell death.

This method may find particular use in identifying substances with the ability to counter the cytotoxicity of many drugs that are used in treatment of, e.g., cancers. Such drugs are generally known as "chemotherapeutic" agents and include DNA damaging agents such as methotrexate, doxorubicin, daunorubicin, mitomycin, actinomycin D, bleomycin, plicomycin, taxol, vincristine, vinblastine, cisplatin, carmustine, melphalan, cyclophosphamide, chlorambucil, ifosfamide, nitosurea, tamoxifen, raloxifene, estrogen receptor binding agents, gemcitabien, navelbine, farnesyl-protein transferase inhibitors, transplatinum, 5-fluorouracil, temazolomide and analogs and derivatives of the same. Each chemotherapeutic agent is generally associated with several side effects which include stress and death in the skin, gastrointestinal tract, bone marrow, liver, and kidney.

Other drugs that are also associated with toxicity are exemplified by the generic categories of, sedatives, anti-inflammatory agents, antibiotics, analgesics, anesthetics, antiviral drugs, etc. For example, antibiotics exhibit toxic phenotypes ranging from minor gastrointestinal symptoms to more severe hepatotoxicity, nephrotoxicity, anemia, myalgias, arthalgias and cardiotoxicity.

In addition, substances that reduce the cytotoxicity of commonly used compounds such as food additives, social drugs, and alternative medical therapies can be identified using the above method. One example of a food additive, which is also used in the production of drugs, cosmetics and certain medical devices (i.e., contact lenses) is a color additive. FD&C Yellow No. 5, a compound used to color beverages, dessert powders, candy, ice cream, custards and other foods can cause skin trauma (hives) and general toxicity in a significant fraction of exposed individuals. Other food additives with potential cytotoxic effects include the cholesterol substitute olestera, sulfites, and monosodium glutamate (MSG). In the case of MSG, a small percentage of the population develops MSG symptom complex, a condition characterized by cell stress/toxicity with neurological symptoms including a burning sensation in the neck, forearm and chest numbness, tingling that radiates to the arms and back, warmth/weakness in the upper torso and head, chest pain, nausea, difficulty breathing, drowsiness and general lethargy. Substances that counter the effects of social drugs such as alcoholic beverages, and caffeinated liquids (e.g. coffee, colas, teas and the like) can also be identified. Alternative medical therapies include, e.g., herbs such as ginseng, *ginkgo biloba*, St. John's wort, ephedra and kava.

Any substances or compounds may be used to test for their ability to induce, ameliorate or prevent cell death. For example, small molecule libraries, e.g., obtained from a commercial source can be used. Screening of such libraries, including combinatorial screening libraries (e.g. peptide, chemical or oligonucleotide libraries), is a rapid and efficient way to examine a large number of substances. Combinatorial approaches also lend themselves to the rapid evolution of potential drugs by the creation of second, third or fourth generation substances modeled on active, but otherwise undesirable substances.

The substances or compounds to be screened can also include fragments or parts of naturally occurring substances or may be found as active combinations of known substances, which may be otherwise inactive. Compounds isolated from natural sources, such as animals, bacteria, fungi, plant sources, including leaves and bark, and marine samples in addition to the ones derived or synthesized from chemical compositions or man-made substances can also be assayed. Non-limiting examples of such compounds include proteins, peptides, amino acids, small molecules, nucleic acids, lipids, nutritional supplements such as vitamins or minerals, drugs or any other substance that may be designed through rational drug design starting from known inhibitors or stimulators of toxicity pathways.

Method of Inducing Cell Death

The present technology provides agents for inducing cell death. Such agents for inducing cell death exert a desired pharmacological effect on various diseases by inducing cell death resulting from the activation of cell death or inhibition of anti-cell death cellular pathways. Such agents include medicaments which comprise a substance having the aforementioned action as an active ingredient.

One application of this technology is in the production of therapies that improve the efficacy of patient treatment and simultaneously reduce any deleterious side effects of therapeutic applications. In many cases, combined therapies are used to address various clinical problems including those associated with cellular resistance to therapy for hyperproliferative diseases. In the context of the present technology, it is contemplated that supplemental therapy based on TR regulated polypeptides could be used in conjunction with curative surgery, chemotherapy, radiotherapy, gene therapy, hormone therapy or immunotherapy treatments, as well as alternative therapies that employ apoptosis or cell cycle regulating agents to treat these disorders. A hyperproliferative disease includes diseases and conditions that are associated with any sort of abnormal cell growth or abnormal cell growth regulation.

In methods of the present technology, the patient is a mammal, preferably a human. A variety of hyperproliferative and degenerative diseases can be treated according to the methods of the present technology. Nonlimiting examples of the hyperproliferative diseases contemplated for treatment by the present technology are cancer, psoriasis, rheumatoid arthritis, inflammatory bowel disease, osteoarthritis, and pre-neoplastic lesions of the mouth, prostate, breast, skin, etc.

One preferred embodiment is a method for negatively affecting cancer in a subject by killing cancer cells, inducing apoptosis in cancer cells, reducing the incidence or number of metastases, reducing tumor size, inhibiting tumor growth, reducing the blood supply to a tumor or cancer cell, promoting an immune response against cancer cells or a tumor, preventing or inhibiting the progression of cancer, or increasing the lifespan of a subject with cancer by combining a TR-based therapeutic with other treatments that are effective for killing or inhibiting cellular proliferation. For example, if tumor cells from a patient are not responding to treatment and not undergoing cell death as determined by the present methods, a TR cassette transcribed by a tumor-specific promoter encoding a toxin gene, prodrug activating gene, tumor suppressor gene or immunotherapeutic could be administered to stimulate apoptosis.

By way of example, a TR cassette encoding the thymidine kinase gene (e.g. HSV1TKsr39 enzyme derivative) transcribed by a tumor-specific promoter could be delivered, for example using a recombinant viral vector, to a specific tumor type where that tumor-specific promoter is preferentially active. Transcription of the TR cassette in these cells would allow the selective translation of this enzyme in tumor cells stressed by modest chemotherapy or radiotherapy treatments. A particular advantage is observed by treating HSV-TKsr39 expressing cells with specific protoxic nucleoside analogues, such as acyclovir and ganciclovir, since this enzyme produces monophosphate intermediates that are then phosphorylated by cellular kinases to provide potent DNA synthesis inhibitors. Cells expressing HSV-TK are rendered extremely sensitive to the toxic effect of ganciclovir, whereas the mammalian TK enzyme is relatively insensitive, resulting in a large therapeutic index. Tumor modeling experiments using gene delivery of HSV-TK have demonstrated complete regression of established tumors and long-term animal survival, even though only a portion of the tumor cells were actually transduced with the HSV-TK gene. This so-called "bystander" cytocidal effect provides an important therapeutic advantage, as it avoids the need to infect/transduce 100% of the tumor cells with the HSV-TK gene. It is anticipated that a skilled artisan could design similar methods of treatment based on a particular use in which cell death is preferred.

In the context of the present technology, it is contemplated that TR regulated proteins could be used simultaneously with other cell death therapies. Alternatively, TR supplemental therapy may precede or follow another treatment by intervals ranging from minutes to weeks. In situations, where the first treatment and the TR therapeutic are applied separately, one would ensure that a significant period of time did not expire between the times of each delivery, such that the first agent and the TR-regulated therapeutic would still exert an advantageous combinatorial effect.

Another embodiment envisions methods for combining TR-based imaging and cell death systems with standard cell death therapies. Advantages are provided for imaging cell death as a side effect of medical treatment, and if so, administering monocistronic and bicistronic TR expression cassettes encoding reporter and pro-death ORFs allows for temporal imaging based upon the vector TR cassette. In one example, two TR expression vectors could be delivered to tumor cells such that one vector expresses a TR-regulated reporter ORF and the second vector a TR-regulated cell death ORF. In this case, cap-independent translation following cell stress by a standard therapeutic, such as a chemotherapy drug, would direct TR-dependent cell imaging and supplemental therapy by the TR pro-death activity to targeted tumor cells. Alternatively, a single bicistronic TR cassette could be transduced into tumor cells wherein the upstream ORF encodes a reporter ORF and the TR-regulated ORF is a cell death regulator protein. In this example, the upstream ORF would allow cap-dependent translation and visualization of cell transduction prior to the death, so that the efficiency of transduction could be visualized prior to chemotherapy application, which would then be lost when cap-independent translation was induced by the chemotherapy application. Therefore, efficacious imaging-treatment paradigms can be designed by varying TR cassette composition and the timing of therapeutic applications which are anticipated to allow the minimization of side effects and off-site activities.

Furthermore, a bicistronic TR expression cassette can be used, such that both ORF sequences encode proteins which are cytotoxic. For example, the first and second ORF sequences can encode any combination of pro-apoptotic, pro-drug activating, single chain antibodies and toxin genes, as exemplified by the following non-limiting combinations: p53 and diphtheria toxin, p53 and sr39TK, sr39TK and ricin toxin, diphtheria toxin and ricin toxin, and p53 and BRCA-1.

The TR cassette can be applied to cells as naked plasmid DNA, or can be transduced into cells using viruses as described above. In one embodiment, it may be useful for the TR cassette to be expressed selectively in specific cell or tissue types. For such purposes, tissue-, cell- and condition-specific viruses which contain a TR cassette selectively transcribed by a regulated promoter can be used. For example, if a particular cancer cell type is to be targeted, a tumor specific promoter can be used as described above.

Method of Preventing Cell Death

One embodiment of the present technology is to provide a therapeutic that inhibits cell death. The present technology provides therapeutics for inhibiting cell death that can exert a desired pharmacological effect on various diseases by inhibiting cell death resulting from the activation of cell survival or inhibition of cell death cellular pathways. Such medicament comprise a substance having the aforementioned action as an active ingredient.

One application of this technology is in the production of therapies that improve the efficacy of patient treatment and simultaneously reduce deleterious side effects of treatment applications. In general, anti-cell death therapies are used to address clinical problems associated with chronic and acute cell death. In the context of the present technology, it is contemplated that TR regulated polypeptides could be used in conjunction with other treatments, such as curative surgery, chemotherapy, radiotherapy, gene therapy, hormone therapy or immunotherapy treatments, as well as alternative physical therapies, such as induced hypothermia, to prevent cell death. Chronic degenerative diseases would be exemplified by any disease or condition that produces progressive cell death over a significant fraction of the lifespan of the patient. An acute degenerative disease would be exemplified by any intense trauma or condition that produces immediate cell death.

In methods of the present technology, preferably the patient is a mammal, more specifically a human. A variety of degenerative diseases can be treated according to the methods of the present technology. Nonlimiting examples of chronic degenerative diseases would include neurological diseases such as Alzheimer's disease, Parkinson's disease, as well as diseases of other tissues such as liver necrosis. Similarly, acute degenerative diseases would be exemplified by traumatic injuries such as acute spinal cord injury, acute nerve damage, traumatic brain injury, fractures, stroke, congestive heart failure and severe burns.

One preferred embodiment is a method of preventing cell death in a subject by blocking cell death as a result of in situ TR-regulated gene expression or in combination with other treatments that are effective for inhibiting cell death. By way of example, TR-regulated expression of an antiapoptotic gene can reduce cell death in apoptotic cells. As used herein, the term "apotosis" refers to the physiological process known as programmed cell death. Apoptosis is unlike other forms of cell death that occur, for example, as a result of ischemia or necrosis, because apoptosis is an active, ATP-dependent form of cell death that typically requires new RNA and protein synthesis. A TR cassette encoding an antiapoptotic gene such as BCL2 (B-cell CLL/Lymphoma 2), BCL2L1 (Bcl-x1; BCL2-like 1), BCL2A1 (Bfl-1/A1; BCL2-related protein A1), BAG1 (BCL2-associated athanogene), TRAF1 (Tumor necrosis factor receptor-associated factor 1), BIRC3 (C-IAP2; Baculoviral inhibitor of apoptosis protein repeat-containing 3), BIRC5 (survivin; Baculoviral inhibitor of apoptosis protein repeat-containing 5), BAK1 (BCL2-antagonist/killer 1), or API5 (Apoptosis inhibitor 5) transcribed by a cell-specific promoter could be delivered, for example, using a recombinant viral vector, to a spinal cord neuron where that promoter is preferentially active. Transcription of the TR cassette in these cells would allow the selective translation of an anti-apoptosis protein in spinal cord neurons undergoing apoptosis as a result of traumatic spinal cord injury. It is anticipated that a skilled artisan could design similar methods of treatment based on a particular use in which the prevention of cell death is preferred. In one preferred embodiment, the antiapoptotic gene is BCL2. In another preferred embodiment, the preferred antiapoptotic gene is TRAF 1.

In context of the present technology, it is contemplated that TR regulated proteins could be used simultaneously with other cell death therapies. TR supplemental therapy may precede or follow another treatment by intervals ranging from minutes to weeks. In situations, where the first treatment and the TR therapeutic are applied separately, one would ensure that a significant period of time did not expire between the times of each delivery, such that the first agent and the TR-regulated therapeutic would still exert an advantageous combinatorial effect.

Another embodiment envisions methods that combine TR-based imaging and anti-apoptosis/cell death with standard death preventative therapies. Advantages are provided for imaging cell death as a side effect of medical treatment, and if so, administering monocistronic and bicistronic TR expression cassettes encoding reporter and anti-death ORFs allows for temporal imaging based upon the vector TR cassette. For example, healthy cells often undergo apoptosis in a cancer patient as a side effect of chemotherapy treatment, often targeting a specific sensitive organ. In one example, two TR expression vectors could be delivered to the sensitive organ, for example by injection of viral vectors, such that one vector expresses a TR-regulated reporter ORF and the second vector a TR-regulated anti-apoptosis ORF. In this case, cap-independent translation following cell stress by a chemotherapeutic would direct TR-dependent cell imaging and supplemental therapy by the TR anti-apoptotic activity in the targeted organ. Alternatively, a single bicistronic TR cassette could be transduced into the sensitive organ wherein the upstream ORF encodes a reporter ORF and the TR-regulated ORF is an anti-apoptotic protein. In this example, the upstream ORF would allow cap-dependent translation and visualization of cell transduction prior to stress, so that the efficiency of transduction could be visualized prior to chemotherapy application, which would be lost when cap-independent translation was induced by chemotherapy-regulated death. Therefore, efficacious imaging-treatment paradigms can be designed by varying TR cassette composition and the timing of therapeutic applications which are anticipated to minimize side effects and off-site activities.

To utilize the present method, a TR expression cassette can be applied to potentially dying cells, i.e., cells undergoing stress or cell death, either as naked plasmid DNA, or can be transduced into cells using viruses as described. The routes of administration vary depending on the type if cellular injury, where the cell is located in the body, etc. One skilled in the art can readily determine a preferred route of administration for a particular situation. For example, for a muscle injury, liposomes or vectors containing the TR cassette can be used. In one embodiment, it may be useful for the TR cassette to be selectively transcribed in specific cells or tissue types. For such purposes, tissue-, cell- and condition-specific cassettes have been constructed that are selectively transcribed by a regulated promoter. For example, if a particular cell type is sensitive to treatment-induced cell death/apoptosis, a cell-specific promoter can be used as described above. In another example, if a particular cell condition induces cell death then a TR cassette regulated by a responsive promoter might be applied as a therapeutic.

It is also contemplated that the present method can be used in growing large scale cell cultures. Generally, when the cells are expanded, at least some of them will undergo cell stress and/or apoptosis as a result of mixing, etc. Thus, by transforming the cells with the TR cassette containing the antiapoptotic gene, fewer cells will undergo apoptosis. For example, the present method can be used in bioreactors such as Wave Bioreactor® in combination with Cellbag® disposable bags for cell culture. See, e.g., U.S. Pat. No. 6,544,788.

Kits

The present technology provides methods for providing services to entities desiring to test the effect of compounds or agents on cell stress/death. Methods may comprise providing cells, combinations and reagents of this technology to entities for use in pharmacological screening. When applied in conjunction with in vivo therapeutic treatments, the present technology provides diagnostic kits and methods for determining, imaging and quantifying the toxicity of medical treatments in terms of the cell stress/death caused within the cell or tissue.

Also provided herein are kits comprising one or more of the components described herein in any number of separate containers, packets, tubes, vials and the like, or the components may be combined in any combination in such containers. The kit contains the TR expression cassette as described above or a mammalian cell transformed with the TR expression cassette. According to one embodiment, the plurality of cells in this kit are derived from a single cell line, wherein each cell contains a specific TR cassette which undergoes cap-independent translation upon the induction of cell stress/death. Optionally, a kit of this technology may also contain one or more reagents useful for detecting transcription of the TR cassette (such as cassette-specific oligonucleotides useful for PCR amplification), translation from the TR cassette (such as an antibody or enzyme substrate), one or more control compounds known to induce or inhibit promoter activity (and thereby expression of the TR cassette), one or more control compounds that produce a defined toxic response (and thereby promotes stress/death-specific translation of the TR cassette), one or more molecules or other compounds that inhibit, influence or activate a drug target or drug metabolizing enzyme expressed from the TR cassette and/or written information on the use of the vectors, cells or other components of the kit for drug screening or validation. The oligonucleotides employed in the above kits and methods of this technology are chosen based upon their ability to specifically hybridize under high stringency conditions to the transcription product synthesized from the TR cassette. Various methods of selecting the oligonucleotide sequences are known in the art.

In cases where the TR expression cassette is provided, it is preferred that the expression cassette be provided as part of a vector, such as a plasmid or virus. Any of the TR expression cassettes described herein can be used in the kits. In some embodiments, a monocistronic TR expression cassette used in a kit contains a reporter gene, such as GFP or EGFP as the first ORF sequence. In other embodiments, a bicistronic TR expression cassette includes two reporter genes, which are either the same or different. Mammalian cells that are provided in the kit are preferably from a mammalian cell line, such as HEK293.

Pharmaceutical Compositions

The present technology also provides pharmaceutical compositions comprising a TR expression cassette and a pharmaceutically acceptable carrier. The TR expression cassette can be provided on its own, as part of a vector or as part of a mammalian cell.

Pharmaceutical compositions are preferably administered to a subject in a biologically effective or therapeutically effective amount, either alone or in combination with one or more other agents. A therapeutically effective amount is a dosage that, when given for an effective period of time, achieves the desired therapeutic or clinical effect.

A therapeutically active amount of a nucleic acid construct may vary according to factors such as the disease state, age, sex, and weight of the individual, and the ability of the composition to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amount of the nucleic acid in cell associated form may be stated in terms of either the amount of the nucleic acid or in cell equivalents.

Thus an effective amount is between about 1 ng and about 1 gram per kilogram of body weight of the recipient, more preferably between about 1 ng and 10 mg/kg, more preferably, between about 1 µg and about 1 mg/kg. Dosage forms suitable for internal administration preferably contain (for the latter dose range) from about 0.1 mg to about 100 mg of active ingredient per unit. The active ingredient may vary from about 0.5 to about 95% by weight based on the total weight of the composition. Alternatively, an effective dose of cells expressing the nucleic acid is between about $10^4$ and about $10^9$ cells, more preferably between about $10^6$ and about $10^8$ cells per subject, preferably in split doses. Those skilled in the art of cell therapy can readily adjust these doses without undue experimentation.

The pharmaceutical composition comprising a TR expression cassette or a cell transfected with the same can be administered in any convenient manner, e.g., by injection or infusion. The preferred routes of administration include intravenous, intrathecal, intracerebroventricular, subcutaneous, intradermal, and intramuscular routes. Other possible routes include oral administration, inhalation, or rectal administration.

Depending on the route of administration, the pharmaceutical composition of the present technology may be coated in a material to protect the composition from the action of enzymes, acids and other natural conditions which may inactivate the composition. For example, carriers such as liposomes (including water-in-oil-in-water emulsions as well as conventional liposomes (Strejan et al., (1984) *J. Neuroimmunol* 7:27)) can be used. In such instances, the TR expression cassette either on its own or as part of a vector can be either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The pharmaceutically acceptable carrier (herein also referred to as "carrier"), also known in the art as an excipient, vehicle, auxiliary, adjuvant, or diluent, is typically a substance which is pharmaceutically inert, confers a suitable consistency or form to the composition, and does not diminish the efficacy of the composition. The carrier is generally considered to be pharmaceutically or pharmacologically acceptable if it does not produce an unacceptably adverse, allergic or other untoward reaction when administered to a mammal, especially a human. A "pharmaceutically acceptable carrier" includes, for example, any and all solvents, dispersion media, coatings, antibacterial and antifungal agents, and isotonic and absorption delaying agents. The use of such media and agents for pharmaceutically active substances is well known in the art. Formulation of drugs is discussed in, for example, Hoover, John E., *Remington's Pharmaceutical Sciences*, Mack Publishing Co., Easton, Pa. (1975), and Liberman, H. A. and Lachman, L., Eds., *Pharmaceutical Dosage Forms*, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic acceptable diluent or solvent. Among the acceptable vehicles and solvents that may be employed are water, Ringer's solution, and isotonic sodium chloride solution. In addition, sterile, fixed oils are conventionally employed as a solvent or suspending medium. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful. Prolonged absorption of the injectable compositions can be brought about by including in the composition an agent which delays absorption, for example, aluminum monostearate and gelatin.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the composition.

Solid dosage forms for oral administration may include capsules, tablets, pills, powders, and granules. In such solid dosage forms, the compounds are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

In sprayable aerosol preparations, the pharmaceutical composition of the present technology can be provided in combination with a solid or liquid inert carrier material. Such preparation can be packaged in a squeeze bottle or in admixture with a pressurized volatile, normally gaseous propellant. The aerosol preparations can contain solvents, buffers, surfactants, and antioxidants in addition to the composition of the technology.

Prevention of the action of microorganisms can be achieved by various antibacterial and antifungal agents, for example, parabens, chlorobutanol, phenol, ascorbic acid, thimerosal, and the like.

Exemplary Expression Cassettes

Tables 1 and 2 below describe numerous monocistronic and bicistronic TR cassettes, respectively. As discussed previously, monocistronic TR cassettes comprise one of the TR elements operatively linked to a 3' ORF sequence whereas the bicistronic cassettes comprise a TR element operatively linked to upstream and downstream ORF sequences. The exemplary monocistronic cassettes are represented by SEQ ID NOs: 3-4 whereas the bicistronic sequences are exemplified by SEQ ID NOs: 5-6. For purposes of both Tables, specific promoters, TR elements and ORF sequences that can be used are described in greater detail above.

TABLE 1

Monocistronic TR Expression Cassettes

| Promoter | TR Element | ORF Sequence |
|---|---|---|
| Constitutive | $TR_{drn}$ | Reporter Gene |
| Constitutive | $TR_{plp}$ | Reporter Gene |
| Inducible | $TR_{drn}$ | Reporter Gene |
| Inducible | $TR_{plp}$ | Reporter Gene |
| Tissue Specific | $TR_{drn}$ | Reporter Gene |
| Tissue Specific | $TR_{plp}$ | Reporter Gene |
| Tumor Specific | $TR_{drn}$ | Reporter Gene |
| Tumor Specific | $TR_{plp}$ | Reporter Gene |
| Response Gene | $TR_{drn}$ | Reporter Gene |
| Response Gene | $TR_{plp}$ | Reporter Gene |
| Constitutive | $TR_{drn}$ | Cytotoxic Tumor Suppressor |
| Constitutive | $TR_{plp}$ | Cytotoxic Tumor Suppressor |
| Inducible | $TR_{drn}$ | Cytotoxic Tumor Suppressor |
| Inducible | $TR_{plp}$ | Cytotoxic Tumor Suppressor |
| Tissue Specific | $TR_{drn}$ | Cytotoxic Tumor Suppressor |
| Tissue Specific | $TR_{plp}$ | Cytotoxic Tumor Suppressor |
| Tumor Specific | $TR_{drn}$ | Cytotoxic Tumor Suppressor |
| Tumor Specific | $TR_{plp}$ | Cytotoxic Tumor Suppressor |
| Response Gene | $TR_{drn}$ | Cytotoxic Tumor Suppressor |
| Response Gene | $TR_{plp}$ | Cytotoxic Tumor Suppressor |
| Constitutive | $TR_{drn}$ | Toxin Gene |
| Constitutive | $TR_{plp}$ | Toxin Gene |
| Inducible | $TR_{drn}$ | Toxin Gene |
| Inducible | $TR_{plp}$ | Toxin Gene |
| Tissue Specific | $TR_{drn}$ | Toxin Gene |
| Tissue Specific | $TR_{plp}$ | Toxin Gene |
| Tumor Specific | $TR_{drn}$ | Toxin Gene |
| Tumor Specific | $TR_{plp}$ | Toxin Gene |
| Response Gene | $TR_{drn}$ | Toxin Gene |
| Response Gene | $TR_{plp}$ | Toxin Gene |
| Constitutive | $TR_{drn}$ | Prodrug Activating Gene |
| Constitutive | $TR_{plp}$ | Prodrug Activating Gene |
| Inducible | $TR_{drn}$ | Prodrug Activating Gene |
| Inducible | $TR_{plp}$ | Prodrug Activating Gene |
| Tissue Specific | $TR_{drn}$ | Prodrug Activating Gene |
| Tissue Specific | $TR_{plp}$ | Prodrug Activating Gene |
| Tumor Specific | $TR_{drn}$ | Prodrug Activating Gene |
| Tumor Specific | $TR_{plp}$ | Prodrug Activating Gene |
| Response Gene | $TR_{drn}$ | Prodrug Activating Gene |
| Response Gene | $TR_{plp}$ | Prodrug Activating Gene |
| Constitutive | $TR_{drn}$ | Proapoptotic Gene |
| Constitutive | $TR_{plp}$ | Proapoptotic Gene |
| Inducible | $TR_{drn}$ | Proapoptotic Gene |
| Inducible | $TR_{plp}$ | Proapoptotic Gene |
| Tissue Specific | $TR_{drn}$ | Proapoptotic Gene |
| Tissue Specific | $TR_{plp}$ | Proapoptotic Gene |
| Tumor Specific | $TR_{drn}$ | Proapoptotic Gene |
| Tumor Specific | $TR_{plp}$ | Proapoptotic Gene |
| Response Gene | $TR_{drn}$ | Proapoptotic Gene |
| Response Gene | $TR_{plp}$ | Proapoptotic Gene |

TABLE 2

Bicistronic TR Expression Cassettes

| Promoter | First ORF Sequence | TR Element | Second ORF Sequence |
|---|---|---|---|
| Constitutive | Reporter Gene | $TR_{drn}$ | Reporter Gene |
| Constitutive | Reporter Gene | $TR_{plp}$ | Reporter Gene |
| Inducible | Reporter Gene | $TR_{drn}$ | Reporter Gene |
| Inducible | Reporter Gene | $TR_{plp}$ | Reporter Gene |
| Tissue Specific | Reporter Gene | $TR_{drn}$ | Reporter Gene |
| Tissue Specific | Reporter Gene | $TR_{plp}$ | Reporter Gene |
| Tumor Specific | Reporter Gene | $TR_{drn}$ | Reporter Gene |
| Tumor Specific | Reporter Gene | $TR_{plp}$ | Reporter Gene |
| Response Gene | Reporter Gene | $TR_{drn}$ | Reporter Gene |
| Response Gene | Reporter Gene | $TR_{plp}$ | Reporter Gene |
| Constitutive | Reporter Gene | $TR_{drn}$ | Cytotoxic Tumor Suppressor |
| Constitutive | Reporter Gene | $TR_{plp}$ | Cytotoxic Tumor Suppressor |
| Inducible | Reporter Gene | $TR_{drn}$ | Cytotoxic Tumor Suppressor |
| Inducible | Reporter Gene | $TR_{plp}$ | Cytotoxic Tumor Suppressor |
| Tissue Specific | Reporter Gene | $TR_{drn}$ | Cytotoxic Tumor Suppressor |
| Tissue Specific | Reporter Gene | $TR_{plp}$ | Cytotoxic Tumor Suppressor |
| Tumor Specific | Reporter Gene | $TR_{drn}$ | Cytotoxic Tumor Suppressor |
| Tumor Specific | Reporter Gene | $TR_{plp}$ | Cytotoxic Tumor Suppressor |
| Response Gene | Reporter Gene | $TR_{drn}$ | Cytotoxic Tumor Suppressor |
| Response Gene | Reporter Gene | $TR_{plp}$ | Cytotoxic Tumor Suppressor |
| Constitutive | Reporter Gene | $TR_{drn}$ | Toxin Gene |
| Constitutive | Reporter Gene | $TR_{plp}$ | Toxin Gene |
| Inducible | Reporter Gene | $TR_{drn}$ | Toxin Gene |
| Inducible | Reporter Gene | $TR_{plp}$ | Toxin Gene |
| Tissue Specific | Reporter Gene | $TR_{drn}$ | Toxin Gene |
| Tissue Specific | Reporter Gene | $TR_{plp}$ | Toxin Gene |
| Tumor Specific | Reporter Gene | $TR_{drn}$ | Toxin Gene |
| Tumor Specific | Reporter Gene | $TR_{plp}$ | Toxin Gene |
| Response Gene | Reporter Gene | $TR_{drn}$ | Toxin Gene |
| Response Gene | Reporter Gene | $TR_{plp}$ | Toxin Gene |
| Constitutive | Reporter Gene | $TR_{drn}$ | Prodrug Activating Gene |
| Constitutive | Reporter Gene | $TR_{plp}$ | Prodrug Activating Gene |
| Inducible | Reporter Gene | $TR_{drn}$ | Prodrug Activating Gene |
| Inducible | Reporter Gene | $TR_{plp}$ | Prodrug Activating Gene |
| Tissue Specific | Reporter Gene | $TR_{drn}$ | Prodrug Activating Gene |
| Tissue Specific | Reporter Gene | $TR_{plp}$ | Prodrug Activating Gene |

TABLE 2-continued

Bicistronic TR Expression Cassettes

| Promoter | First ORF Sequence | TR Element | Second ORF Sequence |
|---|---|---|---|
| Tumor Specific | Reporter Gene | $TR_{drn}$ | Prodrug Activating Gene |
| Tumor Specific | Reporter Gene | $TR_{plp}$ | Prodrug Activating Gene |
| Response Gene | Reporter Gene | $TR_{drn}$ | Prodrug Activating Gene |
| Response Gene | Reporter Gene | $TR_{plp}$ | Prodrug Activating Gene |
| Constitutive | Reporter Gene | $TR_{drn}$ | Proapoptotic Gene |
| Constitutive | Reporter Gene | $TR_{plp}$ | Proapoptotic Gene |
| Inducible | Reporter Gene | $TR_{drn}$ | Proapoptotic Gene |
| Inducible | Reporter Gene | $TR_{plp}$ | Proapoptotic Gene |
| Tissue Specific | Reporter Gene | $TR_{drn}$ | Proapoptotic Gene |
| Tissue Specific | Reporter Gene | $TR_{plp}$ | Proapoptotic Gene |
| Tumor Specific | Reporter Gene | $TR_{drn}$ | Proapoptotic Gene |
| Tumor Specific | Reporter Gene | $TR_{plp}$ | Proapoptotic Gene |
| Response Gene | Reporter Gene | $TR_{drn}$ | Proapoptotic Gene |
| Response Gene | Reporter Gene | $TR_{plp}$ | Proapoptotic Gene |
| Constitutive | Cytotoxic Tumor Suppressor | $TR_{drn}$ | Reporter Gene |
| Constitutive | Cytotoxic Tumor Suppressor | $TR_{plp}$ | Reporter Gene |
| Inducible | Cytotoxic Tumor Suppressor | $TR_{drn}$ | Reporter Gene |
| Inducible | Cytotoxic Tumor Suppressor | $TR_{plp}$ | Reporter Gene |
| Tissue Specific | Cytotoxic Tumor Suppressor | $TR_{drn}$ | Reporter Gene |
| Tissue Specific | Cytotoxic Tumor Suppressor | $TR_{plp}$ | Reporter Gene |
| Tumor Specific | Cytotoxic Tumor Suppressor | $TR_{drn}$ | Reporter Gene |
| Tumor Specific | Cytotoxic Tumor Suppressor | $TR_{plp}$ | Reporter Gene |
| Response Gene | Cytotoxic Tumor Suppressor | $TR_{drn}$ | Reporter Gene |
| Response Gene | Cytotoxic Tumor Suppressor | $TR_{plp}$ | Reporter Gene |
| Constitutive | Toxin Gene | $TR_{drn}$ | Reporter Gene |
| Constitutive | Toxin Gene | $TR_{plp}$ | Reporter Gene |
| Inducible | Toxin Gene | $TR_{drn}$ | Reporter Gene |
| Inducible | Toxin Gene | $TR_{plp}$ | Reporter Gene |
| Tissue Specific | Toxin Gene | $TR_{drn}$ | Reporter Gene |
| Tissue Specific | Toxin Gene | $TR_{plp}$ | Reporter Gene |
| Tumor Specific | Toxin Gene | $TR_{drn}$ | Reporter Gene |
| Tumor Specific | Toxin Gene | $TR_{plp}$ | Reporter Gene |
| Response Gene | Toxin Gene | $TR_{drn}$ | Reporter Gene |
| Response Gene | Toxin Gene | $TR_{plp}$ | Reporter Gene |
| Constitutive | Prodrug Activating Gene | $TR_{drn}$ | Reporter Gene |
| Constitutive | Prodrug Activating Gene | $TR_{plp}$ | Reporter Gene |
| Inducible | Prodrug Activating Gene | $TR_{drn}$ | Reporter Gene |
| Inducible | Prodrug Activating Gene | $TR_{plp}$ | Reporter Gene |
| Tissue Specific | Prodrug Activating Gene | $TR_{drn}$ | Reporter Gene |
| Tissue Specific | Prodrug Activating Gene | $TR_{plp}$ | Reporter Gene |
| Tumor Specific | Prodrug Activating Gene | $TR_{drn}$ | Reporter Gene |
| Tumor Specific | Prodrug Activating Gene | $TR_{plp}$ | Reporter Gene |
| Response Gene | Prodrug Activating Gene | $TR_{drn}$ | Reporter Gene |
| Response Gene | Prodrug Activating Gene | $TR_{plp}$ | Reporter Gene |
| Constitutive | Proapoptotic Gene | $TR_{drn}$ | Reporter Gene |
| Constitutive | Proapoptotic Gene | $TR_{plp}$ | Reporter Gene |
| Inducible | Proapoptotic Gene | $TR_{drn}$ | Reporter Gene |
| Inducible | Proapoptotic Gene | $TR_{plp}$ | Reporter Gene |
| Tissue Specific | Proapoptotic Gene | $TR_{drn}$ | Reporter Gene |
| Tissue Specific | Proapoptotic Gene | $TR_{plp}$ | Reporter Gene |
| Tumor Specific | Proapoptotic Gene | $TR_{drn}$ | Reporter Gene |
| Tumor Specific | Proapoptotic Gene | $TR_{plp}$ | Reporter Gene |
| Response Gene | Proapoptotic Gene | $TR_{drn}$ | Reporter Gene |
| Response Gene | Proapoptotic Gene | $TR_{plp}$ | Reporter Gene |

Further to expression cassettes shown in Tables 1 and 2, Tables 3 and 4 below describe specific examples of monocistronic and bicistronic TR expression cassettes. One skilled in the art can readily recognize that the combinations described in Tables 3 and 4 are shown by way of example and not of limitation.

TABLE 3

Specific Examples of Monocistronic TR Expression Cassettes

| Promoter | TR Element | ORF Sequence |
|---|---|---|
| Cytomegalovirus immediate early (CMV) | $TR_{drn}$ | Firefly Luciferase |
| CMV | $TR_{plp}$ | Firefly Luciferase |
| Metallothionein-I | $TR_{drn}$ | Firefly Luciferase |
| Metallothionein-I | $TR_{plp}$ | Firefly Luciferase |
| Synapsin I | $TR_{drn}$ | Firefly Luciferase |
| Synapsin I | $TR_{plp}$ | Firefly Luciferase |
| Alpha Fetoprotein | $TR_{drn}$ | Firefly Luciferase |
| Alpha Fetoprotein | $TR_{plp}$ | Firefly Luciferase |
| Heat Shock Protein 70 | $TR_{drn}$ | Firefly Luciferase |
| Heat Shock Protein 70 | $TR_{plp}$ | Firefly Luciferase |
| CMV | $TR_{drn}$ | p53 |
| CMV | $TR_{plp}$ | p53 |

TABLE 3-continued

Specific Examples of Monocistronic TR Expression Cassettes

| Promoter | TR Element | ORF Sequence |
|---|---|---|
| Metallothionein-I | $TR_{drn}$ | p53 |
| Metallothionein-I | $TR_{plp}$ | p53 |
| Synapsin I | $TR_{drn}$ | p53 |
| Synapsin I | $TR_{plp}$ | p53 |
| Alpha Fetoprotein | $TR_{drn}$ | p53 |
| Alpha Fetoprotein | $TR_{plp}$ | p53 |
| Heat Shock Protein 70 | $TR_{drn}$ | p53 |
| Heat Shock Protein 70 | $TR_{plp}$ | p53 |
| CMV | $TR_{drn}$ | Diphtheria toxin |
| CMV | $TR_{plp}$ | Diphtheria toxin |
| Metallothionein-I | $TR_{drn}$ | Diphtheria toxin |
| Metallothionein-I | $TR_{plp}$ | Diphtheria toxin |
| Synapsin I | $TR_{drn}$ | Diphtheria toxin |
| Synapsin I | $TR_{plp}$ | Diptithena toxin |
| Alpha Fetoprotein | $TR_{drn}$ | Diphtheria toxin |
| Alpha Fetoprotein | $TR_{plp}$ | Diphtheria toxin |
| Heat Shock Protein 70 | $TR_{drn}$ | Diphtheria toxin |
| Heat Shock Protein 70 | $TR_{plp}$ | Diphtheria toxin |
| CMV | $TR_{drn}$ | Thymidrae Kinase sr39 |
| CMV | $TR_{plp}$ | Thymidine Kinase sr39 |
| Metallothionein-I | $TR_{drn}$ | Thymidine Kinase sr39 |
| Metallothionein-I | $TR_{plp}$ | Thymidine Kinase sr39 |
| Synapsin I | $TR_{drn}$ | Thymidine Kinase sr39 |
| Synapsin I | $TR_{plp}$ | Thymidine Kinase sr39 |
| Alpha Fetoprotein | $TR_{drn}$ | Thymidine Kinase sr39 |
| Alpha Fetoprotein | $TR_{plp}$ | Thymidine Kinase sr39 |
| Heat Shock Protein 70 | $TR_{drn}$ | Thymidine Kinase sr39 |
| Heat Shock Protein 70 | $TR_{plp}$ | Thymidine Kinase sr39 |
| CMV | $TR_{drn}$ | Caspase 3 |
| CMV | $TR_{plp}$ | Caspase 3 |
| Metallothionein-I | $TR_{drn}$ | Caspase 3 |
| Metallothionein-I | $TR_{plp}$ | Caspase 3 |
| Synapsin I | $TR_{drn}$ | Caspase 3 |
| Synapsin I | $TR_{plp}$ | Caspase 3 |
| Alpha Fetoprotein | $TR_{drn}$ | Caspase 3 |
| Alpha Fetoprotein | $TR_{plp}$ | Caspase 3 |
| Heat Shock Protein 70 | $TR_{drn}$ | Caspase 3 |
| Heat Shock Protein 70 | $TR_{plp}$ | Caspase 3 |

TABLE 4

Specific Examples of Bicistronic TR Expression Cassettes

| Promoter | First ORF Sequence | TR Element | Second ORF Sequence |
|---|---|---|---|
| CMV | Renilla Luciferase | $TR_{drn}$ | Firefly Luciferase |
| CMV | Renilla Luciferase | $TR_{plp}$ | Firefly Luciferase |
| Metallothionein-I | Renilla Luciferase | $TR_{drn}$ | Firefly Luciferase |
| Metallothionein-I | Renilla Luciferase | $TR_{plp}$ | Firefly Luciferase |
| Synapsin I | Renilla Luciferase | $TR_{drn}$ | Firefly Luciferase |
| Synapsin I | Renilla Luciferase | $TR_{plp}$ | Firefly Luciferase |
| Alpha Fetoprotein | Renilla Luciferase | $TR_{drn}$ | Firefly Luciferase |
| Alpha Fetoprotein | Renilla Luciferase | $TR_{plp}$ | Firefly Luciferase |
| Heat Shock Protein 70 | Renilla Luciferase | $TR_{drn}$ | Firefly Luciferase |
| Heat Shock Protein 70 | Renilla Luciferase | $TR_{plp}$ | Firefly Luciferase |
| CMV | p53 | $TR_{drn}$ | Firefly Luciferase |
| CMV | p53 | $TR_{plp}$ | Firefly Luciferase |
| Metallothionein-I | p53 | $TR_{drn}$ | Firefly Luciferase |
| Metallothionein-I | p53 | $TR_{plp}$ | Firefly Luciferase |
| Synapsin I | p53 | $TR_{drn}$ | Firefly Luciferase |
| Synapsin I | p53 | $TR_{plp}$ | Firefly Luciferase |
| Alpha Fetoprotein | p53 | $TR_{drn}$ | Firefly Luciferase |
| Alpha Fetoprotein | p53 | $TR_{plp}$ | Firefly Luciferase |
| Heat Shock Protein 70 | p53 | $TR_{drn}$ | Firefly Luciferase |
| Heat Shock Protein 70 | p53 | $TR_{plp}$ | Firefly Luciferase |
| CMV | Diphtheria toxin | $TR_{drn}$ | Firefly Luciferase |
| CMV | Diphtheria toxin | $TR_{plp}$ | Firefly Luciferase |
| Metallothionein-I | Diphtheria toxin | $TR_{drn}$ | Firefly Luciferase |
| Metallothionein-I | Diphtheria toxin | $TR_{plp}$ | Firefly Luciferase |
| Synapsin I | Diphtheria toxin | $TR_{drn}$ | Firefly Luciferase |
| Synapsin I | Diphtheria toxin | $TR_{plp}$ | Firefly Luciferase |
| Alpha Fetoprotein | Diphtheria toxin | $TR_{drn}$ | Firefly Luciferase |
| Alpha Fetoprotein | Diphtheria toxin | $TR_{plp}$ | Firefly Luciferase |
| Heat Shock Protein 70 | Diphtheria toxin | $TR_{drn}$ | Firefly Luciferase |
| Heat Shock Protein 70 | Diphtheria toxin | $TR_{plp}$ | Firefly Luciferase |
| CMV | Thymidine Kinase sr39 | $TR_{drn}$ | Firefly Luciferase |
| CMV | Thymidine Kinase sr39 | $TR_{plp}$ | Firefly Luciferase |
| Metallothionein-I | Thymidine Kinase sr39 | $TR_{drn}$ | Firefly Luciferase |
| Metallothionein-I | Thymidine Kinase sr39 | $TR_{plp}$ | Firefly Luciferase |
| Synapsin I | Thymidine Kinase sr39 | $TR_{drn}$ | Firefly Luciferase |
| Synapsin I | Thymidine Kinase sr39 | $TR_{plp}$ | Firefly Luciferase |
| Alpha Fetoprotein | Thymidine Kinase sr39 | $TR_{drn}$ | Firefly Luciferase |
| Alpha Fetoprotein | Thymidine Kinase sr39 | $TR_{plp}$ | Firefly Luciferase |
| Heat Shock Protein 70 | Thymidine Kinase sr39 | $TR_{drn}$ | Firefly Luciferase |
| Heat Shock Protein 70 | Thymidine Kinase sr39 | $TR_{plp}$ | Firefly Luciferase |
| CMV | Caspase 3 | $TR_{drn}$ | Firefly Luciferase |
| CMV | Caspase 3 | $TR_{plp}$ | Firefly Luciferase |
| Metallothionein-I | Caspase 3 | $TR_{drn}$ | Firefly Luciferase |
| Metallothionein-I | Caspase 3 | $TR_{plp}$ | Firefly Luciferase |
| Synapsin I | Caspase 3 | $TR_{drn}$ | Firefly Luciferase |
| Synapsin I | Caspase 3 | $TR_{plp}$ | Firefly Luciferase |

TABLE 4-continued

Specific Examples of Bicistronic TR Expression Cassettes

| Promoter | First ORF Sequence | TR Element | Second ORF Sequence |
|---|---|---|---|
| Alpha Fetoprotein | Caspase 3 | $TR_{drn}$ | Firefly Luciferase |
| Alpha Fetoprotein | Caspase 3 | $TR_{plp}$ | Firefly Luciferase |
| Heat Shock Protein 70 | Caspase 3 | $TR_{drn}$ | Firefly Luciferase |
| Heat Shock Protein 70 | Caspase 3 | $TR_{plp}$ | Firefly Luciferase |
| CMV | Renilla Luciferase | $TR_{drn}$ | p53 |
| CMV | Renilla Luciferase | $TR_{plp}$ | p53 |
| Metallothionein-I | Renilla Luciferase | $TR_{drn}$ | p53 |
| Metallothionein-I | Renilla Luciferase | $TR_{plp}$ | p53 |
| Synapsin I | Renilla Luciferase | $TR_{drn}$ | p53 |
| Synapsin I | Renilla Luciferase | $TR_{plp}$ | p53 |
| Alpha Fetoprotein | Renilla Luciferase | $TR_{drn}$ | p53 |
| Alpha Fetoprotein | Renilla Luciferase | $TR_{plp}$ | p53 |
| Heat Shock Protein 70 | Renilla Luciferase | $TR_{drn}$ | p53 |
| Heat Shock Protein 70 | Renilla Luciferase | $TR_{plp}$ | p53 |
| CMV | Renilla Luciferase | $TR_{drn}$ | Diphtheria toxin |
| CMV | Renilla Luciferase | $TR_{plp}$ | Diphtheria toxin |
| Metallothionein-I | Renilla Luciferase | $TR_{drn}$ | Diphtheria toxin |
| Metallothionein-I | Renilla Luciferase | $TR_{plp}$ | Diphtheria toxin |
| Synapsin I | Renilla Luciferase | $TR_{drn}$ | Diphtheria toxin |
| Synapsin I | Renilla Luciferase | $TR_{plp}$ | Diphtheria toxin |
| Alpha Fetoprotein | Renilla Luciferase | $TR_{drn}$ | Diphtheria toxin |
| Alpha Fetoprotein | Renilla Luciferase | $TR_{plp}$ | Diphtheria toxin |
| Heat Shock Protein 70 | Renilla Luciferase | $TR_{drn}$ | Diphtheria toxin |
| Heat Shock Protein 70 | Renilla Luciferase | $TR_{plp}$ | Diphtheria toxin |
| CMV | Renilla Luciferase | $TR_{drn}$ | Thymidine Kinase sr39 |
| CMV | Renilla Luciferase | $TR_{plp}$ | Thymidine Kinase sr39 |
| Metallothionein-I | Renilla Luciferase | $TR_{drn}$ | Thymidine Kinase sr39 |
| Metallothionein-I | Renilla Luciferase | $TR_{plp}$ | Thymidine Kinase sr39 |
| Synapsin I | Renilla Luciferase | $TR_{drn}$ | Thymidine Kinase sr39 |
| Synapsin I | Renilla Luciferase | $TR_{plp}$ | Thymidine Kinase sr39 |
| Alpha Fetoprotein | Renilla Luciferase | $TR_{drn}$ | Thymidine Kinase sr39 |
| Alpha Fetoprotein | Renilla Luciferase | $TR_{plp}$ | Thymidine Kinase sr39 |
| Heat Shock Protein 70 | Renilla Luciferase | $TR_{drn}$ | Thymidine Kinase sr39 |
| Heat Shock Protein 70 | Renilla Luciferase | $TR_{plp}$ | Thymidine Kinase sr39 |
| CMV | Renilla Luciferase | $TR_{drn}$ | Caspase 3 |
| CMV | Renilla Luciferase | $TR_{plp}$ | Caspase 3 |
| Metallothionein-I | Renilla Luciferase | $TR_{drn}$ | Caspase 3 |
| Metallothionein-I | Renilla Luciferase | $TR_{plp}$ | Caspase 3 |
| Synapsin I | Renilla Luciferase | $TR_{drn}$ | Caspase 3 |
| Synapsin I | Renilla Luciferase | $TR_{plp}$ | Caspase 3 |
| Alpha Fetoprotein | Renilla Luciferase | $TR_{drn}$ | Caspase 3 |
| Alpha Fetoprotein | Renilla Luciferase | $TR_{plp}$ | Caspase 3 |
| Heat Shock Protein 70 | Renilla Luciferase | $TR_{drn}$ | Caspase 3 |
| Heat Shock Protein 70 | Renilla Luciferase | $TR_{plp}$ | Caspase 3 |

General Methods

Molecular biological techniques, biochemical techniques, and microorganism techniques as used herein are well known in the art and commonly used, and are described in, for example, Sambrook J. et al. (1989), Molecular Cloning: A Laboratory Manual, Cold Spring Harbor and its 3rd Ed. (2001); Ausubel, F. M. (1987), Current Protocols in Molecular Biology, Greene Pub. Associates and Wiley-interscience; Ausubel, F. M. (1989), Short Protocols in Molecular Biology: A Compendium of Methods from Current Protocols in Molecular Biology, Greene Pub. Associates and Wiley-interscience; Innis, M. A. (1990), PCR Protocols: A Guide to Methods and Applications, Academic Press; Ausubel, F. M. (1992), Short Protocols in Molecular Biology: A Compendium of Methods from Current Protocols in Molecular Biology, Greene Pub. Associates; Ausubel, F. M. (1995), Short Protocols in Molecular Biology: A Compendium of Methods from Current Protocols in Molecular Biology, Greene Pub. Associates; Innis, M. A. et al. (1995), PCR Strategies, Academic Press; Ausubel, F. M. (1999), Short Protocols in Molecular Biology: A Compendium of Methods from Current Protocols in Molecular Biology, Wiley, and annual updates; Sninsky, J. J. et al. (1999), PCR Applications: Protocols for Functional Genomics, Academic Press; Special issue, Jikken Igaku [Experimental Medicine] "Idenshi Donyu & Hatsugenkaiseki Jikkenho [Experimental Method for Gene introduction & Expression Analysis]", Yodo-sha, 1997; and the like. Relevant portions (or possibly the entirety) of each of these publications are herein incorporated by reference.

Any technique may be used herein for introduction of a nucleic acid molecule into cells, including, for example, transformation, transduction, transfection, and the like. Such a nucleic acid molecule introduction technique is well known in the art and commonly used, and is described in, for example, Ausubel F. A. et al., editors, (1988), Current Protocols in Molecular Biology, Wiley, New York, N.Y.; Sambrook J. et al. (1987) Molecular Cloning: A Laboratory Manual, 2nd Ed. and its 3rd Ed., Cold Spring Harbor Laboratory Press, Cold Spring Harbor, N.Y.; Special issue, Jikken Igaku [Experimental Medicine] Experimental Method for Gene introduction & Expression Analysis", Yodo-sha, 1997; and the like. Gene introduction can be confirmed by method as described herein, such as Northern blotting analysis and Western blotting analysis, or other well-known, common techniques.

Amino acid deletion, substitution or addition of the polypeptide of the present technology can be carried out by a site-specific mutagenesis method which is a well known technique. One or several amino acid deletions, substitutions or additions can be carried out in accordance with methods described in Molecular Cloning, A Laboratory Manual, Second Edition, Cold Spring Harbor Laboratory Press (1989); Current Protocols in Molecular Biology, Supplement 1 to 38, John Wiley & Sons (1987-1997); Nucleic Acids Research, 10, 6487 (1982); Proc. Natl. Acad. Sci., USA, 79, 6409 (1982); Gene, 34, 315 (1985); Nucleic Acids Research, 13, 4431 (1985); Proc. Natl. Acad. Sci. USA, 82, 488 (1985); Proc. Natl. Acad. Sci., USA, 81, 5662 (1984); Science, 224, 1431 (1984); PCT WO85/00817 (1985); Nature, 316, 601 (1985); and the like.

EXAMPLES

The following non-limiting examples are provided to further illustrate the present technology. It should be appreciated by those of skill in the art that the techniques disclosed in the examples that follow represent approaches the inventors have found function well in the practice of the technology, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the technology.

Example I

Construction of the Monocistronic TR Cassette

This example describes the preparation of mammalian expression vectors containing a "monocistronic" cassette (FIG. 2) which allows selective translation of open reading frames (ORFs) under the control of the Translational Regulator (TR) sequence during cell stress and death. The pTR-ORF plasmid construct described in this example contains a mammalian promoter, a TR element operably linked to a single protein coding sequence, as well as a mRNA polyadenylation signal (i.e., the TR expression cassette).

A. Preparation of the TR Regulated Expression Cassette

In order to demonstrate the feasibility and efficacy of TR regulated translation, an initial series of mammalian expression vectors are prepared containing a TR expression cassette. The pTR-EYFP expression vectors are constructed essentially as follows. DNA fragments corresponding to sequences −16 to +858 of the PLP and DM20 cDNAs are cloned into the pEYFP-N1 vector generating the pPLPeyfp and pDM20eyfp expression vectors (FIG. 1). The mammalian expression sequences of the pEYFP-N1 plasmid contain the CMV early promoter/enhancer, the EYFP ORF and the SV40 early polyadenylation signal. Other mammalian-specific elements in the pEYFP-N1 backbone include an SV40 origin of replication, a cassette consisting of the SV40 early (Large T) gene promoter fused to the neomycin phosphotransferase gene and polyadenylation signals from the herpes simplex thymidine kinase gene. The neomycin resistance provided by this expression cassette can be used as a selectable marker for preparing stably transformed mammalian cells. For selection and growth in E. coli, a bacterial promoter upstream of the SV40 promoter provides kanamycin resistance, whereas, a pUC19 origin of replication allows plasmid propagation in E. coli.

The initial round of oligonucleotide site directed mutagenesis, of the pPLPeyfp and pDM20eyfp expression vectors, use internal oligonucleotide primer sets [L205.5w (SEQ ID NO: 7) and L205.3w (SEQ ID NO: 8); L235.5 (SEQ ID NO: 9) and L235.3 (SEQ ID NO: 10)] to remove the translation initation codons at nucleotides 511 and 598 in the $TR_{dm}$ sequence and nucleotides 616 and 703 in the $TR_{plp}$ sequence, respectively. The mutagenesis procedure used in this effort is as described for the QuikChange mutagenesis of the TK ORF, see subsequent section. An ensuing mutation, using a 5'-specific primer set [RI-stop_s (SEQ ID NO: 11) and RI-stop_a (SEQ ID NO: 12)] alters both TR sequences so that capdependent translation was eliminated by the insertion of stop codons and the removal of 5' proximal AUG initiation codons. Subsequently, a 3'-specific primer set [H-Xh-Xb_s (SEQ ID NO: 13) and H-Xh-Xb_a (SEQ ID NO: 14) removes the PLP/DM20 translation termination codon and introduces HindIII, XhoI, and XbaI sites into the intervening sequences between the TR sequence and EYFP AUG codon. Procedures for site-directed mutagenesis are well known in the art (for example, QuikChange Mutagenesis Kit, Stratagene) and are discussed in a subsequent section of this example. These constructs are designated $pTR_{plp}$-EYFP and $pTR_{dm}$-EYFP (FIG. 2). Thus the TR expression cassette in the $pTR_{plp}$-EYFP plasmid is composed of the CMV immediate early promoter/enhancer, the PLP TR sequence, the EYFP ORF and the SV40 polyadenylation signal. Similarly, the TR expression cassette in the $pTR_{dm}$-EYFP plasmid contains the CMV promoter/enhancer, the DM20 TR sequence, the EFYP ORF and the SV40 polyadenylation signal.

The sequence identity of these constructs and subsequent derivatives are verified using any or all of the following sequencing primers; SK15 (SEQ ID NO: 15), SK16 (SEQ ID NO: 16), SK17 (SEQ ID NO: 17), EYFP(−)1 (SEQ ID NO: 18), EYFP(−)$_2$ (SEQ ID NO: 19), BAC-1 (SEQ ID NO: 20), BAC-2 (SEQ ID NO: 21) or BAC-3 (SEQ ID NO: 22).

B. Selection and Cloning of ORFs into the TR Cassette

To demonstrate TR regulation of a variety of ORFs, a number of different plasmids are created by varying the TR regulated ORF. Derivatives of the monocistronic $pTR_{plp/dm}$-EYFP plasmids are used to construct other monocistronic TR-ORF vectors by modifying some or all of these functional elements, including (a) exchanging the pCMV 1E promoter, (b) removing the EYFP ORF, and/or (c) addition or subtraction of restriction sites as needed. To clone the non-EYFP ORFs into the same position as the EYFP ORF, two nucleotides are inserted upstream of the H-Xh-Xb sequence using site directed mutagenesis with the AUGback_s (SEQ ID NO: 23) and AUGback_a (SEQ ID NO: 24) primer set. This allows subsequent ORF-specific PCR primer sets to include 1) a common 5' sequence which replaced the native translational initiation codon with an identical Kozak consensus sequence and 2) 5' HindIII and 3' XhoI restriction enzyme sites which allowed directional cloning. Following digestion with HindIII and XhoI, these ORF-specific PCR fragments are cloned into the $pTR_{plp}$-ORF and $pTR_{dm}$-ORF vectors. The EYFP, fLuc, TK, CAT and LacZ ORFs are PCR amplified from the pEYFP-N1 (Clontech), phCMV-LUC-FSR (Genlantis), pHSV106 (GenBank sequence V00470), pCAT-Enhancer (Promega), and pAAV-LacZ (Stratagene) plasmid vectors, respectively. The following exemplary plasmids are made:

$pTR_{plp}$-fLuc, which includes the plp TR element and the firefly Luciferase (fLUC) ORF that was PCR amplified using the Luc-1 (SEQ ID NO: 25) and Luc-2 (SEQ ID NO: 26) primer set;

$pTR_{dm}$-fLuc, which includes the dm20 TR element and the fLUC ORF that was PCR amplified using the Luc-1 and Luc-2 primer set;

pTR$_{plp}$-TK, which includes the plp TR element and the HSV thymidine kinase (TK) ORF that was PCR amplified using the TK-1 (SEQ ID NO: 27) and TK-2 (SEQ ID NO: 28) primer set;

pTR$_{dm}$-TK, which includes the dm20 TR element and the TK ORF that was PCR amplified using the TK-1 and TK-2 primer set;

pTR$_{plp}$-CAT, which includes the plp TR element and the bacterial choramphenicol acetyltransferase (CAT) ORF that was PCR amplified using the CAT-1 (SEQ ID NO: 29) and the CAT-2 (SEQ ID NO: 30) primer set;

pTR$_{dm}$-CAT, which includes the dm20 TR sequence and the CAT ORF that was PCR amplified using the CAT-1 and the CAT-2 primer set;

pTR$_{plp}$-LacZ, which includes the plp TR sequence and the bacterial LacZ ORF encoding the beta-galactosidase protein that was PCR amplified using the LacZ-1 (SEQ ID NO: 31) and LacZ-2 (SEQ ID NO: 32) primer set; and pTR$_{dm}$-LacZ, which includes the dm20 TR element and the LacZ ORF that was PCR amplified using the LacZ-1 and LacZ-2 primer set.

C. Site Directed Mutagenesis of the TR-Regulated ORFs

This example shows that the TR-regulated ORF can be altered to improve a functional characteristic of a protein translated from the TR cassette or eliminate any RNA sequence/structure that might interfere with TR regulation. In this example, the five TK sr39 amino acid mutations (Gambhir et al; Proc Natl Acad Sci USA; 97: 2785-2790) are inserted into the TK ORF using the Sr39-1 (SEQ ID NO: 33) and Sr39-2 primer set (SEQ ID NO: 34).

Compared to the wildtype TK protein, the TKsr39 protein displays beneficial kinetic properties, such as enhanced pro-drug binding (83-fold higher than the wildtype protein for GCV), increased pro-drug mediated cell killing at lower pro-drug concentrations, and superior binding of metabolic tracers (for example 18F-labeled penciclovir). In the latter case, this enhanced binding efficiency improves noninvasive imaging techniques such as positron emission tomography.

To validate the process of site directed mutagenesis in the TR cassette and produce an improved TK marker protein, oligonucleotide directed mutagenesis is used to insert the TKsr39 DNA mutations into the wild type TR-ORF sequence. Procedures for site-directed mutagenesis are well known in the art (for example, QuikChange Site-Directed Mutagenesis Kits, Stratagene). Basically, oligonucleotide primers (e.g. Sr39-1 and Sr39-2) were constructed that contained the desired mutations. PCR amplification of the pTR$_{plp}$-TK and pTR$_{dm}$, TK templates with the Sr39 primer set (1 cycle of 95° C. for 30 sec, 12 cycles of 95° C. for 30 sec, 55° C. for 1 min, 68° C. for 12 min) incorporated the mutations into the exponentially amplified DNA strand. Following amplification, the DNA is digested with the DpnI restriction enzyme which specifically recognizes methylated and hemi-methylated DNA. Since the pTR$_{plp}$-TK and pTR$_{dm}$-TK templates were grown in a methylation-positive bacterial strain, DpnI digestion removed the parental template prior to bacterial transformation. The transformed bacteria are plated on selective media and isolated colonies used to prepare DNA minipreps which are analyzed by restriction mapping and DNA sequencing.

The resultant plasmids are termed pTR$_{plp}$-TKsr39 and pTR$_{dm}$-TKsr39. The pTR$_{plp}$-TKsr39 vector includes the plp TR element and the HSV-1 TKsr39 mutations in the pHSV106 TK ORF (SEQ ID NO: 39). Similarly, the pTR$_{dm}$-TKsr39 plasmid contains the dm20 TR element and the TKsr39 mutations in the pHSV 106 TK ORF (SEQ ID NO: 40).

Example II

Construction of a Bicistronic TR Cassette

This example describes the preparation of mammalian expression vectors containing a bicistronic TR cassette (FIG. 3) which allows cap-dependent translation of an ORF upstream of the TR cassette and cap-independent translation of an ORF under the control of the Translational Regulator (TR) element during cell stress and death. These vectors allow the examination of cap-dependent and cap-independent translational processes from a single mRNA.

A. Inserting the Firefly Luciferase ORF Upstream of the TR-EYFP Cassette

Bicistronic vectors are constructed by inserting the Firefly Luciferase (fLuc) ORF (termed ORF2) upstream of the TR cassette containing the EYFP gene (ORF1). The phCMV-LUC-FSR vector (Genlantis) are digested with EcoRI, the restriction fragment containing the fLuc sequence purified and cloned into the EcoRI site of the pTR$_{plp}$-EYFP and pTR$_{dm}$-EYFP vectors (FIG. 3). The orientation of the fLuc ORF is verified by restriction mapping and forward (sense) and reverse (antisense) inserts are recovered. The sense vectors are termed the pfLuc-TR$_{plp}$-EYFP and pfLuc-TR$_{dm}$-EYFP plasmids and the antisense vectors are termed the pcuLf-TR$_{plp}$-EYFP and pcuLf-TR$_{dm}$-EYFP plasmids The sense pORF-TR-ORF vectors encode a single mRNA species that allows constitutive steady-state cap-dependent translation of the upstream ORF and selective cap-independent translation of the ORF operatively linked to the TR element during cell stress and death. The antisense bicistronic vectors serve as a control for TR activity by providing a large segment of upstream mRNA sequences which structurally block cap-dependent translation of the TR-regulated ORF in normal cells. Protein synthesis from the antisense vectors in stressed and dying cells is TR-regulated cap-independent translation.

For example, the pfLuc-TRplp-EYFP vector encodes a single mRNA species that constitutively exhibits cap-dependent translation of the fLuc ORF and selective cap-independent translation of the EYFP ORF from the plp TR element during cell stress and death. Similarly, a single mRNA species is transcribed from the pfLuc-TR$_{dm}$-EYFP cassette that provides cap-dependent translation of the fLUC ORF and cap-independent translation of the EYFP ORF from the dm20 TR element during cell stress and death (FIG. 4).

Example III

Construction and Production of Recombinant Viral Vectors for Expression of TR Cassettes in Mammalian Cells Recombinant adenovirus-associated virus (rAAV) and baculovirus (rBAC) vectors are designed to produce infectious virions that can transduce mammalian cells with the TR expression cassette. For illustration, a series of rAAV and rBAC viruses are prepared that direct constitutive expression of TR expression cassettes in mammalian cells from the CMV-IE promoter/enhancer.

A. Inserting the TR Cassettes into Recombinant AAV (rAAV) Virions

The pAAV-TR$_{plp}$ and pAAV-TR$_{dm}$ transfer (or shuttle) vectors are derived from the pAAV-MCS vector (Stratagene). To allow bacterial propagation, the pAAV-MCS backbone provides (1) the bacterial beta-lactamase gene, (2) the pUC19 origin of replication, and (3) the f1 replication origin for single-stranded DNA synthesis. For AAV viral production and mammalian gene expression, the pAAV-MCS plasmid contains the Left and Right adeno-associated virus-2 (AAV2) inverted terminal repeats (ITRs) flanking the CMV IE promoter/enhancer, the CMV IE transcriptional start site, the beta-globin intron, multiple unique restriction sites for cloning (multiple cloning site or MCS), and the human growth hormone polyadenylation signal (FIG. 5).

The TR-ORF cassettes are produced by digesting the appropriate TR-ORF expression plasmid with EcoRI/XhoI and cloning into the EcoRI/XhoI sites of the pAAV-MCS vector. For example, the pTR$_{plp}$-fLUC and pTR$_{dm}$-fLUC plasmids can be digested with EcoRI/XhoI and cloned into the EcoRI/XhoI sites of the pAAV-MCS vector to create the pAAV-TR-LUC shuttle vectors listed below.

Following restriction mapping and/or DNA sequencing, the following examples of pAAV-TR-ORF shuttle vectors can be produced:

pAAV-TR$_{plp}$-EYFP, which contains the plp TR sequence and the EYFP ORF;

pAAV-TR$_{dm}$-EYFP, which contains the dm20 TR element and the EYFP ORF;

pAAV-TR$_{plp}$-fLuc, which contains the plp TR element and the firefly Luciferase ORF;

pAAV-TR$_{dm}$-fLuc, which contains the dm20 TR sequence and the fLUC ORF;

pAAV-TR$_{plp}$-TK, which contains the plp TR element and the HSV-1 TK ORF;

pAAV-TR$_{dm}$-TK, which contains the dm20 TR element and the HSV-1 TK ORF;

pAAV-TR$_{plp}$-TKsr39, which contains the plp TR sequence and the sr39 derivative of the HSV-1 TK ORF;

pAAV-TR$_{dm}$-TKsr39, which contains the dm20 TR element and the sr39 derivative of the HSV-1 TK ORF;

pAAV-TR$_{plp}$-CAT, which contains the plp TR element and the bacterial chloramphenicol acetyltransferase (CAT) ORF;

pAAV-TR$_{dm}$-CAT, which contains the dm20 TR sequence and the CAT ORF;

pAAV-TR$_{plp}$-LacZ, which contains the plp TR sequence and the bacterial LacZ ORF; and pAAV-TR$_{dm}$-LacZ, which contains the dm20 TR element and the LacZ ORF.

To recover recombinant AAV2 viral particles, HEK293 cells are transfected using the triple plasmid transfection procedure that requires a pAAV shuttle vector, the pAAV-RC (replication competent helper plasmid) and the pHelper (adenovirus helper plasmid). The rAAV 3-plasmid procedure is well known in the art and is briefly described below. The pAAV shuttle vector is cotransfected into a packaging cell line along with the 7.3-kb pAAV-RC vector and the 11.6-kb pHelper vector. The pAAV-RC vector encodes the rep (DNA replication protein) and cap (the AAV2 capsid protein) genes, which are required for infectious virions. The pHelper vector contains a deleted Adenovirus genome that expresses various adenovirus genes required for AAV production. Genetic complementation between proteins expressed from the three plasmids and the adenovirus E1A and E1B proteins (provided by the HEK293 cells) allows the generation of packaged virions following recombination at the left and right inverted terminal repeats (L-ITR and R-ITR) in the pAAV shuttle vector.

For this example, HEK293 cells are transfected with 15 micrograms of a pAAV-TR-ORF shuttle vector or 15 micrograms of the pAAV-PLP/DM20eyfp plasmids, 10 micrograms of the pAAV-RC plasmid, and 10 micrograms of the pHelper vector using a standard calcium phosphate transfection protocol. Following transfection, the HEK293 cells are incubated for 72 hrs total. At this time, the cells are collected, the medium removed and a lysate produced using three freeze-thaw cycles. Clarified lysates are prepared by centrifugation at 2500 rpm for 10 min.

Specific examples of rAAV-TR-ORF viruses that can be generated in this manner include:

rAAV-TR$_{plp}$-EYFP, which contains the plp TR element operatively linked to the EYFP ORF;

rAAV-TR$_{dm}$-EYFP, which contains the dm20 TR sequence linked to the EYFP ORF;

rAAV-TR$_{plp}$-fLuc, which includes the plp TR element and the firefly Luciferase ORF;

rAAV-TR$_{dm}$-fLuc, which contains the dm20 TR sequence and the fLUC ORF;

rAAV-TR$_{plp}$-TK, which contains the plp TR element and the HSV-1 TK ORF;

rAAV-TR$_{dm}$-TK, which contains the dm20 TR element and the HSV-1 TK ORF;

rAAV-TR$_{plp}$-TKsr39, which contains the pip TR sequence and the sr39 derivative of the HSV-1 TK ORF;

rAAV-TR$_{dm}$-TKsr39, which contains the dm20 TR element and the sr39 derivative of the HSV-1 TK ORF;

rAAV-TR$_{plp}$-CAT, which contains the plp TR element and the CAT ORF;

rAAV-TR$_{dm}$-CAT, which contains the dm20 TR sequence and the CAT ORF;

rAAV-TR$_{plp}$-LacZ, which contains the plp TR sequence and the bacterial LacZ ORF; and rAAV-TR$_{dm}$-LacZ, which contains the dm20 TR element and the LacZ ORF.

B. Preparation of Recombinant Baculovirus (rBAC) Virions Transducing the TR Expression Cassette A set of mammalian expression vectors are prepared using the pBAC-1 shuttle transfer backbone (Novagen). The commercial pBAC™-1 vector is a baculovirus transfer plasmid designed for cloning and expressing recombinant proteins in insect cells using the polh promoter. The commercial pBAC-1 plasmid contains (1) the bacterial beta-lactamase gene, as well as (2) the pUC19 origin of replication and (3) the f1 origin of replication (FIG. 5). The vector also contains the polh promoter and a series of unique restriction sites commonly used to clone ORFs for expression in insect cells. Flanking the insect expression elements are baculovirus sequences needed for DNA recombination, the late expression factor 2 (lef-2) and the open reading frame 1629 (orf1629) genes. Transfecting insect cells with a pBAC shuttle vector and replication deficient baculoviral DNA allows recombination between the lef-2/orf1629 shuttle vector sequences with homologous sequences in the viral DNA and the generation of a replication competent recombinant virus.

To provide mammalian expression, the viral polh promoter and polh transcription initiation site are removed by ligating the pBAC-1 vector digested with BglII and BamHI, thus producing the pBAC polh-plasmid. For this example, the CMV IE promoter/enhancer is PCR amplified using the oligonucleotide primer set [CMV-1 (SEQ ID NO: 35) and CMV-2 (SEQ ID NO: 36)] which introduces a 5' StuI site and a 3' EcoRI site into the PCR fragment. The amplified DNA is cut with StuI and EcoRI and directionally cloned into the StuI/EcoRI sites of the pBAC polh-vector, resulting in the pBAC-CMV plasmid. To introduce a mRNA polyadenylation signal, two complementary oligonucleotides [PolyA-1 (SEQ ID NO: 37) and PolyA-2 (SEQ ID NO: 38)] containing the SV40 early polyadenylation signal flanked by AvrII and SphI restriction sites are annealed and cloned into the AvrII/SphI sites of the pBAC-CMV vector to create the pBAC-CMV-PolyA plasmid.

The TR-ORF cassettes are removed from the pTR$_{plp}$-EYFP and pTR$_{dm}$-EYFP plasmids with EcoRI/NotI and cloned into the EcoRI/NotI sites of the pBAC-CMV-PolyA vector to create the pBAC shuttle vectors listed below. In a related procedure, the other pBAC shuttle vectors listed below are produced by digesting the appropriate TR-ORF expression plasmid with EcoRI/XhoI and cloning into the EcoRI/XhoI sites of the pBAC-CMV-PolyA vector.

Following restriction mapping and/or DNA sequencing, the following specific examples of pBAC-TR-ORF shuttle vectors are produced:

pBAC-TR$_{plp}$-EYFP, which contains the plp TR sequence and the EYFP ORF;

pBAC-TR$_{dm}$-EYFP, which includes the dm20 TR element and the EYFP ORF;

pBAC-TR$_{plp}$-fLuc, which includes the plp TR element and the firefly Luciferase ORF;

pBAC-TR$_{dm}$-fLuc, which contains the dm20 TR sequence and the fLUC ORF;

pBAC-TR$_{plp}$-TK, which contains the plp TR element and the HSV-1 TK ORF;

pBAC-TR$_{dm}$-TK, which contains the dm20 TR element and the HSV-1 TK ORF;

pBAC-TR$_{plp}$-TKsr39, which contains the plp TR sequence and the sr39 derivative of the HSV-1 TK ORF;

pBAC-TR$_{dm}$-TKsr39, which contains the dm20 TR element and the sr39 derivative of the HSV-1 TK ORF;

pBAC-TR$_{plp}$-CAT, which contains the plp TR element and the bacterial chloramphenicol acetyltransferase (CAT) ORF;

pBAC-TR$_{dm}$-CAT, which contains the dm20 TR sequence and the CAT ORF;

pBAC-TR$_{plp}$-LacZ, which includes the plp TR sequence and the bacterial LacZ ORF; and pBAC-TR$_{dm}$-LacZ, which includes the dm20 TR element and the LacZ ORF.

The methods for producing infectious rBAC virions are well known in the art. Briefly, the process can be described as outlined below. Recovery of recombinant baculovirus particles was accomplished by transfection of *Spodoptera frugiperda* (Sf9) cells with the pBAC-TR shuttle vector and BacVector-2000 (or BacVector-3000) Triple Cut Virus DNA (Novagen). Genetic recombination results in insertion of the CMV-TR cassette into the baculovirus genome and packaging into BAC virions. In this example, 500 ng of shuttle vector was mixed with 100 ng of BacVector Triple Cut Virus DNA and transfected into 500,000 Sf-9 cells for 1 hour using the Insect GeneJuice Transfection Reagent (Novagen). Cells were washed in serum free BacVector Insect Cell Medium and overlaid with complete medium (containing 5% fetal bovine serum) for 4-5 days. At this time, the cells were collected in the media overlay and pelleted by centrifugation at 2000 rpm for 10 min. This primary viral media stock was transferred to sterile tubes and stored at 4 C. High titer rBAC viral stocks (termed secondary or tertiary stocks) were prepared by low titer infections of Sf-9 cells (infectivity of 0.1 pfu/cell) using the media overlay procedure described above. rBAC titers were determined by standard plaque overlay techniques. Restriction mapping of rBAC viral DNA preparations was used to verify viral integrity and composition.

Specific examples of rBAC-TR-ORF viruses that can be generated in this manner include:

rBAC-TR$_{plp}$-EYFP, which includes the plp TR element operatively linked to the EYFP ORF;

rBAC-TR$_{dm}$-EYFP, which includes the dm20 TR sequence linked to the EYFP ORF;

rBAC-TR$_{plp}$-fLuc, which includes the plp TR element and the firefly Luciferase ORF;

rBAC-TR$_{dm}$-fLuc, which contains the dm20 TR sequence and the fLUC ORF;

rBAC-TR$_{plp}$-TK, which contains the plp TR element and the HSV-1 TK ORF;

rBAC-TR$_{dm}$-TK, which contains the dm20 TR element and the HSV-1 TK ORF;

rBAC-TR$_{plp}$-TKsr39, which contains the plp TR sequence and the sr39 derivative of the HSV-1 TK ORF;

rBAC-TR$_{dm}$-TKsr39, which contains the dm20 TR element and the sr39 derivative of the HSV-1 TK ORF;

rBAC-TR$_{plp}$-CAT, which contains the plp TR element and the CAT ORF;

rBAC-TR$_{dm}$-CAT, which contains the dm20 TR sequence and the CAT ORF;

rBAC-TR$_{plp}$-LacZ, which includes the plp TR sequence and the bacterial LacZ ORF; and rBAC-TR$_{dm}$-LacZ, which includes the dm20 TR element and the LacZ ORF.

Example IV

Preparation of Mammalian Cells Stably Expressing the TR-ORF Cassettes

A. Cell Culture

All mammalian cells are maintained at 37° C., 5% CO$_2$ in complete medium which is Dulbecco's Modified Eagle Medium (DMEM) (Invitrogen Life Technologies), supplemented with 10% fetal bovine serum (Hyclone), 3.7 g/L sodium bicarbonate, and 30-50 mg/L gentamicin sulfate (Invitrogen Life Technologies).

B. Transfection and Isolation of Stably Transformed Mammalian Cells

Mammalian transfections are performed using the Calcium Phosphate transfection procedure (using reagents such as the Profection® Mammalian Transfection System, Promega) or the nonlipidic Transfectol Transfection Reagent (Continental Lab Products) as described by the vendor. In this example, HEK293 cells are transfected with various monocistronic pTR-ORF vectors, which include the pTR$_{plp}$-EYFP, pTR$_{dm}$-EYFP, pTR$_{plp}$-fLuc, pTR$_{dm}$-fLuc, pTR$_{plp}$-TK, pTR$_{dm}$-TK, pTR$_{plp}$-CAT, pTR$_{dm}$-CAT, pTR$_{plp}$-LacZ, and pTR$_{dm}$-LacZ vectors. In related efforts, the bicistronic vectors pfLuc-TR$_{plp}$-EYFP, pfLuc-TR$_{dm}$-EYFP, pcuLf-TR$_{plp}$-EYFP and pcuLf-TR$_{dm}$-EYFP are introduced into HEK293 cells.

Prior to transfection, mammalian cells are grown to 50-70% confluence and fed 1-3 hrs prior to addition of the DNA/transfection reagent mixture. A standard transfection assay contains 15 µg of plasmid DNA. Each DNA/transfection reagent mixture is incubated with cells overnight. At this time, the culture medium is replaced, incubated for another 24 hr, and G418 selective DMEM medium (500 µg/mL) applied about 48 hrs post transfection. The selection medium is changed every second day for 2-3 weeks, during which the majority of cells detach and G418 resistant "primary" colonies emerge.

Depending upon the number and density of colonies, surviving cells are grown for 3-5 days in G418-free medium prior to pool isolation or colony subcloning. Once colonies reach an appropriate size, each plate is examined by phase contrast or fluorescence microscopy and colonies marked for subcloning. Flame sterilized cloning rings are placed around the colonies with a light coating of grease and the cells removed by treatment with trypsin-EDTA (Invitrogen). After passage into 24-well trays, subclones are fed 24-48 hrs after plating and grown until 80% confluent. Alternatively, all of the "primary" colonies on a selection plate are collected together in one sample, transferred to 100 mm dish or a T-75 flask, fed 24 hrs after plating, and grown until 80% confluent. This collection of colonies is termed a stable cellular "pool".

In some situations, stable colonies are prepared from pooled samples. For this effort, cells are diluted and replated prior to colony subcloning. Cell pools are diluted at ratios ranging from 1:2500 to 1:5000, passaged onto 100 mm dishes, and allowed to grow into colonies (about 1 week). The resultant colonies are then processed as described for the original selection plates.

Each cellular isolate is assayed using one or more of the cytotoxicity assays described in Examples V-VIII to verify expression and selective translation of the TR-ORF mRNA in stressed or dying cells. Candidate cellular resources, whether subclones or pools, are frozen for storage. For freezing, cells are grown to 90% confluence, treated with trypsin-EDTA (1 min, RT), collected in 2 mL freezing medium (90% fetal bovine serum, 10% DMSO) per 100 mm dish, and transferred to cryotubes (1 ml cells per tube). Cryotubes are placed in a −70/−80 C freezer in a slow freeze container for 16-24 hr, then submerged in liquid nitrogen for long-term storage.

For this example, stable HEK293 cell lines are prepared from colonies isolated after transfection of the pTR$_{plp}$-EYFP, pTR$_{dm}$-EYFP, pTR$_{plp}$-fLuc, and pTR$_{dm}$-fLuc plasmids. Alternatively, HEK293 pools are isolated after transfection with the pTR$_{plp}$-TK, pTR$_{dm}$-TK, pTR$_{plp}$-CAT, pTR$_{dm}$-CAT, pTR$_{plp}$-LacZ, and pTR$_{dm}$-LacZ expression vectors, as well as the bicistronic pfLuc-TR$_{plp}$-EYFP, pfLuc-TR$_{dm}$-EYFP, pcuLf-TR$_{plp}$-EYFP and pcuLf-TR$_{dm}$-EYFP plasmids. Each cellular isolate constitutively expresses a unique monocistronic TR-ORF or bicistronic ORF2-TR-ORF1 mRNA from the CMV IE promoter/enhancer and selectively translated the ORF operably linked to the TR element in stressed or dying cells as determined by one of the cytotoxicity assays described below.

Example V

Procedure for Cytotoxicity Assay Using Western Blot Analysis

A. Western Blot Analysis of Mammalian Cells Expressing a Monocistronic TR Expression Cassette For this example, expression and regulation of the TR$_{plp}$-EYFP, TR$_{dm}$-EYFP, TR$_{plp}$-fLUC, or TR$_{dm}$-fLUC expression cassettes in stably transformed HEK293 cells are validated using Western blot analysis. Cell lines or pools are grown in six-well trays or 60 mm dishes to about 60% confluence and treated with complete medium supplemented with a toxic chemical. For this example, the toxic agents were the proteasomal inhibitor MG132 (50 micromolar) or the Calcium Ionophore A23187 (5-6.7 micromolar), which are shown to produce complete cell death in HEK293 cells within 24 hr as determined by Trypan blue staining. Control samples are treated with fresh medium. Treated and control cells were removed by pipette, collected in media, pelleted for 5 min at 800 rpm (room temperature), and either stored at −70/−80° C. or immediately processed for total proteins.

For protein extraction, cells are resuspended in equal volumes of Suspension Buffer (100 mM NaCl, 10 mM Tris-HCl [pH 7.6], 1 mM EDTA, 1 mg/mL aprotinin, 100 µg/mL PMSF) and 2×SDS Buffer (100 mM Tris-HCl [pH 6.8], 4% SDS, 20% glycerol, 200 mM DTT). Frozen cells are thawed on ice prior to resuspension. The extracts are homogenized by several passages through a syringe fitted with a 26 G needle. Samples are subsequently incubated at RT for 1-2 hr. Samples are transferred to −70/−80° C. for storage or applied to an SDS PAGE gel and examined by Western blot analysis.

To insure equal protein loading levels on Western blots, 10 µL of each protein extract are initially resolved by SDS PAGE, fixed overnight in Preblot gel fixer (25% isopropanol, 10% acetic acid), and stained in 0.05% Coomassie blue (0.05% brilliant blue R, 50% methanol, 10% acetic acid) for 20 min, RT. Gels are destained in 10% acetic acid and dried under vacuum. Using the dried gels, any necessary volume adjustment was made to samples prior to Western blotting.

Western blot analysis is a well established technique in the art and is summarized in the following. Following SDS PAGE gel resolution and protein transfer to a solid membrane support by electrophoresis, the membranes are dried overnight. Subsequent Western analysis requires membrane rehydration, washing with a protein solution (5% powdered milk or 3% BSA) to block stray protein binding sites on the filter, incubation with an antibody that recognizes the TR regulated ORF, and chemiluminescent detection using a labeled secondary antibody. For the EYFP protein, the primary antibody is an anti-GFP antibody (Molecular Probes; 1:500 to 1:1500 dilution). Similarly, fLUC protein is detected using an anti-fLUC antibody (Sigma; 1:1000 dilution). After incubation with a primary antibody and extensive washing (1×PBS-T), proteins binding the primary antibody are detected by incubation with a horseradish peroxidase (HRP) conjugated anti-rabbit or anti-mouse antibody (Amersham; 1:5000 to 1:10000 dilution). Following incubation with the secondary antibody and extensive washing, reactive proteins are detected with the ECL reagent system (Amersham) as described by the vendor.

For this example, the results for HEK293 cell lines expressing the TR$_{plp}$-fLUC, TR$_{dm}$-fLUC or fLUC mRNAs are shown in FIG. 6. Following treatment with toxic levels of the calcium ionophore A23187, highly significant increases in fLuc protein levels are observed in the stressed and dying cells that were not evident in untreated cultures. Individual protein bands are quantitated by densitometry on a Beckman DU7400 spectrophotometer. Cell pools and lines treated with the calcium ionophore A23187 exhibit increases in fLUC protein levels that range from 160-800% of the protein levels detected in untreated TR$_{plp}$-fLUC/TR$_{dm}$-fLUC cells. The average increase in fLuc protein levels observed in stressed and dying HEK293 TR$_{plp}$-fLuc expressing cells is 402.8% (n=5), which is similar to the 524.3% (n=6) increase observed in calcium ionophore treated HEK293 TR$_{dm}$-fLuc cells. Furthermore, cells expressing the TR-fLUC cassette exhibit fLUC protein levels in stressed and dying cells that are as high as 110% of the protein levels produced by cells expressing the cap-dependent CMV-fLuc sequence (FIG. 6).

B. Cytotoxicity Assays Using Cells that Stably Express a Bicistronic TR Cassette In this example, HEK293 cell pools expressing the fLUC-TR$_{plp}$-EYFP, fLUC-TR$_{dm}$-EYFP, pcuLf-TR$_{plp}$-EYFP or pcuLf-TR$_{dm}$-EYFP expression cassettes are treated with the calcium ionophore A23187 and MG132 as above. Briefly, the translation of both reporter proteins is assayed using the Western blot cytotoxicity procedure as described above. Translation of the upstream reporter protein (fLUC) in the sense vectors reflect cap-dependent translation, while the level of the downstream reporter protein (EYFP) correlate with cap-independent (i.e. TR regulated) translation. Although cap-dependent translation may not be measured in the antisense constructs, cap-independent translation can be detected from the ORF operatively linked to the TR element.

The primary and secondary antibodies used in these assays and the assay procedure are as above.

Following the induction of cell stress and death, TR-mediated translation as measured by increases in EYFP protein levels is detected in all cell pools expressing the TR-expression cassette. EYFP protein levels increase to 130-750% of untreated cellular levels. Although the anti-EYFP and anti-fLuc antibodies may not be applied to a single blot, cap-independent translation is more efficient from the monocistronic TR cassette than the bicistronic orientation (FIG. 4). It is also evident that cap-independent TR-mediated translation is not inhibited by insertion of the antisense fLuc ORF upstream of the TR expression cassette.

Example VI

Procedure for Cytotoxicity Assay Using Fluorescent Microscopy

Fluorescence of single cells, tissues or cell suspensions can be detected and quantitated by several means such as visual inspection under a microscope, automated or semiautomated fluorescence imaging, flow cytometry, fluorescence spectroscopy in a fluorometer or in a microplate reader, using an appropriate filter set. For this example, visual inspection under a microscope (Nikon TE2000-S) was used to validate TR translational regulation in stressed and dying HEK293 cells expressing the $TR_{plp}$-EYFP, $TR_{dm}$-EYFP, $TR_{plp}$-fLUC and $TR_{dm}$-fLUC mRNAs.

A. Direct Visualization of TR-Mediated EYFP Translation During a Cytotoxic Event In this study, HEK293 cells transformed with the CMV-EYFP, $TR_{plp}$-EYFP or $TR_{dm}$-EYFP expression cassettes are directly visualized following translation of the spontaneously fluorescent EYFP protein. One day prior to toxin addition, 200,000 cells (HEK293, HEK293 CMV-EYFP, HEK293 $TR_{plp}$-EYFP or HEK293 $TR_{dm}$-EYFP) are plated into a six-well tray containing a flame sterilized glass slide. Cells are cultured for 24 hr in complete DMEM medium. Fresh medium supplemented with 5 micromolar calcium ionophore A23187 is applied and slides were collected at 0 hr, 2 hr, 4 hr, 6 hr, 9 hr, 10 hr, 11 hr and 25 hr. Slides were fixed for 10 min in 4% paraformaldehyde, washed extensively with 1×PBS and mounted for fluorescence microscopy.

Fluorescent cell counts are performed on the 6 hr and 10 hr timepoints using an EYFP-selective filter set (Nikon) and are shown in FIG. 7. In untreated cell cultures, the frequency of EYFP-positive cells range from 1.5-2.5%, which is consistent with the frequency of nonviable cells in these cultures, as determined by Trypan blue staining. Following toxin treatment, EYFP translation from the TR-EYFP cassette, defined as the number of fluorescent cells in at least 5 random sections containing no fewer than 500 cells total, increased as a function of time. In contrast, no significant change in the number of fluorescent cells is detected in the HEK293 or HEK CMV-EYFP cells. The frequency of fluorescent cells in the $TR_{plp}$-EYFP expressing cells rises by 1000-2300% of untreated control cultures. Similar increases are observed in $TR_{dm}$-EYFP expressing cells with cell numbers rising 600-1465% of control cultures (FIG. 7).

B. Direct Visualization of TR-Mediated fLUC Translation During a Cytotoxic Event To examine TR-mediated translation from the TR-fLUC cassettes, the translated fLUC protein requires immunolabeling with fluorescent antibodies. In this study, HEK293 cells transformed with the CMV-fLUC, $TR_{plp}$-fLUC or $TR_{dm}$-fLUC expression cassettes are visualized following immuno-detection of the fLUC protein using a primary anti-fLUC antibody (Sigma) and a species-specific rhodamine-labeled secondary antibody (Kirkegaard and Perry Laboratories, Inc.). DAPI labeling of nuclear DNA is a well known procedure in the art and was used to label nuclei.

Forty hours prior to toxin exposure, 300,000 cells (HEK293, HEK293 CMV-fLUC, HEK293 $TR_{plp}$-fLUC subclone #3, HEK293 $TR_{plp}$-fLUC subclone #17, HEK293 $TR_{dm}$-fLUC subclone #12, or HEK293 $TR_{dm}$-fLUC subclone #45) were plated on flame sterilized glass coverslips in a 12-well tray. Cells are cultured in complete DMEM medium. Fresh medium supplemented with 6.7 micromolar calcium ionophore A23187 is applied and slides collected at 12 hr. Coverslips are fixed in 4% paraformaldehyde (10 min, RT), washed extensively with 1×PBS, permeabilized in 100% methanol (2 min, RT), washed with 1×PBS, blocked in 3% BSA (5 min, RT) and incubated with a primary anti-fLUC antibody (Sigma; 1:500 dilution) for 1 hr at RT. Following the primary antibody staining, the coverslips are washed extensively with 1×PBS and incubated with a rhodamine-labeled anti-rabbit secondary antibody (Kirkegaard and Perry Laboratories; 1:100 to 1:200 dilution) for 1 hr at RT. After this, the coverslips are washed in 1×PBS, labeled with DAPI (30 sec, RT), washed in 1×PBS, and mounted for fluorescence microscopy.

Fluorescent cell counts are performed using rhodamine-selective and DAPI filter sets (Nikon) and are shown in FIG. 8. In untreated cell cultures, the frequency of fLUC-positive cells ranged from 2.4-7.2%, which is 1-3 times higher than the normal frequency of nonviable cells, as determined by Trypan blue staining. Subsequent visual inspection of DAPI stained nuclei establishes that the anti-fLUC antibody selectively cross-reacts with telophase cells, which results in elevated estimates of cell stress in untreated cultures. Following toxin treatment, the frequency of fLUC positive cells in the HEK293 $TR_{plp}$-fLUC subclone #3 and #17 cell lines increased by 1150% and 2245% compared to the number of positive cells in untreated samples, respectively. Similarly, the number of fLUC positive cells in the HEK293 $TR_{dm}$-fLUC subclone #12 and #45 cell lines increased by 3640% and 1440%, respectively.

Example VII

Procedure for Cytotoxicity Assay Using a Microplate Reader

Microplate readers are designed to scan, analyze and obtain numerical results using absorbance, fluorescence and luminescence on high density sample arrays. In this example, a microplate reader was used to measure fluorescent and luminescent marker proteins translated from the TR-ORF cassette.

A. Assay Procedures for the Microplate Reader

For this example, HEK293 cells expressing the $TR_{plp}$-EYFP, $TR_{dm}$-EYFP, $TR_{plp}$ fLUC and $TR_{dm}$-fLUC expression cassettes are evaluated using a microplate reader. To quantitate the TR translational response, 24,000 cells are plated in a 96-well microtiter plates and allowed to grow for about 40 hr to achieve the proper cell density prior to incubation with a toxic agent. Each well is cultured with complete DMEM medium containing either no toxin or a defined concentration of toxin and incubated at 37 C for specific time periods. At that time, fluorescence or chemiluminescence on a FLUOstar Optima (BMG Labtech) microplate reader is used measure TR-ORF response.

Direct detection of the spontaneously fluorescent EYFP protein fluorophore is achieved by excitation of samples in black optical bottom 96-well trays with a fluorescein filter (545 nm) or a YFP filter (YFPex) and emission measured at 590 nm or 544 nm using gains of 1000-2000. To reduce the background fluorescence associated with media components, the trays are centrifuged at 1200 rpm, RT for 3 min to collect any floating cells, and the media replaced with 200 microliters of 1×PBS prior to detection. For the fLUC protein, protein activity is quantified by luminescence produced during live cell or lysed cell luciferase assays. For a live cell assay, cells are cultured as above, but in white optical bottom 96-well trays. After toxin incubation, the 96-well plates are centrifuged at 1200 rpm for 3 min to pellet detached cells. Luminescence is developed by injection of 20 microliters of D-luciferin solution dissolved in sodium citrate/DMSO assay buffer (50% 100 mM sodium citrate, pH5.2, 50% DMSO, 6.7 mM ATP and 3.35 mM D-luciferin) and a 45 sec incubation to allow for cell penetration. Luminescence was detected using lens filter at gains of 2000-3000.

For a lysed cell assay, cells are cultured as above, but in regular flat bottom 96-well trays. After toxin incubation, the 96-well plates are centrifuged as above. The media is removed, replaced with 50 microliters of Cell Lysis Buffer (25 mM Tris-phosphate (pH7.8), 10% glycerol, 1% TritonX-100, 1 mg/ml BSA, 2 mM EGTA and 2 mM DTT) and incubated for 10 min at RT. Cell lysis is verified using a phase contrast microscope, and the lysates transferred to a white bottom 96-well tray. Luminescence is developed by injection of 5 microliters of D-luciferin solution dissolved in Reaction Buffer (25 mM Glycylglycine (pH 7.8), 15 mM MgSO4, 4 mM EDTA, 15 mM Potassium phosphate, 1 mM DTT, 1 mM Coenzyme A, 6.7 mM ATP and 3.35 mM D-luciferin). After 4 sec with shaking, luminescence values were measured using the lens filter at gains of 2000-3000.

B. Measuring a Cytotoxic Event at Fixed Time and Toxin Concentration

Assays based upon fixed time and concentration of a cytotoxic agent are used to identify cellular colonies/pools that exhibit TR-mediated translation. In this example, HEK293 colonies transformed with the CMV-EYFP, $TR_{plp}$-EYFP, $TR_{dm}$-EYFP, CMV-fLUC, $TR_{plp}$-fLUC or $TR_{dm}$-fLUC expression cassettes are screened for TR-specific translational responses following incubation for 12 hr with DMEM medium supplemented with 6.7 micromolar calcium ionophore A23187 (a toxic concentration defined by Trypan blue staining). Colonies are initially propagated in 60-100 mm dishes until 70-80% confluent, transferred to 96-well trays and assayed using cytotoxic medium as described above.

Characteristic results for an independent set of HEK293 $TR_{plp}$-EYFP colonies (FIG. 9), as well as select HEK293 $TR_{plp}$-fLUC and $TR_{dm}$-fLUC colonies (FIG. 9, live cell assay) are shown. As examples of this screening assay, HEK293 $TR_{plp}$-EYFP subclone #41 and HEK293 $TR_{plp}$-fLUC subclone #3 displayed significant TR responses and are selected for subsequent Western blot and microscopy validation.

C. Measuring a Cytotoxic Event as a Function of Toxin Concentration (Dose Response)

Dose response assays are necessary to define toxic concentrations of candidate cytotoxic agents. To establish a TR-mediated cellular response and identify a TR effective dose, HEK293 cells transformed with the $TR_{plp}$-fLUC (subclone #3) and $TR_{dm}$-fLUC (subclone #45) expression cassettes are subjected to a range of subtoxic to toxic concentrations of the calcium ionophore A23187 (0, 1 nM, 10 nM, 100 nM, 1 µM, 2 µM, 4 µM, 6 µM, 8 µM, 10 µM) for 12 hr and analyzed as described above using a lysed cell luciferase assay (FIG. 10).

At the 12 hr time point, using the raw luciferase numbers (FIG. 10, panels A & B), TR-mediated translation is initially detected from each cassette at 1 µM with a peak in fLUC values at 6 µM. Lower subtoxic doses produce no apparent TR-specific translational activity and the 8-10 µM toxin concentrations exhibit a decline in fLuc activity. However, correlating cap-dependent to cap-independent luciferase values produc different results. Adjusting the mean of each luciferase value to the mean of the 0 hr timepoint (expressed as 100%) produces a dose response curve similar to the raw data results (FIG. 10, panel C). In contrast, adjusting the cap-independent fLuc values generated by the TR expression cassette for the significant decline in cap-dependent ribosomal activity exhibited by the HEK293 CMV-fLUC control cells results in significantly higher apparent translation rates and a less significant decline in cap-independent translation even at the highest tested toxin dose.

D. Measuring a Cytotoxic Event as a Function of Time (Temporal Response)

Temporal response assays are used to define the timing of TR-regulated translation during incubation in toxic levels of a cytotoxic agent. HEK293 $TR_{plp}$-fLUC subclone #3 and HEK293 $TR_{dm}$-fLUC subclone #45 are cultured in 6.7 micromolar calcium ionophore A23187 for various times (0 hr, 1.5 hr, 3 hr, 4.5 hr, 6 hr, 7.5 hr, 9 hr, 10.5 hr, 12 hr and 13.5 hr) and analyzed as described above using a lysed cell luciferase assay (FIG. 11).

By 1.5 hr post-incubation, using the raw luciferase numbers, significant TR-specific translation can be detected in each TR transformed cell line (FIG. 11, panels A & B). After 1.5 hr, translational activity increases linearly up to 9 hr post-incubation, where translation exhibits an apparent plateau or slightly lowered activity. However, as before, correlating cap-dependent to cap-independent translation produces different graphs. Adjusting the mean of each luciferase value to the mean of the 0 hr timepoint (expressed as 100%) produdes a dose response curve similar to the raw data results (FIG. 11, panel C). In contrast, adjusting the cap-independent fLuc values generated by the TR expression cassette for the significant decrease in cap-dependent translation observed in HEK293 CMV-fLUC cells results in significantly higher apparent translational activity and a linear increase in translational activity to 12 hr before an apparent translational decline.

Example VIII

Transduction of the TR Expression Cassette into Mammalian Cells Using Recombinant Viruses and Procedures for Assaying TR-Mediated Translation During a Cytotoxic Event A. Method for Transducing Mammalian Cells with rAAV-TR-ORF Virions This example is to show delivery of the $TR_{plp}$-EYFP and $TR_{dm}$-EYFP cassettes to HEK293 and HT1080 cells using rAAV transduction. HEK293 or HT1080 cells are plated on flame sterilized glass slides and grown until 60-70% confluent (1-2 days), washed with L-DMEM (DMEM containing 2% fetal bovine serum), and infected with rAAV for 2 hr. The medium is replaced with DMEM, 10% FBS and the cells are incubated for 24 hours. Infected cells are treated with DMEM, 10% FBS supplemented with toxic levels of MG132 (25 µM) for 24 hr prior to direct microscopic or Western analysis as described above. Cells transduced with rAAV virions exhibit selective translation of the fluorescent EYFP protein compared to uninfected control cells.

B. Assaying a Cytotoxic Event Using rAAV Gene Delivery

HT1080 cells are plated in 6-well trays and allowed to grow until 70-80% confluent. These cells are transduced with rAAV-TR$_{dm}$-EYFP virions (multiplicity of infection of 1-10 pfu/cell) for 24 hr and then treated with medium containing compounds known to induce apoptosis/cell death. For this example, DMEM containing 50 µM MG132, 2 µM thapsigargin, 1 µg/ml actinomycin D, 20 µg/ml cycloheximide, 1 mM dibutrylcyclic-adenosine monophosphate (dbcAMP), 200 µg/ml G418, 5 µM calcium ionophore A23187, 10 µg/ml mitomycin D, 5% methanol or 10% ethanol are separately or in combination added to transduced HT1080 cells for 24 hr. At this time, untreated and treated cells are processed and examined by Western blot analysis, direct microscopic analysis or plate reader analysis as described above.

It is expected that the TR$_{dm}$-EYFP cassette will be translationally active in transduced HT1080 cells cultured in a cytotoxic medium.

C. Transduction of Mammalian Cells with the TR-ORF Cassette Using rBAC Virions

This example is to show delivery of the TR$_{plp}$-EYFP and TR$_{dm}$-EYFP cassettes to HEK293 cells using rBAC transduction. HEK293 cells are plated on flame sterilized glass slides and grown until 60-70% confluent (1-2 days), washed with serum-free DMEM, and infected with rBAC for 1-2 hr. The medium is replaced with DMEM, 10% FBS and the cells incubated for 24 hours. Infected cells were treated with DMEM, 10% FBS supplemented with 5 µM calcium ionophore A23187 for 24 hr prior to direct microscopic examination. Cells transduced with rBAC virions exhibit selective translation of the fluorescent EYFP protein compared to uninfected control cells.

D. Assaying a Cytotoxic Event Using a rBAC Gene Delivery System

HT1080 cells are plated in 6-well trays and allowed to grow until 70-80% confluent. Two sets of HT1080 cells are transduced with rBAC-TR$_{dm}$-EYFP virions (multiplicity of infection of 10 pfu/cell and 25 pfu/cell) for 24 hr and then treated with medium containing 5 µM calcium ionophore A23187 for 13.5 hr and 23 hr. At this time, untreated and treated cells are processed and examined by fluorescence microscopic analysis as described above.

As shown in FIG. 12, the TR$_{dm}$-EYFP cassette is translationally active in transduced HT1080 cells cultured in cytotoxic medium. Significant increases in EYFP positive cells are observed at 13.5 hr (3344% at 10 pfu/cell and 4925% at 25 pfu/cell) and 23 hr (725% at 10 pfu/cell and 875% at 25 pfu/cell) compared to infected (10 pfu/ml) but untreated cell samples. Total cell counts show that increased cell detachment at 23 hr produces the apparent decrease in the total number of positive cells, as the number of attached cells at 23 hr had decreased by more than 50%.

Example IX

Procedure for Inducing a Cytotoxic Event Using a Pro-Drug ORF Expressed from the TR Expression Cassette Due to normal cytotoxic events (i.e. cell contact inhibition, anoikis, etc), mammalian cell cultures generally contain 1-10% nonviable cells. If these cells transcribe a pro-drug ORF operatively linked to the TR cassette, the stressed or dying cells should selectively translate the pro-drug ORF and sensitize these stressed cells to pro-drugs that do not normally affect the parental cell type.

A. Inducing a Cytotoxic Event by Varying Toxin Concentration and Variable Time

In this example, HEK293, HEK CMV-EYFP, and HEK TR$_{plp}$-TKsr39 cells are treated with various amounts of the pro-drug ganciclovir and tested for cell death after 4 days incubation using the Trypan blue staining assay. Cells are plated into 6-well trays, grown to 70-80% confluence, and treated with DMEM, 10% FBS supplemented with ganciclovir (0, 10 nM, 100 nM, 1 µM, 5 µM or 10 µM) for 4 days. Viable cell counts are performed at 3 days and 4 days post-incubation (FIG. 13).

The HEK293 or HEK CMV-EYFP cells do not exhibit any significant increase in cell death at any concentration of ganciclovir after 3 or 4 days of culture. In these cultures, 98-100% of the cells remain Trypan blue viable during the entire treatment period. In contrast, the HEK293 TR$_{plp}$-TKsr39 cells exhibit some microscopic cell death within 3 days as exemplified by detached cells with deformed cellular morphology, condensed nuclei and Trypan blue reactivity. At this time, cell viability falls from 98.5% in untreated cultures to a low of 86% cell viability in 10 µM ganciclovir medium. After 3 days, the 10 nM culture does not exhibit any decrease in cell viability compared to untreated cells, although a slight decrease was detected in the 100 nM sample.

After an additional 24 hr, microscopic analysis establishes that a significant fraction of HEK293 TR$_{plp}$-TKsr39 cell cultures treated with ganciclovir doses of greater than 10 nM are detached and apparently dead (FIG. 13). This is confirmed by the Trypan blue cell viability assay which detects a decline in cell viability at all ganciclovir doses that ranged from 99.7% cell viability in 10 nM cultures to 33.7% viability in 10 µM ganciclovir medium. This example establishes that translation from the TR cassette in stressed or dying cells can be used to selectively synthesize a pro-drug protein which can enhance cell death following pro-drug application. The use of the TKsr39 protein provides an example of bystander killing which is dependent upon selective translation for initiation and underscores the use of selective translation in supplemental gene therapy.

Having described the technology in detail, it will be apparent that modifications and variations are possible without departing the scope of the technology defined in the appended claims. Furthermore, it should be appreciated that all examples in the present disclosure, while illustrating the technology, are provided as non-limiting examples and are, therefore, not to be taken as limiting the various aspects of the technology so illustrated.

What is claimed is:

1. A nucleic acid expression cassette expressible in mammalian cells, wherein the expression cassette comprises the following elements in a 5' to 3' direction:

at least one transcriptional effector sequence, a translational regulatory (TR) element encoding an mRNA molecule that is selectively translated in stressed and/or dying cells, wherein the TR element is the sequence of SEQ ID NO: 1 or the sequence of SEQ ID NO: 2, a nucleotide sequence operably linked to the TR element, that is an open reading frame (ORF) sequence and encodes a polypeptide or a fragment thereof and is co-translated with the TR element, and a polyadenylation sequence, wherein selectively translated in stressed and/or dying cells means that the mRNA translation activity is observed in more than 95% of any cell line transformed with the expression cassette at the peak of translation activity following treatment with an acute toxic agent that induces cell stress and/or death, and that translational levels of the ORF of the expression cassette rise to at least 50% of expression levels of the same ORF when transcribed and translated from the same expression cassette lacking an operably linked TR element following treatment with the acute toxic agent.

2. The expression cassette of claim 1, wherein the TR element is the sequence of SEQ ID NO: 2.

3. The expression cassette of claim 1, wherein the transcriptional effector comprises a constitutive, inducible, tissue specific, tumor specific, or response gene promoter.

4. The expression cassette of claim 3, wherein the promoter is a constitutive promoter selected from the group consisting of retroviral Rous sarcoma virus (RSV) long terminal repeat (LTR) promoter, cytomegalovirus immediate early gene (CMV) promoter, simian virus early (SV40) promoter, cytoplasmic beta-actin promoter, adenovirus major late promoter, and phosphoglycerol kinase (PGK) promoter; an inducible promoter selected from the group consisting of human metallothionein II (hMT-IIA) promoter, dexamethasone (Dex)-inducible promoter, mouse mammary tumor virus (MMTV) promoter, ecdysone-responsive insect promoter, tetracycline responsive (Tet-On promoter, Tet-Off) promoter, mifepristone (RU486)-inducible promoter and rapamycin-responsive promoter; a tissue specific promoter selected from the group consisting of transferrin (TF) promoter, tyrosinase (TYR) promoter, albumin (ALB) promoter, muscle creatine kinase (CKM) promoter, mylin basic protein (MBP) promoter, glial fibrillary acidic protein (GFAP) promoter, neuron-specific enolase (NSE) promoter, and synapsin I (SYN1) promoter; a tumor specific promoter for vascular endothelial growth factor (VEGF), VEGF receptor (KDR), alpha-fetoprotein (AFP), carcinoembryonic antigen (CEA), v-erb-b2 erythroblastic leukemia viral oncogene homolog 2 (erbB2), mucin-1 (muc-1/DF3), ALA, bone gamma-carboxyglutamate protein (BGLAP), secretory leukoproteinase inhibitor or antileukoproteinase 1 (SLP1), hypoxia-response element (HRE), hexokinase II (Grp78/BIP, or HK2); or a response gene promoter for early growth response gene (EGR1), tissue-type plasminogen activator (t-PA), multidrug-resistance protein 1 (mdr-1), heat shock 70 kDa (hsp70), v-fos murine osteosarcoma viral oncogene homolog (c-fos), v-jun sarcoma virus 17 oncogene homolog (c-jun), E2F transcription factor 1 (E2F-1), heat shock 70 kDa protein 5 (HSPA5), cyclin A1 (CCNA1) or cell division cycle 25C (cdc25C).

5. The expression cassette of claim 1, wherein the ORF sequence is selected from the group consisting of reporter gene, cytotoxic tumor suppressor, toxin gene, prodrug activating gene and proapoptotic gene.

6. The expression cassette of claim 5, wherein the ORF sequence is a reporter gene.

7. The expression cassette of claim 6, wherein the reporter gene is selected from the group consisting of EGFP, GFP, EYFP, luciferase, LacZ, CAT, TK, and TKsr39.

8. The expression cassette of claim 7, wherein the reporter gene is luciferase.

9. The expression cassette of claim 5, wherein the ORF sequence is a cytotoxic tumor suppressor selected from the group consisting of p53, APC, BRCA-1, BRCA-2, WT-1, retinoblastoma, NF-1, NF-2 and VHL.

10. The expression cassette of claim 9, wherein the cytotoxic tumor suppressor is p53.

11. The expression cassette of claim 5, wherein the ORF sequence is a toxin gene selected from the group consisting of pseudomonas exotoxin, ricin toxin, and diptheria toxin.

12. The expression cassette of claim 11, wherein the toxin gene is diphteria toxin.

13. The expression cassette of claim 5, wherein the ORF sequence is a prodrug activating gene selected from the group consisting of TK and TKsr39.

14. The expression cassette of claim 13, wherein the prodrug activating gene is TKsr39.

15. The expression cassette of claim 5, wherein the ORF sequence is a proapoptotic gene selected from the group consisting of p53, APC, BRCA-1, BRCA-2, WT-1, Rb, NF-1, NF-2, and VHL genes.

16. The expression cassette of claim 15, wherein the proapoptotic gene is p53.

17. The expression cassette of claim 1, wherein the polyadenylation sequence is selected from the group consisting of SV40 early gene, SV40 late gene, HSV-TK, and hGH polyA tails.

18. The expression cassette of claim 1, wherein the nucleotide sequence further comprises a 5' untranslated region, which is located 3' to the transcriptional effector sequence and 5' to the TR element and comprises an mRNA transcription initiation site.

19. The expression cassette of claim 18, wherein the 5' untranslated region comprises an intron sequence which directs mRNA splicing.

20. The expression cassette of claim 1, wherein the nucleotide sequence further comprises one or more of the following:
  a sequence of between about 15-50 nucleotides located 5' to the transcriptional effector sequence, that comprises one or more restriction sites for insertion of the cassette into a plasmid, shuttle vector or viral vector;
  a sequence of between about 15-50 nucleotides located 3' to the TR element and 5' to the ORF sequence, that comprises one or more restriction sites for insertion and operative linkage of the TR element and the ORF sequence;
  a sequence of between about 15-50 nucleotides located 3' to the ORF sequence and 5' to the polyadenylation sequence, that comprises one or more restriction sites for insertion and operative linkage of the ORF sequence and the polyadenylation sequence; or
  a sequence of between about 15-50 nucleotides located 3' to the polyadenylation sequence, that comprises one or more restriction sites for insertion of the cassette into a plasmid, shuttle vector or viral vector, wherein the addition of any of the sequences keeps translation in frame.

21. The expression cassette of claim 1, wherein the expression cassette is contained in a plasmid, shuttle vector, or viral vector.

22. The expression cassette of claim 21, wherein expression cassette is contained in a plasmid selected from the group consisting of pCMVneo, pCMV-MCS, pBluescript II, pET14, and pUC19; a shuttle vector selected from the group consisting of pCMV, pEYFP-N1, pEGFP-N1, and pEGFP-C1; or a viral vector selected from the group consisting of pAAV-MCS, pBac-1, and pBacPAK8/9.

23. The expression cassette of claim 22, wherein the plasmid is pCMVneo.

24. The expression cassette of claim 22, wherein the shuttle vector is pEYFP-N1.

25. The expression cassette of claim 22, wherein the viral vector is pAAV-MCS.

26. A mammalian cell that is transformed with the expression cassette of claim 1.

27. The mammalian cell of claim 26, wherein the mammalian cell is selected from the group consisting of HEK293, HT1080, NTERA-2D, HeLa, Caco2, HepG2, BALBC/3T3, and Cos-7.

28. The mammalian cell of claim 26, wherein the mammalian cell is an embryonic stem cell.

29. The mammalian cell of claim 28, wherein the embryonic stem cell is a murine embryonic stem cell mES-D3 or human embryonic stem cell hES.

30. The mammalian cell of claim 26, wherein the ORF sequence is selected from the group consisting of reporter gene, cytotoxic tumor suppressor, toxin gene, prodrug activating gene and proapoptotic gene.

31. The mammalian cell of claim 30, wherein the ORF sequence is a reporter gene.

32. The mammalian cell of claim 31, wherein the reporter gene is selected from the group consisting of EGFP, GFP, EYFP, luciferase, LacZ, CAT, TK, and TKsr39.

33. The mammalian cell of claim 32, wherein the reporter gene is luciferase.

34. A method for determining toxicity of a substance, wherein the method comprises:
(a) contacting the mammalian cells of claim 31 with the substance, wherein the ORF sequence encodes a reporter polypeptide; and
(b) detecting presence or measuring a level of the reporter polypeptide, wherein the toxicity of the substance correlates to the presence or the increase in the level of the reporter polypeptide as compared to control cells that are not exposed to the substance or are not transformed.

35. The method of claim 34, wherein the protein level of the reporter polypeptide is measured.

36. The method of claim 34, wherein the presence or levels of the mRNA of the reporter polypeptide are measured.

37. The method of claim 34, wherein the step of contacting the mammalian cells is performed ex vivo.

38. The method of claim 34, wherein the reporter polypeptide is luciferase.

39. A method for determining toxicity of a substance to a mammal, wherein the method comprises:
(a) transfecting a mammalian cell or a mammalian cell line with the expression cassette of claim 6, wherein the ORF sequence encodes a reporter polypeptide;
(b) contacting transfected cells from (a) with the substance; and
(c) detecting presence or measuring levels of the reporter polypeptide, wherein the toxicity of the substance correlates to the presence or the increase in the level of the reporter polypeptide as compared to control cells that are not exposed to the substance or are not transformed.

40. The method of claim 39, wherein the protein level of the reporter polypeptide is measured.

41. The method of claim 39, wherein the presence or levels of the mRNA of the reporter polypeptide are measured.

42. The method of claim 39, wherein the reporter polypeptide is luciferase.

43. A kit useful for toxicity assays comprising
(a) the expression cassette of claim 1; and
(b) instructions for use of the kit.

44. A kit useful for toxicity assays comprising
(a) the mammalian cells of claim 26; and
(b) instructions for use of the kit.

45. A transgenic non-human animal comprising the expression cassette of claim 1 stably integrated into the genome of the animal.

46. A method of inducing apoptosis in a target cell comprising:
transforming the cell with the expression cassette of claim 9; and
exposing the transformed cell under toxic conditions.

47. A method of inducing apoptosis in a target cell comprising:
transforming the cell with the expression cassette of claim 11; and
exposing the transformed cell under toxic conditions.

48. A method of inducing apoptosis in a target cell comprising:
transforming the cell with the expression cassette of claim 13; and
exposing the transformed cell under toxic conditions.

49. A method of inducing apoptosis in a target cell comprising:
transforming the cell with the expression cassette of claim 15; and
exposing the transformed cell under toxic conditions.

50. A method for detecting cell stress and/or apoptosis, wherein the method comprises:
(a) obtaining the mammalian cells of claim 31, wherein the ORF sequence encodes a reporter polypeptide, or transfecting a mammalian cell or a mammalian cell line with the expression cassette of claim 6, wherein the ORF sequence encodes a reporter polypeptide; and
(b) detecting presence or measuring a level of the reporter polypeptide, wherein the level of cell stress and/or apoptosis correlates to the presence or the increase in the level of the reporter polypeptide as compared to control cells that are not transfected.

51. The method of claim 50, wherein the method includes prior to step (b) a step of contacting the mammalian cells with a substance capable of inducing cell stress and/or apoptosis.

52. The method of claim 50, wherein the protein level of the reporter polypeptide is measured or the presence or levels of the mRNA of the reporter polypeptide are measured.

53. The method of claim 50, wherein the reporter polypeptide is luciferase.

54. A method for inhibiting apoptosis in a mammalian cell comprising transforming the mammalian cell with the expression cassette of claim 1, wherein the ORF sequence encodes an antiapoptotic protein.

55. The method of claim 54, wherein the antiapoptotic protein is selected from the group consisting of BCL2, BCL2L1, BCL2A1, BAG1, TRAF1, BIRC3, BIRC5, BAK1, and API5.

56. A pharmaceutical composition comprising the expression cassette of claim 1 and a pharmaceutically acceptable carrier.

\* \* \* \* \*

SEQUENCE LISTING

<160> NUMBER OF SEQ ID NOS: 63

<210> SEQ ID NO 1
<211> LENGTH: 726
<212> TYPE: DNA

<213> ORGANISM: Artificial Sequence
<220> FEATURE:
<223> OTHER INFORMATION: Murine derived TRdm

<400> SEQUENCE: 1

```
ttgagtgagt tagagtagtg agctagttgt ctggtagggg cccccttttgc ttccctggtg    60
gccactggat tgtgtttctt tggagtggca ctgttctgtg gatgtggaca tgaagctctc   120
actggtacag aaaagctaat tgagacctat ttctccaaaa actaccagga ctatgagtat   180
ctcattaatg tgattcatgc tttccagtat gtcatctatg gaactgcctc tttcttcttc   240
ctttatgggg ccctcctgct ggctgagggc ttctacacca ccggcgctgt caggcagatc   300
tttggcgact acaagaccac catctgcggc aagggcctga gcgcaacgtt tgtgggcatc   360
acctatgccc tgactgttgt atggctcctg gtgtttgcct gctcggctgt acctgtgtac   420
atttacttca ataccctggac cacctgtcag tctattgcct ccctagcaa gacctctgcc   480
agtataggca gtctctgcgc tgatgccaga ttgtatggtg ttctcccatg gaatgctttc   540
cctggcaagg tttgtggctc caaccttctg tccatctgca aaacagctga gttccaattg   600
accttccacc tgtttattgc tgcgtttgtg ggtgctgcgg ccacactagt ttccctgctc   660
accttcatga ttgctgccac ttacaacttc gccgtcctta aactcatggg ccgaggcacc   720
aagttc                                                              726
```

<210> SEQ ID NO 2
<211> LENGTH: 831
<212> TYPE: DNA
<213> ORGANISM: Artificial Sequence
<220> FEATURE:
<223> OTHER INFORMATION: Murine derived TRplp

<400> SEQUENCE: 2

```
ttgagtgagt tagagtagtg agctagttgt ctggtagggg cccccttttgc ttccctggtg    60
gccactggat tgtgtttctt tggagtggca ctgttctgtg gatgtggaca tgaagctctc   120
actggtacag aaaagctaat tgagacctat ttctccaaaa actaccagga ctatgagtat   180
ctcattaatg tgattcatgc tttccagtat gtcatctatg gaactgcctc tttcttcttc   240
ctttatgggg ccctcctgct ggctgagggc ttctacacca ccggcgctgt caggcagatc   300
tttggcgact acaagaccac catctgcggc aagggcctga gcgcaacggt aacaggggc    360
cagaagggga ggggttccag aggccaacat caagctcatt ctttggagcg ggtgtgtcat   420
tgtttgggaa aatggctagg acatcccgac aagtttgtgg gcatcaccta tgccctgact   480
gttgtatggc tcctggtgtt tgcctgctcg gctgtacctg tgtacattta cttcaatacc   540
tggaccacct gtcagtctat tgccttccct agcaagacct ctgccagtat aggcagtctc   600
tgcgctgatg ccagattgta tggtgttctc ccatggaatg ctttccctgg caaggtttgt   660
ggctccaacc ttctgtccat ctgcaaaaca gctgagttcc aattgacctt ccacctgttt   720
attgctgcgt ttgtgggtgc tgcggccaca ctagtttccc tgctcacctt catgattgct   780
gccacttaca acttcgccgt ccttaaactc atgggccgag gcaccaagtt c            831
```

<210> SEQ ID NO 3
<211> LENGTH: 3223
<212> TYPE: DNA
<213> ORGANISM: Artificial sequence
<220> FEATURE:
<223> OTHER INFORMATION: Monocistronic TRdm luciferase expression
    cassette

<400> SEQUENCE: 3

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta caactccgcc ccattgacg caaatgggcg gtaggcgtgt   540
acggtgggag gtctatataa gcagagctgg tttagtgaac cgtcagatcc gctagcgcta   600
ccggactcag atcctcagag tgccgaattc ttgagtgagt tagagtagtg agctagttgt   660
ctggtagggg ccccctttgc ttccctggtg gccactggat tgtgtttctt tggagtggca   720
ctgttctgtg gatgtggaca tgaagctctc actggtacag aaaagctaat tgagacctat   780
ttctccaaaa actaccagga ctatgagtat ctcattaatg tgattcatgc tttccagtat   840
gtcatctatg gaactgcctc tttcttcttc ctttatgggg ccctcctgct ggctgagggc   900
ttctacacca ccggcgctgt caggcagatc tttggcgact acaagaccac catctgcggc   960
aagggcctga gcgcaacgtt tgtgggcatc acctatgccc tgactgttgt atggctcctg  1020
gtgtttgcct gctcggctgt acctgtgtac atttacttca atacctggac cacctgtcag  1080
tctattgcct tccctagcaa gacctctgcc agtataggca gtctctgcgc tgatgccaga  1140
ttgtatggtg ttctcccatg gaatgctttc cctggcaagg tttgtggctc caaccttctg  1200
tccatctgca aaacagctga gttccaattg accttccacc tgtttattgc tgcgtttgtg  1260
ggtgctgcgg ccacactagt ttccctgctc accttcatga ttgctgccac ttacaacttc  1320
gccgtcctta aactcatggg ccgaggcacc aagttcgaaa gcttcgccac catggaagac  1380
gccaaaaaca taagaaaggg cccggcgcca ttctatccgc tggaagatgg aaccgctgga  1440
gagcaactgc ataaggctat gaagagatac gccctggttc ctggaacaat tgcttttaca  1500
gatgcacata tcgaggtgga catcacttac gctgagtact cgaaatgtc cgttcggttg  1560
gcagaagcta tgaaacgata tgggctgaat acaaatcaca gaatcgtcgt atgcagtgaa  1620
aactctcttc aattctttat gccggtgttg ggcgcgttat ttatcggagt tgcagttgcg  1680
cccgcgaacg acatttataa tgaacgtgaa ttgctcaaca gtatgggcat ttcgcagcct  1740
accgtggtgt tcgtttccaa aaaggggttg caaaaaattt tgaacgtgca aaaaaagctc  1800
ccaatcatcc aaaaaattat tatcatggat tctaaaacgg attaccaggg atttcagtcg  1860
atgtacacgt tcgtcacatc tcatctacct cccggtttta atgaatacga ttttgtgcca  1920
gagtccttcg atagggacaa gacaattgca ctgatcatga actcctctgg atctactggt  1980
ctgcctaaag gtgtcgctct gcctcataga actgcctgcg tgagattctc gcatgccaga  2040
gatcctattt ttggcaatca aatcattccg gatactgcga ttttaagtgt tgttccattc  2100
catcacggtt ttggaatgtt tactacactc ggatatttga tatgtggatt tcgagtcgtc  2160
ttaatgtata gatttgaaga agagctgttt ctgaggagcc ttcaggatta caagattcaa  2220
agtgcgctgc tggtgccaac cctattctcc ttcttcgcca aaagcactct gattgacaaa  2280
tacgatttat ctaatttaca cgaaattgct tctggtggcg ctcccctctc taaggaagtc  2340
```

-continued

```
ggggaagcgg ttgccaagag gttccatctg ccaggtatca ggcaaggata tgggctcact    2400
gagactacat cagctattct gattacaccc gaggggatg ataaaccggg cgcggtcggt    2460
aaagttgttc catttttga agcgaaggtt gtggatctgg ataccgggaa aacgctgggc    2520
gttaatcaaa gaggcgaact gtgtgtgaga ggtcctatga ttatgtccgg ttatgtaaac    2580
aatccggaag cgaccaacgc cttgattgac aaggatggat ggctacattc tggagacata    2640
gcttactggg acgaagacga acacttcttc atcgttgacc gcctgaagtc tctgattaag    2700
tacaaaggct atcaggtggc tcccgctgaa ttggaatcca tcttgctcca cacccccaac    2760
atcttcgacg caggtgtcgc aggtcttccc gacgatgacg ccggtgaact ccccgccgcc    2820
gttgttgttt tggagcacgg aaagacgatg acggaaaag atcgtggatt acgtcgcc     2880 agtcaagtaa caaccgcgaa aaagttgcgc ggaggagttg tgtttgtgga cgaagtaccg    2940
aaaggtctta ccggaaaact cgacgcaaga aaaatcagag agatcctcat aaaggccaag    3000
aagggcggaa agatcgccgt gtaactcgag atctagatca taatcagcca taccacattt    3060
gtagaggttt tacttgcttt aaaaaacctc ccacacctcc ccctgaacct gaaacataaa    3120
atgaatgcaa ttgttgttgt taacttgttt attgcagctt ataatggtta caaataaagc    3180
aatagcatca caaatttcac aaataaagca ttttttcac tgc                    3223
```

<210> SEQ ID NO 4
<211> LENGTH: 3328
<212> TYPE: DNA
<213> ORGANISM: Artificial Sequence
<220> FEATURE:
<223> OTHER INFORMATION: Monocistronic TRplp luciferase expression cassette

<400> SEQUENCE: 4

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggacttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atcctcagag tgccgaattc ttgagtgagt tagagtagtg agctagttgt    660
ctggtagggg ccccctttgc ttccctggtg gccactggat tgtgtttctt tggagtggca    720
ctgttctgtg gatgtggaca tgaagctctc actggtacag aaaagctaat tgagacctat    780
ttctccaaaa actaccagga ctatgagtat ctcattaatg tgattcatgc tttccagtat    840
gtcatctatg gaactgcctc tttcttcttc ctttatgggg ccctcctgct ggctgagggc    900
ttctacacca ccggcgctgt caggcagatc tttggcgact acaagaccac catctgcggc    960
aagggcctga gcgcaacggt aacagggggc cagaagggga ggggttccag aggccaacat    1020
caagctcatt ctttgagcg ggtgtgtcat tgtttggaa atggctagg acatcccgac    1080 aagtttgtgg gcatcaccta tgccctgact gttgtatggc tcctggtgtt tgcctgctcg    1140
```

```
gctgtacctg tgtacattta cttcaatacc tggaccacct gtcagtctat tgccttccct    1200
agcaagacct ctgccagtat aggcagtctc tgcgctgatg ccagattgta tggtgttctc    1260
ccatggaatg ctttccctgg caaggtttgt ggctccaacc ttctgtccat ctgcaaaaca    1320
gctgagttcc aattgacctt ccacctgttt attgctgcgt tgtgggtgc tgcggccaca     1380 ctagttccc tgctcacctt catgattgct gccacttaca acttcgccgt ccttaaactc      1440
atgggccgag gcaccaagtt cgaaagcttc gccaccatgg aagacgccaa aaacataaag    1500
aaaggcccgg cgccattcta tccgctggaa gatggaaccg ctggagagca actgcataag    1560
gctatgaaga gatacgccct ggttcctgga acaattgctt ttacagatgc acatatcgag    1620
gtggacatca cttacgctga gtacttcgaa atgtccgttc ggttggcaga agctatgaaa    1680
cgatatgggc tgaatacaaa tcacagaatc gtcgtatgca gtgaaaactc tcttcaattc    1740
tttatgccgg tgttgggcgc gttatttatc ggagttgcag ttgcgcccgc gaacgacatt    1800
tataatgaac gtgaattgct caacagtatg ggcatttcgc agcctaccgt ggtgttcgtt    1860
tccaaaaagg ggttgcaaaa aattttgaac gtgcaaaaaa agctcccaat catccaaaaa    1920
attattatca tggattctaa aacggattac cagggatttc agtcgatgta cacgttcgtc    1980
acatctcatc tacctcccgg ttttaatgaa tacgattttg tgccagagtc cttcgatagg    2040
gacaagacaa ttgcactgat catgaactcc tctggatcta ctggtctgcc taaaggtgtc    2100
gctctgcctc atagaactgc ctgcgtgaga ttctcgcatg ccagagatcc tatttttggc    2160
aatcaaatca ttccggatac tgcgatttta agtgttgttc cattccatca cggttttgga    2220
atgtttacta cactcggata tttgatatgt ggatttcgag tcgtcttaat gtatagattt    2280
gaagaagagc tgtttctgag gagccttcag gattacaaga ttcaaagtgc gctgctggtg    2340
ccaaccctat tctccttctt cgccaaaagc actctgattg acaaatacga tttatctaat    2400
ttacacgaaa ttgcttctgg tggcgctccc ctctctaagg aagtcgggga agcggttgcc    2460
aagaggttcc atctgccagg tatcaggcaa ggatatgggc tcactgagac tacatcagct    2520
attctgatta cacccgaggg ggatgataaa ccgggcgcgg tcggtaaagt tgttccattt    2580
tttgaagcga aggttgtgga tctggatacc gggaaaacgc tgggcgttaa tcaaagaggc    2640
gaactgtgtg tgagaggtcc tatgattatg tccggttatg taaacaatcc ggaagcgacc    2700
aacgccttga ttgacaagga tggatggcta cattctggag acatagctta ctgggacgaa    2760
gacgaacact tcttcatcgt tgaccgcctg aagtctctga ttaagtacaa aggctatcag    2820
gtggctcccg ctgaattgga atccatcttg ctccaacacc ccaacatctt cgacgcaggt    2880
gtcgcaggtc ttcccgacga tgacgccggt gaacttcccg ccgccgttgt tgttttggag    2940
cacggaaaga cgatgacgga aaagagatcg tggattacg tcgccagtca agtaacaacc     3000 gcgaaaagt tgcgcggagg agttgtgttt gtggacgaag taccgaaagg tcttaccgga      3060
aaactcgacg caagaaaaat cagagagatc ctcataaagg ccaagaaggg cggaaagatc    3120
gccgtgtaac tcgagatcta gatcataatc agccatacca catttgtaga ggttttactt    3180
gctttaaaaa acctcccaca cctccccctg aacctgaaac ataaaatgaa tgcaattgtt    3240
gttgttaact tgtttattgc agcttataat ggttacaaat aaagcaatag catcacaaat    3300
ttcacaaata aagcattttt ttcactgc                                       3328
```

<210> SEQ ID NO 5
<211> LENGTH: 3964
<212> TYPE: DNA

<213> ORGANISM: Artificial sequence
<220> FEATURE:
<223> OTHER INFORMATION: Bicistronic luciferase TRdm EYFP expression cassette

<400> SEQUENCE: 5

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacg caaatgggcg gtaggcgtgt     540
acggtgggag gtctatataa gcagagctgg tttagtgaac cgtcagatcc gctagcgcta     600
ccggactcag atcctcagag tgccgaattc atggaagacg ccaaaaacat aaagaaaggc     660
ccggcgccat tctatccgct ggaagatgga accgctggag agcaactgca taaggctatg     720
aagagatacg ccctggttcc tggaacaatt gcttttacag atgcacatat cgaggtggac     780
atcacttacg ctgagtactt cgaaatgtcc gttcggttgg cagaagctat gaaacgatat     840
gggctgaata caaatcacag aatcgtcgta tgcagtgaaa actctcttca attctttatg     900
ccggtgttgg gcgcgttatt tatcggagtt gcagttgcgc ccgcgaacga catttataat     960
gaacgtgaat tgctcaacag tatgggcatt tcgcagccta ccgtggtgtt cgtttccaaa    1020
aagggggttgc aaaaaatttt gaacgtgcaa aaaaagctcc aatcatcca aaaaattatt    1080
atcatggatt ctaaaacgga ttaccaggga tttcagtcga tgtacacgtt cgtcacatct    1140
catctacctc ccggttttaa tgaatacgat tttgtgccag agtccttcga tagggacaag    1200
acaattgcac tgatcatgaa ctcctctgga tctactggtc tgcctaaagg tgtcgctctg    1260
cctcatagaa ctgcctgcgt gagattctcg catgccagag atcctatttt tggcaatcaa    1320
atcattccgg atactgcgat tttaagtgtt gttccattcc atcacggttt tggaatgttt    1380
actacactcg gatatttgat atgtggattt cgagtcgtct taatgtatag atttgaagaa    1440
gagctgtttc tgaggagcct tcaggattac aagattcaaa gtgcgctgct ggtgccaacc    1500
ctattctcct tcttcgccaa agcactctg attgacaaat acgatttatc taatttacac    1560
gaaattgctt ctggtggcgc tcccctctct aaggaagtcg ggaagcggt tgccaagagg    1620
ttccatctgc caggtatcag gcaaggatat gggctcactg agactacatc agctattctg    1680
attacacccg agggggatga taaaccgggc gcggtcggta agttgttcc attttttgaa    1740
gcgaaggttg tggatctgga taccgggaaa acgctgggcg ttaatcaaag aggcgaactg    1800
tgtgtgagag gtcctatgat tatgtccggt tatgtaaaca atccggaagc gaccaacgcc    1860
ttgattgaca aggatggatg gctacattct ggagacatag cttactggga cgaagacgaa    1920
cacttcttca tcgttgaccg cctgaagtct ctgattaagt acaaaggcta tcaggtggct    1980
cccgctgaat ggaatccat cttgctccaa caccccaaca tcttcgacgc aggtgtcgca    2040
ggtcttcccg acgatgacgc cggtgaactt cccgccgccg ttgttgtttt ggagcacgga    2100
aagacgatga cggaaaaaga gatcgtggat tacgtcgcca gtcaagtaac aaccgcgaaa    2160
```

```
aagttgcgcg gaggagttgt gtttgtggac gaagtaccga aaggtcttac cggaaaactc    2220
gacgcaagaa aaatcagaga gatcctcata aaggccaaga agggcggaaa gatcgccgtg    2280
taagaattct tgagtgagtt agagtagtga gctagttgtc tggtaggggc cccctttgct    2340
tccctggtgg ccactggatt gtgtttcttt ggagtggcac tgttctgtgg atgtggacat    2400
gaagctctca ctggtacaga aaagctaatt gagacctatt tctccaaaaa ctaccaggac    2460
tatgagtatc tcattaatgt gattcatgct ttccagtatg tcatctatgg aactgcctct    2520
ttcttcttcc tttatggggc cctcctgctg gctgagggct tctacaccac cggcgctgtc    2580
aggcagatct ttggcgacta caagaccacc atctgcggca agggcctgag cgcaacgttt    2640
gtgggcatca cctatgccct gactgttgta tggctcctgg tgtttgcctg ctcggctgta    2700
cctgtgtaca tttacttcaa tacctggacc acctgtcagt ctattgcctt ccctagcaag    2760
acctctgcca gtataggcag tctctgcgct gatgccagat tgtatggtgt tctcccatgg    2820
aatgctttcc ctggcaaggt tgtggctcaa accttctgt ccatctgcaa aacagctgag    2880
ttccaattga ccttccacct gtttattgct gcgtttgtgg gtgctgcggc cacactagtt    2940
tccctgctca ccttcatgat tgctgccact tacaacttcg ccgtccttaa actcatgggc    3000
cgaggcacca agttcccgcg ggcccgggat ccaccggtcg ccaccatggt gagcaagggc    3060
gaggagctgt tcaccggggt ggtgcccatc ctggtcgagc tggacggcga cgtaaacggc    3120
cacaagttca gcgtgtccgg cgagggcgag ggcgatgcca cctacggcaa gctgaccctg    3180
aagttcatct gcaccaccgg caagctgccc gtgccctggc ccaccctcgt gaccaccttc    3240
ggctacggcc tgcagtgctt cgcccgctac cccacatgaag cagcacgact tcttcaagtc    3300
cgccatgccc gaaggctacg tccaggagcg caccatcttc ttcaaggacg acggcaacta    3360
caagacccgc gccgaggtga agttcgaggg cgacaccctg gtgaaccgca tcgagctgaa    3420
gggcatcgac ttcaaggagg acggcaacat cctggggcac aagctggagt acaactacaa    3480
cagccacaac gtctatatca tggccgacaa gcagaagaac ggcatcaagg tgaacttcaa    3540
gatccgccac aacatcgagg acggcagcgt gcagctcgcc gaccactacc agcagaacac    3600
ccccatcggc gacggccccg tgctgctgcc cgacaaccac tacctgagct accagtccgc    3660
cctgagcaaa gaccccaacg agaagcgcga tcacatggtc ctgctggagt tcgtgaccgc    3720
cgccgggatc actctcggca tggacgagct gtacaagtaa agcggccgcg actctagatc    3780
ataatcagcc ataccacatt tgtagaggtt ttacttgctt taaaaaacct cccacacctc    3840
cccctgaacc tgaaacataa aatgaatgca attgttgttg ttaacttgtt tattgcagct    3900
tataatggtt acaaataaag caatagcatc acaaatttca caaataaagc atttttttca    3960
ctgc                                                                  3964
```

<210> SEQ ID NO 6
<211> LENGTH: 4069
<212> TYPE: DNA
<213> ORGANISM: Artificial sequence
<220> FEATURE:
<223> OTHER INFORMATION: Bicistronic luciferase TRplp EYFP expression
      cassette

<400> SEQUENCE: 6

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
```

```
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atcctcagag tgccgaattc atggaagacg ccaaaaacat aaagaaaggc    660
ccggcgccat tctatccgct ggaagatgga accgctggag agcaactgca taaggctatg    720
aagagatacg ccctggttcc tggaacaatt gcttttacag atgcacatat cgaggtggac    780
atcacttacg ctgagtactt cgaaatgtcc gttcggttgg cagaagctat gaaacgatat    840
gggctgaata caaatcacag aatcgtcgta tgcagtgaaa actctcttca attctttatg    900
ccggtgttgg gcgcgttatt tatcgagtt gcagttgcgc ccgcgaacga catttataat    960
gaacgtgaat tgctcaacag tatgggcatt tcgcagccta ccgtggtgtt cgtttccaaa   1020
aagggggttgc aaaaaatttt gaacgtgcaa aaaagctcc caatcatcca aaaaattatt   1080
atcatggatt ctaaaacgga ttaccaggga tttcagtcga tgtacacgtt cgtcacatct   1140
catctacctc ccgttttaa tgaatacgat tttgtgccag agtccttcga tagggacaag   1200
acaattgcac tgatcatgaa ctcctctgga tctactggtc tgcctaaagg tgtcgctctg   1260
cctcatagaa ctgcctgcgt gagattctcg catgccagag atcctatttt tggcaatcaa   1320
atcattccgg atactgcgat tttaagtgtt gttccattcc atcacggttt tggaatgttt   1380
actacactcg gatatttgat atgtggattt cgagtcgtct taatgtatag atttgaagaa   1440
gagctgtttc tgaggagcct tcaggattac aagattcaaa gtgcgctgct ggtgccaacc   1500
ctattctcct cttcgccaa aagcactctg attgacaaat acgatttatc taatttacac   1560
gaaattgctt ctggtggcgc tcccctctct aaggaagtcg ggaagcggt tgccaagagg   1620
ttccatctgc caggtatcag gcaaggatat gggctcactg agactacatc agctattctg   1680
attacacccg aggggatga taaaccgggc gcggtcggta agttgttcc attttttgaa   1740
gcgaaggttg tggatctgga taccgggaaa acgctgggcg ttaatcaaag aggcgaactg   1800
tgtgtgagag gtcctatgat tatgtccggt tatgtaaaca atccggaagc gaccaacgcc   1860
ttgattgaca aggatggatg gctacattct ggagacatag cttactggga cgaagacgaa   1920
cacttcttca tcgttgaccg cctgaagtct ctgattaagt acaaaggcta tcaggtggct   1980
cccgctgaat ggaatccat cttgctccaa caccccaaca tcttcgacgc aggtgtcgca   2040
ggtcttcccg acgatgacgc cggtgaactt cccgccgccg ttgttgtttt ggagcacgga   2100
aagacgatga cggaaaaaga gatcgtggat tacgtcgcca gtcaagtaac aaccgcgaaa   2160
aagttgcgcg gaggagttgt gtttgtggac gaagtaccga aaggtcttac cggaaaactc   2220
gacgcaagaa aaatcagaga gatcctcata aggccaaga agggcggaaa gatcgccgtg   2280
taagaattct tgagtgagtt agagtagtga gctagttgtc tggtagggc cccctttgct   2340
tccctggtgg ccactggatt gtgtttcttt ggagtggcac tgttctgtgg atgtggacat   2400
gaagctctca ctggtacaga aaagctaatt gagacctatt ctccaaaaa ctaccaggac   2460
tatgagtatc tcattaatgt gattcatgct ttccagtatg tcatctatgg aactgcctct   2520
ttcttcttcc tttatggggc cctcctgctg gctgagggct tctacaccac cggcgctgtc   2580
```

```
aggcagatct ttggcgacta caagaccacc atctgcggca agggcctgag cgcaacggta    2640 acaggggcc agaaggggag gggttccaga ggccaacatc aagctcattc tttggagcgg    2700
gtgtgtcatt gtttgggaaa atggctagga catcccgaca agtttgtggg catcacctat    2760
gccctgactg ttgtatggct cctggtgttt gcctgctcgg ctgtacctgt gtacatttac    2820
ttcaatacct ggaccacctg tcagtctatt gccttcccta gcaagacctc tgccagtata    2880
ggcagtctct gcgctgatgc cagattgtat ggtgttctcc catggaatgc tttccctggc    2940
aaggtttgtg gctccaacct tctgtccatc tgcaaaacag ctgagttcca attgaccttc    3000
cacctgttta ttgctgcgtt tgtgggtgct gcggccacac tagtttccct gctcaccttc    3060
atgattgctg ccacttacaa cttcgccgtc cttaaactca tgggccgagg caccaagttc    3120
ccgcgggccc gggatccacc ggtcgccacc atggtgagca agggcgagga gctgttcacc    3180
ggggtggtgc ccatcctggt cgagctggac ggcgacgtaa acggccacaa gttcagcgtg    3240
tccggcgagg gcgagggcga tgccacctac ggcaagctga ccctgaagtt catctgcacc    3300
accggcaagc tgcccgtgcc ctggcccacc ctcgtgacca ccttcggcta cggcctgcag    3360
tgcttcgccc gctacccaca tgaagcagca cgacttcttc aagtccgcca tgcccgaagg    3420
ctacgtccag gagcgcacca tcttcttcaa ggacgacggc aactacaaga cccgcgccga    3480
ggtgaagttc gagggcgaca ccctggtgaa ccgcatcgag ctgaagggca tcgacttcaa    3540
ggaggacggc aacatcctgg ggcacaagct ggagtacaac tacaacagcc acaacgtcta    3600
tatcatggcc gacaagcaga gaacggcat caaggtgaac ttcaagatcc gccacaacat    3660
cgaggacggc agcgtgcagc tcgccgacca ctaccagcag aacacccca tcggcgacgg    3720 ccccgtgctg ctgcccgaca ccactacct gagctaccag tccgccctga caaagaccc    3780 caacgagaag cgcgatcaca tggtcctgct ggagttcgtg accgccgccg ggatcactct    3840
cggcatggac gagctgtaca gtaaagcgg ccgcgactct agatcataat cagccatacc    3900
acatttgtag aggttttact tgctttaaaa aacctcccac acctccccct gaacctgaaa    3960
cataaaatga atgcaattgt tgttgttaac ttgtttattg cagcttataa tggttacaaa    4020
taaagcaata gcatcacaaa tttcacaaat aaagcatttt tttcactgc                 4069
```

<210> SEQ ID NO 7
<211> LENGTH: 33
<212> TYPE: DNA
<213> ORGANISM: Artificial sequence
<220> FEATURE:
<223> OTHER INFORMATION: L205.5w primer

<400> SEQUENCE: 7

```
ctgcgctgat gccagattgt atggtgttct ccc                                    33
```

<210> SEQ ID NO 8
<211> LENGTH: 33
<212> TYPE: DNA
<213> ORGANISM: Artificial sequence
<220> FEATURE:
<223> OTHER INFORMATION: L205.3w primer

<400> SEQUENCE: 8

```
gggagaacac catacaatct ggcatcagcg cag                                    33
```

<210> SEQ ID NO 9
<211> LENGTH: 37
<212> TYPE: DNA

```
<213> ORGANISM: Artificial sequence
<220> FEATURE:
<223> OTHER INFORMATION: L235.5 primer

<400> SEQUENCE: 9
ctgcaaaaca gctgagttcc aattgacctt ccacctg                                    37

<210> SEQ ID NO 10
<211> LENGTH: 37
<212> TYPE: DNA
<213> ORGANISM: Artificial sequence
<220> FEATURE:
<223> OTHER INFORMATION: L235.3 primer

<400> SEQUENCE: 10
caggtggaag gtcaattgga actcagctgt tttgcag                                    37

<210> SEQ ID NO 11
<211> LENGTH: 66
<212> TYPE: DNA
<213> ORGANISM: Artificial sequence
<220> FEATURE:
<223> OTHER INFORMATION: RI-stop_s primer

<400> SEQUENCE: 11
cagatcctca gagtgccgaa ttcttgagtg agttagagta gtgagctagt tgtctggtag           60
gggccc                                                                     66

<210> SEQ ID NO 12
<211> LENGTH: 66
<212> TYPE: DNA
<213> ORGANISM: Artificial sequence
<220> FEATURE:
<223> OTHER INFORMATION: RI-stop_a primer

<400> SEQUENCE: 12
gggcccctac cagacaacta gctcactact ctaactcact caagaattcg gcactctgag           60
gatctg                                                                     66

<210> SEQ ID NO 13
<211> LENGTH: 60
<212> TYPE: DNA
<213> ORGANISM: Artificial sequence
<220> FEATURE:
<223> OTHER INFORMATION: H-Xh-Xb_s primer

<400> SEQUENCE: 13
ggccgaggca ccaagttcaa gcttgctcga gatctagagg tcgccaccat ggtgagcaag           60

<210> SEQ ID NO 14
<211> LENGTH: 60
<212> TYPE: DNA
<213> ORGANISM: Artificial sequence
<220> FEATURE:
<223> OTHER INFORMATION: H-Xh-Xb_a primer

<400> SEQUENCE: 14
cttgctcacc atggtggcga cctctagatc tcgagcaagc ttgaacttgg tgcctcggcc           60

<210> SEQ ID NO 15
<211> LENGTH: 24
<212> TYPE: DNA
<213> ORGANISM: Artificial sequence
<220> FEATURE:
<223> OTHER INFORMATION: SK-15 primer
```

```
<400> SEQUENCE: 15
tgggcggtag gcgtgtacgg tggg                                           24

<210> SEQ ID NO 16
<211> LENGTH: 24
<212> TYPE: DNA
<213> ORGANISM: Artificial sequence
<220> FEATURE:
<223> OTHER INFORMATION: SK-16 primer

<400> SEQUENCE: 16
cagcttgccg gtggtgcaga tgaa                                           24

<210> SEQ ID NO 17
<211> LENGTH: 23
<212> TYPE: DNA
<213> ORGANISM: Artificial sequence
<220> FEATURE:
<223> OTHER INFORMATION: SK-17 primer

<400> SEQUENCE: 17
cagatccgct agcgctaccg gac                                            23

<210> SEQ ID NO 18
<211> LENGTH: 22
<212> TYPE: DNA
<213> ORGANISM: Artificial sequence
<220> FEATURE:
<223> OTHER INFORMATION: EYFP(-)1 primer

<400> SEQUENCE: 18
ctgctcacct tcttgattgc tg                                             22

<210> SEQ ID NO 19
<211> LENGTH: 21
<212> TYPE: DNA
<213> ORGANISM: Artificial sequence
<220> FEATURE:
<223> OTHER INFORMATION: EYFP(-)2 primer

<400> SEQUENCE: 19
gttcaggggg aggtgtggga g                                              21

<210> SEQ ID NO 20
<211> LENGTH: 18
<212> TYPE: DNA
<213> ORGANISM: Artificial sequence
<220> FEATURE:
<223> OTHER INFORMATION: BAC-1 primer

<400> SEQUENCE: 20
gccattgtaa tgagacgc                                                  18

<210> SEQ ID NO 21
<211> LENGTH: 22
<212> TYPE: DNA
<213> ORGANISM: Artificial sequence
<220> FEATURE:
<223> OTHER INFORMATION: BAC-2 primer

<400> SEQUENCE: 21
ccatctcgca aataaataag ta                                             22

<210> SEQ ID NO 22
```

<211> LENGTH: 20
<212> TYPE: DNA
<213> ORGANISM: Artificial sequence
<220> FEATURE:
<223> OTHER INFORMATION: BAC-3 primer

<400> SEQUENCE: 22
tgtaaatcaa caacgcacag                                               20

<210> SEQ ID NO 23
<211> LENGTH: 82
<212> TYPE: DNA
<213> ORGANISM: Artificial sequence
<220> FEATURE:
<223> OTHER INFORMATION: AUGback_s primer

<400> SEQUENCE: 23
gctcaccttc atgattgctg ccacttacaa cttcgccgtc cttaaactca tgggccgagg    60
caccaagttc gaaagcttcg cc                                            82

<210> SEQ ID NO 24
<211> LENGTH: 82
<212> TYPE: DNA
<213> ORGANISM: Artificial sequence
<220> FEATURE:
<223> OTHER INFORMATION: AUGback_a primer

<400> SEQUENCE: 24
ggcgaagctt tcgaacttgg tgcctcggcc catgagttta aggacggcga agttgtaagt    60
ggcagcaatc atgaaggtga gc                                            82

<210> SEQ ID NO 25
<211> LENGTH: 46
<212> TYPE: DNA
<213> ORGANISM: Artificial sequence
<220> FEATURE:
<223> OTHER INFORMATION: Luc-1 primer

<400> SEQUENCE: 25
gagtaagctt cgccaccatg aagacgcca aaacataaa gaaagg                    46

<210> SEQ ID NO 26
<211> LENGTH: 35
<212> TYPE: DNA
<213> ORGANISM: Artificial sequence
<220> FEATURE:
<223> OTHER INFORMATION: Luc-2 primer

<400> SEQUENCE: 26
ctgactcgag ttacacggcg atctttccgc ccttc                              35

<210> SEQ ID NO 27
<211> LENGTH: 42
<212> TYPE: DNA
<213> ORGANISM: Artificial sequence
<220> FEATURE:
<223> OTHER INFORMATION: TK-1 primer

<400> SEQUENCE: 27
gagtaagctt cgccaccatg gcttcgtacc ccggccatca ac                      42

<210> SEQ ID NO 28
<211> LENGTH: 37
<212> TYPE: DNA
<213> ORGANISM: Artificial sequence
<220> FEATURE:
<223> OTHER INFORMATION: TK-2 primer

<400> SEQUENCE: 28
ctgactcgag gtctccttcc gtgtttcagt tagcctc                    37

<210> SEQ ID NO 29
<211> LENGTH: 48
<212> TYPE: DNA
<213> ORGANISM: Artificial sequence
<220> FEATURE:
<223> OTHER INFORMATION: CAT-1 primer

<400> SEQUENCE: 29
gagtaagctt cgccaccatg gagaaaaaaa tcactggata taccaccg        48

<210> SEQ ID NO 30
<211> LENGTH: 31
<212> TYPE: DNA
<213> ORGANISM: Artificial sequence
<220> FEATURE:
<223> OTHER INFORMATION: CAT-2 primer

<400> SEQUENCE: 30
ctgactcgag ttacgccccg ccctgccact c                          31

<210> SEQ ID NO 31
<211> LENGTH: 47
<212> TYPE: DNA
<213> ORGANISM: Artificial sequence
<220> FEATURE:
<223> OTHER INFORMATION: LacZ-1 primer

<400> SEQUENCE: 31
gagtaagctt cgccaccatg tcgtttactt tgaccaacaa gaacgtg         47

<210> SEQ ID NO 32
<211> LENGTH: 46
<212> TYPE: DNA
<213> ORGANISM: Artificial sequence
<220> FEATURE:
<223> OTHER INFORMATION: LacZ-2 primer

<400> SEQUENCE: 32
ctgactcgag ttatttttga caccagacca actggtaatg gtagcg          46

<210> SEQ ID NO 33
<211> LENGTH: 53
<212> TYPE: DNA
<213> ORGANISM: Artificial sequence
<220> FEATURE:
<223> OTHER INFORMATION: Sr39-1 primer

<400> SEQUENCE: 33
ggccctcacc atcttcctcg accgccatcc catcgccttc atgctgtgct acc  53

<210> SEQ ID NO 34
<211> LENGTH: 53
<212> TYPE: DNA
<213> ORGANISM: Artificial sequence
<220> FEATURE:
<223> OTHER INFORMATION: Sr39-2 primer

<400> SEQUENCE: 34
ggtagcacag catgaaggcg atgggatggc ggtcgaggaa gatggtgagg gcc  53

<210> SEQ ID NO 35
<211> LENGTH: 32
<212> TYPE: DNA
<213> ORGANISM: Artificial sequence
<220> FEATURE:
<223> OTHER INFORMATION: CMV-1 primer

<400> SEQUENCE: 35
gagtaggcct ccgtattacc gccatgcatt ag                                    32

<210> SEQ ID NO 36
<211> LENGTH: 23
<212> TYPE: DNA
<213> ORGANISM: Artificial sequence
<220> FEATURE:
<223> OTHER INFORMATION: CMV-2 primer

<400> SEQUENCE: 36
ctcaagaatt cggcactctg agg                                              23

<210> SEQ ID NO 37
<211> LENGTH: 100
<212> TYPE: DNA
<213> ORGANISM: Artificial sequence
<220> FEATURE:
<223> OTHER INFORMATION: PolyA-1 primer

<400> SEQUENCE: 37
ctaggtgttg ttgttaactt gtttattgca gcttataatg gttacaaata aagcaatagc      60
atcacaaatt tcacaaataa agcatttttt tcactgcatg                           100

<210> SEQ ID NO 38
<211> LENGTH: 92
<212> TYPE: DNA
<213> ORGANISM: Artificial sequence
<220> FEATURE:
<223> OTHER INFORMATION: PolyA-2 primer

<400> SEQUENCE: 38
cagtgaaaaa aatgctttat ttgtgaaatt tgtgatgcta ttgctttatt tgtaaccatt      60
ataagctgca ataaacaagt taacaacaac ac                                    92

<210> SEQ ID NO 39
<211> LENGTH: 1977
<212> TYPE: DNA
<213> ORGANISM: Artificial sequence
<220> FEATURE:
<223> OTHER INFORMATION: nucleotides 1-846 represent TRplp and a linker
      sequence; nucleotides 847-1977 represent TKsr39

<400> SEQUENCE: 39
ttgagtgagt tagagtagtg agctagttgt ctggtagggg ccccctttgc ttccctggtg      60
gccactggat tgtgtttctt tggagtggca ctgttctgtg gatgtggaca tgaagctctc     120
actggtacag aaaagctaat tgagacctat ttctccaaaa actaccagga ctatgagtat     180
ctcattaatg tgattcatgc tttccagtat gtcatctatg aactgcctc tttcttcttc     240 ctttatgggg ccctcctgct ggctgagggc ttctacacca ccgcgctgt caggcagatc     300 tttggcgact acaagaccac catctgcggc aagggcctga gcgcaacggt aacaggggc     360 cagaagggga ggggttccag aggccaacat caagctcatt ctttggagcg ggtgtgtcat     420
tgtttgggaa aatggctagg acatcccgac aagtttgtgg gcatcaccta tgccctgact     480

```
gttgtatggc tcctggtgtt tgcctgctcg gctgtacctg tgtacattta cttcaatacc    540
tggaccacct gtcagtctat tgccttccct agcaagacct ctgccagtat aggcagtctc    600
tgcgctgatg ccagattgta tggtgttctc ccatggaatg cttccctgg caaggtttgt     660 ggctccaacc ttctgtccat ctgcaaaaca gctgagttcc aattgacctt ccacctgttt    720
attgctgcgt tgtgggtgc tgcggccaca ctagtttccc tgctcacctt catgattgct     780
gccacttaca acttcgccgt ccttaaactc atgggccgag caccaagtt cgaaagcttc     840 gccaccatgg cttcgtaccc cggccatcaa cacgcgtctg cgttcgacca ggctgcgcgt    900
tctcgcggcc atagcaaccg acgtacggcg ttgcgccctc gccggcagca agaagccacg    960
gaagtccgcc cggagcagaa aatgcccacg ctactgcggg tttatataga cggtccccac   1020
gggatgggga aaaccaccac cacgcaactg ctggtggccc tgggttcgcg cgacgatatc   1080
gtctacgtac ccgagccgat gacttactgg cgggtgctgg ggcttccga caatcgcg     1140 aacatctaca ccacacaaca ccgcctcgac cagggtgaga tatcggccgg ggacgcggcg   1200
gtggtaatga caagcgccca gataacaatg ggcatgcctt atgccgtgac cgacgccgtt   1260
ctggctcctc atatcggggg ggaggctggg agctcacatg ccccgccccc ggccctcacc   1320
atcttcctcg accgccatcc catcgccttc atgctgtgct accggccgc gcggtacctt    1380 atgggcagca tgaccccca ggccgtgctg gcgttcgtgg ccctcatccc gccgaccttg    1440
cccggcacca acatcgtgct ggggccctt ccggaggaca gacacatcga ccgcctggcc   1500
aaacgccagc gccccggcga gcggctggac ctggctatgc tggctgcgat cgccgcgtt   1560 tacgggctac ttgccaatac ggtgcggtat ctgcagtgcg gcgggtcgtg gcgggaggac   1620
tggggacagc tttcggggac ggccgtgccg ccccagggtg ccgagcccca gagcaacgcg   1680
ggcccacgac cccatatcgg ggacacgtta tttaccctgt ttcggccccc cgagttgctg   1740
gcccccaacg gcgacctgta taacgtgttt gcctgggcct tggacgtctt ggccaaacgc   1800
ctccgttcca tgcacgtctt tatcctggat tacgaccaat cgcccgccgg ctgccgggac   1860
gccctgctgc aacttacctc cgggatggtc cagacccacg tcaccacccc cggctccata   1920
ccgacgatat gcgacctggc gcgcacgttt gcccgggaga tggggaggc taactga      1977
```

<210> SEQ ID NO 40
<211> LENGTH: 1872
<212> TYPE: DNA
<213> ORGANISM: Artificial sequence
<220> FEATURE:
<223> OTHER INFORMATION: nucleotides 1-741 represent TRdm and a linker
      sequence; nucleotides 742-1872 represent TKsr39

<400> SEQUENCE: 40

```
ttgagtgagt tagagtagtg agctagttgt ctggtagggg ccccctttgc ttccctggtg     60
gccactggat tgtgtttctt tggagtggca ctgttctgtg gatgtggaca tgaagctctc    120
actggtacag aaaagctaat tgagacctat ttctccaaaa actaccagga ctatgagtat    180
ctcattaatg tgattcatgc tttccagtat gtcatctatg aactgcctc tttcttcttc    240 ctttatgggg ccctcctgct ggctgagggc ttctacacca ccggcgctgt caggcagatc    300
tttggcgact acaagaccac catctgcggc aagggcctga cgcaacgtt tgtgggcatc   360 acctatgccc tgactgttgt atggctcctg tgtttgcct gctcggctgt acctgtgtac     420
atttacttca atacctggac cacctgtcag tctattgcct ccctagcaa gacctctgcc    480 agtataggca gtctctgcgc tgatgccaga ttgtatggtg ttctcccatg gaatgctttc    540
```

```
cctggcaagg tttgtggctc caaccttctg tccatctgca aaacagctga gttccaattg    600
accttccacc tgtttattgc tgcgtttgtg ggtgctgcgg ccacactagt ttccctgctc    660
accttcatga ttgctgccac ttacaacttc gccgtcctta aactcatggg ccgaggcacc    720
aagttcgaaa gcttcgccac catggcttcg taccccggcc atcaacacgc gtctgcgttc    780
gaccaggctg cgcgttctcg cggccatagc aaccgacgta cggcgttgcg ccctcgccgg    840
cagcaagaag ccacggaagt ccgcccggag cagaaaatgc ccacgctact gcgggtttat    900
atagacggtc cccacgggat ggggaaaacc accaccacgc aactgctggt ggccctgggt    960
tcgcgcgacg atatcgtcta cgtacccgag ccgatgactt actggcgggt gctgggggct   1020
tccgagacaa tcgcgaacat ctacaccaca caacaccgcc tcgaccaggg tgagatatcg   1080
gccggggacg cggcggtggt aatgacaagc gcccagataa caatgggcat gccttatgcc   1140
gtgaccgacg ccgttctggc tcctcatatc ggggggagg ctgggagctc acatgccccg   1200
cccccggccc tcaccatctt cctcgaccgc atcccatcg ccttcatgct gtgctacccg   1260
gccgcgcggt accttatggg cagcatgacc ccccaggccc tgctggcgtt cgtggccctc   1320
atcccgccga ccttgcccgg caccaacatc gtgcttgggg cccttccgga ggacagacac   1380
atcgaccgcc tggccaaacg ccagcgcccc ggcgagcggc tggacctggc tatgctggct   1440
gcgattcgcc gcgtttacgg gctacttgcc aatacggtgc ggtatctgca gtgcggcggg   1500
tcgtggcggg aggactgggg acagctttcg gggacgccg tgccgcccca gggtgccgag   1560
ccccagagca acgcgggccc acgaccccat atcgggggaca cgttatttac cctgtttcgg   1620
gcccccgagt tgctggcccc caacggcgac ctgtataacg tgtttgcctg ggccttggac   1680
gtcttggcca aacgcctccg ttccatgcac gtctttatcc tggattacga ccaatcgccc   1740
gccggctgcc gggacgccct gctgcaactt acctccggga tggtccagac ccacgtcacc   1800 accccccggct ccataccgac gatatgcgac ctggcgcgca cgtttgcccg ggagatgggg   1860
gaggctaact ga                                                        1872
```

<210> SEQ ID NO 41
<211> LENGTH: 72
<212> TYPE: PRT
<213> ORGANISM: Homo sapiens

<400> SEQUENCE: 41

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Thr Leu Val Ser
        35                  40                  45

Leu Leu Thr Phe Met Ile Ala Ala Thr Tyr Asn Phe Ala Val Leu Lys
    50                  55                  60

Leu Met Gly Arg Gly Thr Lys Phe
65                  70

<210> SEQ ID NO 42
<211> LENGTH: 72
<212> TYPE: PRT
<213> ORGANISM: Pongo pygmaeus

<400> SEQUENCE: 42

Met Tyr Gly Val Leu Pro Trp Asn Ala Phe Pro Gly Lys Val Cys Gly
1               5                   10                  15

```
Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Val Ser
        35                  40                  45

Leu Leu Thr Phe Met Ile Ala Ala Thr Tyr Asn Phe Ala Val Leu Lys
    50                  55                  60

Leu Met Gly Arg Gly Thr Lys Phe
65                  70

<210> SEQ ID NO 43
<211> LENGTH: 72
<212> TYPE: PRT
<213> ORGANISM: Pan troglodytes

<400> SEQUENCE: 43

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Val Ser
        35                  40                  45

Leu Leu Thr Phe Met Ile Ala Ala Thr Tyr Asn Phe Ala Val Leu Lys
    50                  55                  60

Leu Met Gly Arg Gly Thr Lys Phe
65                  70

<210> SEQ ID NO 44
<211> LENGTH: 72
<212> TYPE: PRT
<213> ORGANISM: Macaca mulatta

<400> SEQUENCE: 44

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Ile Ser
        35                  40                  45

Leu Leu Thr Phe Met Ile Ala Ala Thr Tyr Asn Phe Ala Val Leu Lys
    50                  55                  60

Leu Met Gly Arg Gly Thr Lys Phe
65                  70

<210> SEQ ID NO 45
<211> LENGTH: 72
<212> TYPE: PRT
<213> ORGANISM: Macaca fascicularis

<400> SEQUENCE: 45

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Ile Ser
        35                  40                  45

Leu Leu Thr Phe Met Ile Ala Ala Thr Tyr Asn Phe Ala Val Leu Lys
    50                  55                  60
```

Leu Met Gly Arg Gly Thr Lys Phe
65                  70

<210> SEQ ID NO 46
<211> LENGTH: 72
<212> TYPE: PRT
<213> ORGANISM: Sus scrofa

<400> SEQUENCE: 46

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Val Ser
        35                  40                  45

Leu Leu Thr Phe Met Ile Ala Ala Thr Tyr Asn Phe Ala Val Leu Lys
    50                  55                  60

Leu Met Gly Arg Gly Thr Lys Phe
65                  70

<210> SEQ ID NO 47
<211> LENGTH: 72
<212> TYPE: PRT
<213> ORGANISM: Mus musculus

<400> SEQUENCE: 47

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Val Ser
        35                  40                  45

Leu Leu Thr Phe Met Ile Ala Ala Thr Tyr Asn Phe Ala Val Leu Lys
    50                  55                  60

Leu Met Gly Arg Gly Thr Lys Phe
65                  70

<210> SEQ ID NO 48
<211> LENGTH: 72
<212> TYPE: PRT
<213> ORGANISM: Rattus norvegicus

<400> SEQUENCE: 48

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Val Ser
        35                  40                  45

Leu Leu Thr Phe Met Ile Ala Ala Thr Tyr Asn Phe Ala Val Leu Lys
    50                  55                  60

Leu Met Gly Arg Gly Thr Lys Phe
65                  70

<210> SEQ ID NO 49
<211> LENGTH: 72
<212> TYPE: PRT
<213> ORGANISM: Monodelphis domestica

<400> SEQUENCE: 49

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Ile Gly Ala Ala Ala Thr Leu Val Ser
            35                  40                  45

Leu Leu Thr Phe Met Ile Ala Ala Thr Tyr Asn Phe Ala Val Leu Lys
        50                  55                  60

Leu Met Gly Arg Gly Thr Lys Phe
65              70

<210> SEQ ID NO 50
<211> LENGTH: 72
<212> TYPE: PRT
<213> ORGANISM: Oryctolagus cuniculus

<400> SEQUENCE: 50

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Val Ser
            35                  40                  45

Leu Leu Thr Phe Met Ile Ala Ala Thr Tyr Asn Phe Ala Val Leu Lys
        50                  55                  60

Leu Met Gly Arg Gly Thr Lys Phe
65              70

<210> SEQ ID NO 51
<211> LENGTH: 72
<212> TYPE: PRT
<213> ORGANISM: Bos taurus

<400> SEQUENCE: 51

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Val Ser
            35                  40                  45

Leu Leu Thr Phe Met Ile Ala Ala Thr Tyr Asn Phe Ala Val Leu Lys
        50                  55                  60

Leu Met Gly Arg Gly Thr Lys Phe
65              70

<210> SEQ ID NO 52
<211> LENGTH: 72
<212> TYPE: PRT
<213> ORGANISM: Canis familiaris

<400> SEQUENCE: 52

Met Tyr Gly Val Leu Pro Trp Asn Ala Phe Pro Gly Lys Val Cys Gly
1               5                   10                  15

Ser Asn Leu Leu Ser Ile Cys Lys Thr Ala Glu Phe Gln Met Thr Phe
            20                  25                  30

His Leu Phe Ile Ala Ala Phe Val Gly Ala Ala Ala Thr Leu Val Ser
            35                  40                  45

```
Leu Leu Thr Phe Met Ile Ala Ala Thr Tyr Asn Phe Ala Val Leu Lys
    50                  55                  60
Leu Met Gly Arg Gly Thr Lys Phe
65                  70
```

<210> SEQ ID NO 53
<211> LENGTH: 72
<212> TYPE: PRT
<213> ORGANISM: Gallus gallus

<400> SEQUENCE: 53

```
Met Tyr Gly Val Leu Pro Trp Asn Ala Phe Pro Gly Lys Val Cys Gly
1               5                   10                  15

Ser Asn Leu Leu Ser Ile Cys Lys Thr Ser Glu Phe Gln Met Thr Phe
                20                  25                  30

His Leu Phe Ile Ala Ala Phe Val Gly Ala Ala Ala Thr Leu Val Ser
            35                  40                  45

Leu Leu Thr Phe Met Ile Ala Ala Thr Tyr Asn Phe Ala Val Leu Lys
    50                  55                  60

Leu Met Gly Arg Gly Thr Lys Phe
65                  70
```

<210> SEQ ID NO 54
<211> LENGTH: 72
<212> TYPE: PRT
<213> ORGANISM: Taeniopygia guttata

<400> SEQUENCE: 54

```
Met Tyr Gly Ile Leu Pro Trp Asn Ala Phe Pro Gly Lys Val Cys Gly
1               5                   10                  15

Ser Asn Leu Leu Ser Ile Cys Lys Thr Ser Glu Phe Gln Met Thr Phe
                20                  25                  30

His Leu Phe Ile Ala Ala Phe Val Gly Ala Ala Ala Thr Leu Val Ser
            35                  40                  45

Leu Val Thr Phe Ile Ile Ala Thr Thr Tyr Asn Phe Ala Val Leu Arg
    50                  55                  60

Leu Met Gly Arg Gly Thr Lys Phe
65                  70
```

<210> SEQ ID NO 55
<211> LENGTH: 72
<212> TYPE: PRT
<213> ORGANISM: Gekko gecko

<400> SEQUENCE: 55

```
Met Tyr Gly Val Leu Pro Trp Asn Ala Ser Pro Gly Arg Val Cys Gly
1               5                   10                  15

Gln Ser Leu Leu Ser Ile Cys Lys Thr Ala Glu Phe Gln Met Thr Phe
                20                  25                  30

His Leu Phe Ile Ala Ala Phe Val Gly Ala Ala Ile Thr Leu Val Ala
            35                  40                  45

Leu Leu Thr Phe Ile Ile Ala Ala Thr Tyr Asn Phe Ala Val Leu Lys
    50                  55                  60

Leu Met Gly Arg Gly Thr Lys Phe
65                  70
```

<210> SEQ ID NO 56
<211> LENGTH: 74
<212> TYPE: PRT

<213> ORGANISM: Xenopus laevis

<400> SEQUENCE: 56

```
Met Tyr Gly Val Leu Pro Trp Asn Ala Phe Pro Gly Lys Val Cys Gly
1               5                   10                  15

Thr Ser Leu Leu Ala Ile Cys Lys Thr Ser Glu Phe Gln Met Thr Phe
            20                  25                  30

His Leu Phe Ile Ala Ala Phe Val Gly Ala Ala Ala Thr Leu Val Ala
        35                  40                  45

Leu Leu Thr Tyr Met Val Gly Ala Ser Phe Asn Tyr Ala Val Leu Arg
    50                  55                  60

Val Thr Gly Arg Ser Asp Arg Ser Lys Phe
65                  70
```

<210> SEQ ID NO 57
<211> LENGTH: 79
<212> TYPE: PRT
<213> ORGANISM: Latimeria chalumnae

<400> SEQUENCE: 57

```
Met Asp Pro Arg Gln Tyr Gly Val Leu Pro Trp Thr Ala Thr Pro Gly
1               5                   10                  15

Lys Val Cys Gly Met Ala Leu Val Ser Ile Cys Asn Lys Pro Glu Phe
            20                  25                  30

Asn Met Thr Tyr His Leu Phe Ile Thr Ala Phe Thr Gly Ala Ala Ala
        35                  40                  45

Thr Leu Val Ser Leu Leu Thr Tyr Met Met Ser Thr Thr Tyr Asn Phe
    50                  55                  60

Ala Val Leu Arg Phe Leu Gly Arg Glu Asp Phe Cys Thr Lys Phe
65                  70                  75
```

<210> SEQ ID NO 58
<211> LENGTH: 729
<212> TYPE: DNA
<213> ORGANISM: Mus musculus

<400> SEQUENCE: 58

```
atgggcttgt tagagtgttg tgctagatgt ctggtagggg ccccctttgc ttccctggtg      60
gccactggat tgtgtttctt tggagtggca ctgttctgtg gatgtggaca tgaagctctc     120
actggtacag aaaagctaat tgagacctat ttctccaaaa actaccagga ctatgagtat     180
ctcattaatg tgattcatgc tttccagtat gtcatctatg gaactgcctc tttcttcttc     240
ctttatgggg ccctcctgct ggctgagggc ttctacacca ccggcgctgt caggcagatc     300
tttggcgact acaagaccac catctgcggc aagggcctga cgcaacgtt tgtgggcatc      360 acctatgccc tgactgttgt atggctcctg gtgtttgcct gctcggctgt acctgtgtac     420
atttacttca atacctggac cacctgtcag tctattgcct ccctagcaa gacctctgcc      480 agtataggca gtctctgcgc tgatgccaga atgtatggtg ttctcccatg gaatgctttc     540
cctggcaagg tttgtggctc caaccttctg tccatctgca aaacagctga gttccaaatg     600
accttccacc tgtttattgc tgcgtttgtg ggtgctgcgg ccacactagt ttccctgctc     660
accttcatga ttgctgccac ttacaacttc gccgtcctta aactcatggg ccgaggcacc     720
aagttctga                                                             729
```

<210> SEQ ID NO 59
<211> LENGTH: 834

```
<212> TYPE: DNA
<213> ORGANISM: Mus musculus

<400> SEQUENCE: 59
atgggcttgt tagagtgttg tgctagatgt ctggtagggg ccccctttgc ttccctggtg    60
gccactggat tgtgtttctt tggagtggca ctgttctgtg gatgtggaca tgaagctctc   120
actggtacag aaaagctaat tgagacctat ttctccaaaa actaccagga ctatgagtat   180
ctcattaatg tgattcatgc tttccagtat gtcatctatg gaactgcctc tttcttcttc   240
ctttatgggg ccctcctgct ggctgagggc ttctacacca ccggcgctgt caggcagatc   300
tttggcgact acaagaccac catctgcggc aagggcctga gcgcaacggt aacaggggc   360
cagaagggga ggggttccag aggccaacat caagctcatt ctttggagcg ggtgtgtcat   420
tgtttgggaa atggctagg acatcccgac aagtttgtgg gcatcaccta tgccctgact   480
gttgtatggc tcctggtgtt tgcctgctcg gctgtacctg tgtacattta cttcaatacc   540
tggaccacct gtcagtctat tgccttccct agcaagacct ctgccagtat aggcagtctc   600
tgcgctgatg ccagaatgta tggtgttctc ccatggaatg cttcccctgg caaggtttgt   660
ggctccaacc ttctgtccat ctgcaaaaca gctgagttcc aaatgacctt ccacctgttt   720
attgctgcgt tgtgggtgc tgcggccaca ctagttccc tgctcacctt catgattgct   780
gccacttaca acttcgccgt ccttaaactc atgggccgag caccaagtt ctga          834

<210> SEQ ID NO 60
<211> LENGTH: 729
<212> TYPE: DNA
<213> ORGANISM: Homo sapiens

<400> SEQUENCE: 60
atgggcttgt tagagtgctg tgcaagatgt ctggtagggg ccccctttgc ttccctggtg    60
gccactggat tgtgtttctt tggggtggca ctgttctgtg gctgtggaca tgaagccctc   120
actggcacag aaaagctaat tgagacctat ttctccaaaa actaccaaga ctatgagtat   180
ctcatcaatg tgatccatgc cttcagtat gtcatctatg gaactgcctc tttcttcttc   240
ctttatgggg ccctcctgct ggctgagggc ttctacacca ccggcgcagt caggcagatc   300
tttggcgact acaagaccac catctgcggc aagggcctga gcgcaacgtt gtgggcatc   360
acctatgccc tgaccgttgt gtggctcctg tgtttgcct gctctgctgt gcccgtgtac   420
atttacttca cacctggac cacctgcgac tctattgcct tccccagcaa gacctctgcc   480
agtataggca gtctctgtgc tgacgccaga atgtatggtt tctcccatg gaatgctttc   540
cctggcaagg tttgtggctc caaccttctg tccatctgca aaacagctga gttccaaatg   600
accttccacc tgtttattgc tgcatttgtg gggctgcag ctacactggt ttccctgctc   660
accttcatga ttgctgccac ttacaacttt gccgtcctta aactcatggg ccgaggcacc   720
aagttctga                                                           729

<210> SEQ ID NO 61
<211> LENGTH: 850
<212> TYPE: DNA
<213> ORGANISM: Homo sapiens

<400> SEQUENCE: 61
atgggcttgt tagagtgctg tgcaagatgt ctggtagggg ccccctttgc ttccctggtg    60
gccactggat tgtgtttctt tggggtggca ctgttctgtg gctgtggaca tgaagccctc   120
```

```
actggcacag aaaagctaat tgagacctat ttctccaaaa actaccaaga ctatgagtat    180
ctcatcaatg tgatccatgc cttccagtat gtcatctatg gaactgcctc tttcttcttc    240
ctttatgggg ccctcctgct ggctgagggc ttctacacca ccggcgcagt caggcagatc    300
tttggcgact acaagaccac catctgcggc aagggcctga gcgcaacggt aacagggggc    360
cagaagggga ggggttccag aggccaacat caagctcatt ctttggagcg ggtgtgtcat    420
tgtttgggaa aatggctagg acatcccgac aagtttgtgg gcatcaccta tgccctgacc    480
gttgtgtggc tcctggtgtt tgcctgctct gctgtgcccg tgtacattta cttcaacacc    540
tggaccacct gcgactctat tgccttcccc agcaagacct ctgccagtat aggcagtctc    600
tgtgctgacg ccagaatgta tggtgttctc ccatggaatg ctttccctgg caaggtttgt    660
ggctccaacc ttctgtccat ctgcaaaaca gctgagttcc aaatgacctt ccacctgttt    720
attgctgcat ttgtgggggc tgcagctaca ctggtttccc tgctcacctt catgattgct    780
gccacttaca actttgccgt ccttaaactc atgggccgag gcaccaagtt ctgatacact    840
ggtttccctg                                                           850

<210> SEQ ID NO 62
<211> LENGTH: 834
<212> TYPE: DNA
<213> ORGANISM: Artificial Sequence
<220> FEATURE:
<223> OTHER INFORMATION: Vertebrate PLP/DM20 consensus sequence
<220> FEATURE:
<221> NAME/KEY: n
<222> LOCATION: (24)..(24)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: n
<222> LOCATION: (708)..(708)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: n
<222> LOCATION: (744)..(744)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t

<400> SEQUENCE: 62
atgggyykgy wdgakkgytg yrynmgmtgy mtbrtwgggg ymccmttygc ytchbtsrtb     60
gccacwgkvy tvtgyttyky tggrgtsgcv ctvttctgyg gmtgyggrca ygargchytv    120
asygghacmg armagytvat ygagacmtay ttytccaara aytaccaaga mtaygartay    180
ctcatyvayg tsatymaygc yttycagtay gtcatctatg gaaywgccwy yttcttctty    240
cthtwyggrr ycctvctkyt ggcygarggm ttctacacca cmrsygchrt cargcavatc    300
ythggsgast wcmrrmccmc mryywkmrrs rrkggsctga kykcwacrgt racwggrggm    360
cmkaarggga grrghdcsmg rggmmvvcak cvagyycayw cywtrsagck srtstgtcrb    420
tgyttgggaa artggctmgg acayccygay aagtttgtsg gyrtyacyta tryyhtsacy    480
rtykkvtggm tmctrrystt ygcctgctcd gcygtdccyg tvtacatyta yttyaayacc    540
tggrycacyt gycagtctat ygcckyccch rssaagacyw cwrccagyrt mrgyasbcts    600
```

```
tgykcdgayg symgvatgta yggtgtycts ccmtggaayg cbttycchgg saargtktgy      660
ggswccarcc tkctbkccat ctgcaaracm rsygagttcc aratgacntt ycayctbttt      720
atygckgcvt tygtgggkgc wgcngchacw ctdgtbkcmc tgctcacytw yatgrthgsy      780
gcmwcwtwca actwygcygt sctbmrastb aykggccgrr gcwcmaagtt ytga            834

<210> SEQ ID NO 63
<211> LENGTH: 834
<212> TYPE: DNA
<213> ORGANISM: Artificial Sequence
<220> FEATURE:
<223> OTHER INFORMATION: Mammalian PLP/DM20 consensus sequence
<220> FEATURE:
<221> NAME/KEY: n
<222> LOCATION: (24)..(24)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 63
atgggcytgt tagagtgytg ygcnagatgy ctsgtagggg cccccttttgc ttccytggtg      60 gccactggat trtgtttctt tggrgtggca ctsttctgtg gmtgtggaca tgaagchytm     120
actggyacag aaaagytaat tgagacmtat ttctccaaaa aytaccaaga ctaygagtat     180
ctcatyaatg tgatycatgc yttccagtat gtcatctatg gaactgcctc tttcttcttc     240
ctttatgggg ccctcctgct ggcygagggc ttctacacca ccggygcwgt caggcagatc     300
tttggcgact acaagaccac catctgcggs aagggcctga gygcaacggt aacaggggc     360 cagaaggga ggggttccag aggccaacat caagctcatt ctttggagcg ggtgtgtcat     420
tgtttgggaa aatggctagg acatcccgac aagtttgtgg gcatcaccta tgccytgacy     480
gttgtrtggc tcctrgtgtt tgcctgctck gctgtrcctg tgtacattta yttcaayacc     540
tggaccacyt gycagtctat tgcckycccy agcaagacyt ctgccagyat aggcastctc     600
tgygctgatg ccagaatgta tggtgttctc ccatggaatg cttttyccwgg caargtktgt     660 ggctccaacc ttctgtccat ctgcaaaaca gctgagttcc aaatgacstt ccayctgttt     720
attgctgcvt tygtgggkgc tgcrgcyaca ctrgtktccc tgctcacctt catgattgct     780
gccacttaca acttygccgt cctkaaactc atgggccgag gcaccaagtt ctga            834
```